(12) United States Patent
Kim et al.

(10) Patent No.: US 6,747,050 B1
(45) Date of Patent: Jun. 8, 2004

(54) ISOXAZOLINE DERIVATIVE AND A PROCESS FOR THE PREPARATION THEREOF

(75) Inventors: Eunice Eun-Kyeong Kim, Daejeon (KR); Mi-Jeong Park, Daejeon (KR); Tae-Hee Lee, Daejeon (KR); Hye-Kyung Chang, Daejeon (KR); Tae-Kyo Park, Daejeon (KR); Chang-Yuil Kang, Seoul (KR); Young-Myeong Kim, Chunchon (KR); Kwang-Yul Moon, Daejeon (KR); Young-Leem Oh, Daejeon (KR); Chang-Hee Min, Daejeon (KR); Hyun-Ho Chung, Daejeon (KR)

(73) Assignee: LG Chem Investment Ltd., Seoul (KR)

( * ) Notice: Subject to any disclaimer, the term of this patent is extended or adjusted under 35 U.S.C. 154(b) by 0 days.

(21) Appl. No.: 10/088,288

(22) PCT Filed: Sep. 18, 2000

(86) PCT No.: PCT/KR00/01047

§ 371 (c)(1),
(2), (4) Date: Mar. 15, 2002

(87) PCT Pub. No.: WO01/21600

PCT Pub. Date: Mar. 29, 2001

(30) Foreign Application Priority Data

Sep. 17, 1999 (WO) ............................... PCT/KR99/00561
Nov. 4, 1999 (KR) ........................................ 1999-48608

(51) Int. Cl.[7] ...................... A61K 31/42; A61K 31/422; C07D 261/04
(52) U.S. Cl. ...................... 514/378; 548/240; 546/146; 546/169; 514/307; 514/314
(58) Field of Search ........................... 548/240; 514/378

(56) References Cited

U.S. PATENT DOCUMENTS

| 5,686,434 A | 11/1997 | Kleinman |
| 5,716,967 A | 2/1998 | Kleinman |

FOREIGN PATENT DOCUMENTS

| JP | 749428 | 12/1996 |
| JP | 11-180891 | 7/1999 |
| KR | 1999-79268 | 11/1999 |

OTHER PUBLICATIONS

Ju Young Lee et al., Journal of the Chemical Society, Perkin Transactions 1: Organic and Bio–Organic Chemistry, Jan. 199 (2), pp. 359–365.*

J.Y. Lee "Synthesis of Hexapeptide and Tetrapeptide Analogs of the Immunomodulating Peptides," J. Chem. Soc. Perkin Trans., 1998, vol. 1, No. 2, 359–366.

* cited by examiner

*Primary Examiner*—Laura L. Stockton
(74) *Attorney, Agent, or Firm*—Peter F. Corless; John B. Alexander; Edwards & Angell, LLP

(57) ABSTRACT

The present invention provides to an isoxazoline derivative of formula (I), the pharmaceutically acceptable salts, esters and stereochemically isomeric forms thereof, and the use of the derivative in inhibiting the activity of caspases. The present invention also provides a pharmaceutical composition for preventing inflammation and apoptosis which comprise the isoxazoline derivative, pharmaceutically acceptable salts, esters and stereochemically isomeric forms thereof and the process for preparing the same. The derivative according to the present invention can be effectively used in treating diseases due to caspases, such as, for example the disease in which cells are abnormally died, dementia, cerebral stroke, AIDS, diabetes, gastric ulcer, hepatic injury by hepatitis, sepsis, organ transplantation rejection reaction and anti-inflammation.

13 Claims, 18 Drawing Sheets

ISOXAZOLINE DERIVATIVE AND A PROCESS FOR THE PREPARATION THEREOF

This application is a 371 of PCT/KR00/01047 filed Sep. 18, 2000.

TECHNICAL FIELD

The present invention relates to a novel isoxazoline derivative, pharmaceutically acceptable salts, esters and stereochemically isomeric forms thereof which can serve as an inhibitor for protein caspases (cysteinyl-aspartate proteinases), a process for preparing the same and the use of the derivative as an inhibitor for caspases. The present invention also relates to a pharmaceutical composition for preventing inflammation and apoptosis which comprises the isoxazoline derivative, pharmaceutically acceptable salts, esters and stereochemically isomeric forms thereof and the process for preparing the same. The isoxazoline derivative according to the present invention can effectively be used in treating diseases due to caspases, for example, the disease in which cells are abnormally died, dementia, cerebral stroke, AIDS, diabetes, gastric ulcer, hepatic injure by hepatitis, sepsis, organ transplantation rejection reaction and anti-inflammation.

BACKGROUND ART

All organisms in nature undergo the life cycle consisting of development, differentiation, growth and death. Recently, an extensive research has been made to a mechanism involved in apoptosis which would play a key role in the control of the life cycle and the outbreak of diseases. It has been reported that apoptosis is occurred by a number of factors, but largely due to three kinds of cellular signal transport systems: the first of which is a signal transport system by the protein-protein interaction (See, Muzio M. et al., Cell 85, 817, 1996; Humke E. W. et al., JBC 273, 15702, 1998), the second, an incorporation of cytochrome C into cytoplasm via mitochondria (See, Liu X. et al., Cell 86:147, 1996; Li P. et al., Cell 91, 479, 1997), and the third, a cellular signal transport pathway by the SAPK(Stess-activated protein kinases) activation of mitogen-activation protein kinase (MAPK) enzymes. AU the pathways have been known to activate caspases cascade. As such caspases, about 10 kinds of isoenzymes in human and 14 kinds in mouse have been identified (see, Thornberry N. A. et al., Science 28, 1312 1998; Green D. R. Science 28, 1309, 1998; Ahmad A, et al., Cancer Res. 15, 5201 1998). The enzymes exist within the cells in the form of proenzyme which has no enzymatic activity and converted into an activated form if the cells are damaged or are exposed to a substance which leads to cellular necrosis. An activated enzyme has a heterodimer structure in which two polypeptides, i.e. larger subunits with the molecular weight of about 17–20 kDa, and smaller subunits with the molecular weight of about 10 kDa are bound together.

At present, caspases are classified into three (3) groups in view of the genetic identification analysis results and the biochemical characteristics: the first group is caspase-1, 4 and 5 which are responsible for the processing of cytokine activation, the second is caspase-3, 6 and 7 which carry out apoptosis and the third is caspase-8, 9 and 10 which are responsible for enzymatic activation in the upstream of signal transport system of apoptosis.

Among these caspases, Caspase-3 group and Caspase-8, 9, 10 etc. were recently reported to be related to apoptosis, and diseases (see, Thornberry N. A. et al., Science, 28, 1312, 1998).

According to the recent research results, caspases are commonly activated as apoptosis is initiated, even though there is a minor difference depending upon the tissues and cells. The activated caspases then activate intracellular CAD (Caspase-activated DNAse) which finally digests intra-nuclear DNA to result in cell death (Sakahira H., et al., Nature 1 96, 1998; Enari M et al., Nature 1 43, 1998). In addition, they promote apoptosis by decomposing substrate such as PARP (Poly-ADP ribose polymerase) which is necessary for the survival of cells.

Meantime, according to the recent disease-related researches, it was reported that the activity of Caspase-3 is increased in the brain of dementia patient which promotes the production of beta-amyloid peptide from beta-amyloid precursor protein that is considered to be a major cause of dementia, thereby accelerating the apoptosis of brain cells (see, Kuida K. et al., Nature 28, 368, 1996). Further, it was reported that activation of caspases can be the direct inducer of various diseases such as sepsis (see, Haendeler J. et al., Shock 6, 405, 1996; Lenhoff R J. et al., 29, 563, 1999), rheumatoid arthritis (Firestein G. S. et al., J. Clin Invest 96(3), 1631, 1995), cerebral stroke (see, Hill I. E. et al., Brain Res. 10, 398, 1995), ALS disease (see, Alexianu M. E. et al., J. Neurochem 63, 2365, 1994), autoimmune isease (see, Rieux-Laucat F, et al., Science 2, 1347, (1995), diabetes mellitusd(see, Junttl-Berggren et al., Science 2, 86, 1993), hepatitis (Haendeler J. et al., Shock 6, 405, 1996), organ transplantation rejection reaction (Koglin J. et al., Transplantation, 27, 904, 1999; Bergese S. D. et al., Transplantation 27, 904, 1999), gastric ulcer (see, Slomiany B. L. et al., J. Physiol. Pharmacol. 96, 1631, 1995), and the like.

The researches on three dimensional structure of caspase-1 and caspase-3, catalytic mechanism of the enzyme and enzyme-substrate specificity (see, Wilson, K. P et al., Nature 370, 270, 1994; Walker, N. P. C. et al., Cell 78, 343, 1994; Nature Struc. Biol. 3, 619, 1996) revealed that Caspase-1 group has a hydrolase-substrate specificity for the peptide sequence of (P4)-Val-X-Asp(P1) and Caspase-3 group has a hydrolase-substrate specificity for the sequence of (P4)Asp-X-X-Asp(P1).

Z-VAD-fluoromethyl ketone, and Z-DEVD-fluoromethyl ketone which mimics the above amino acid sequence have already been used in the researches on the inhibitors and were proven to have an inhibitory activity on apoptosis of hepatic cells by an activation of caspases (see, Rodriguez I. Et al., J. Exp. Med., 184, 2067, 1996; Rouquet N. et al., Curr Biol. 1, 1192, 1996; Kunstle G. et al., Immunol. Lett 55, 5, 1997), and on the apoptosis of brain cells by cerebral ischemias. However, since such peptide derivatives are deficient in drug property for clinical application, they cannot be used as therapeutics.

Fulminant hepatic failure (FHF) is a clinical syndrome resulting from massive death of liver cells or sudden and severe impairment of liver function (See: Trey, C. et al., 1970, Progress in liver disease, Popper, H. and F. Schaffner, eds. Grune and stratton, New York, pp282–298). The causes of FHF are diverse: hepatitis virus infection, drugs and toxins, alcohol, ischemia, metabolic disorder, massive malignant infiltration, chronic autoimmune hepatitis, etc. However, these mechanisms are not completely clear. Since the prognosis of FHF is very poor while its progress is very rapid, it is not uncommon that a patient falls in lethal condition in 1–2 weeks from the onset of this syndrome (See, Sherlock, S. 1993, Adv. Intern. Med. 38: 245–267). Consequently, the overall mortality in most series is very high. However, the hepatic lesion is potentially reversible, and survivors usually recover completely.

Different therapeutic options that have been tried in FHF include antibiotics, diuretics, corticosteroids, blood transfusion, charcoal haemoperfusion, and plasmaphresis. However, none of these methods have been shown to be effective in controlled studies. In recent years, liver transplantation is generally accepted as the only therapeutic option to actually improve the prognosis of this syndrome. However, liver transplantation cannot be the perfect treatment for FHF because of immune complication, viral or bacterial infection, and graft availability. Thus, a potent therapeutic agent which can protect hepatic cells from massive death during the acute phase is critically desired.

Apoptosis is a type of cell death characterized by a series of distinct morphological and biochemical changes accomplished by specialized cellular machinery. Apoptosis is an essential process to remove excess, unwanted and harmful cells and maintain homeostasis, but inappropriate apoptosis is implicated in many human diseases such as neurodegenerative diseases, ischaemic damage, autoimmune disorders, several forms of cancer. Recently, it became clear that apoptosis of hepatocytes is a critical cause of hepatic injury in viral hepatitis and alcoholic hepatitis and acute hepatic failure in fulminant hepatitis. Many changes which occur in a cell that received apoptotic signal reflect complex biochemical events carried out by a family of cysteine proteases called caspases.

Caspases inactivate proteins that protect living cells from apoptosis, such as $I^{CAD}$/DFF45, an inhibitor of the nuclease responsible for DNA fragmentation, and Bcl-2. At the same time, caspases contribute to apoptosis not only by direct disassembly of cell structures, but also by reorganizing cell structures indirectly by cleaving several proteins involved in cytoskeleton regulation. Since caspase activation is closely related to the initiating, propagating, and terminal event of most forms of apoptosis, this family of enzymes are attractive potential targets for the treatment of disorders resulted from excessive apoptosis or insufficient apoptosis.

Several kinds of caspase inhibitors have been identified. Four distinct classes of viral inhibitors have been described: CrmA, p35, a family of IAP (inhibitors of apoptosis), and the hepatitis B virus-encoded HBx protein (See, Gottlob, K et al., 1998, J. Biol. Chem. 273: 33347–33353). However, these molecules are not suitable as the therapeutic agent. Peptide-based caspase inhibitor such as z-VAD-fmk, z-DEVD-fmk, and Ac-YVAD-cmk has widely been used for research use and this inhibitor showed apoptosis-blocking activity in cellular level (See: Sane, A. T. et al., 1998, Cancer Res. 58: 3066–3072), in rodent models of liver injury caused by Fas or by TNFα (See: Kunstle, G. et al., 1997, Immunol. Lett. 55; 5–10) or ischemia after liver transplantation (See: Cursio, R. et al., 1999, FASEB J. 13: 253–261). Petak and colleagues showed that a bi-functional anticancer agent, BCNU (1,3-bis(2-chloroethyl)-1-nitrosourea) had caspase inhibiting activity and inhibited drug-induced apoptosis in vitro (See: Petak, I. et al., 1998, Cancer Res. 58: 614–618). Recently, cyclooxygenase-2 (COX-2) inhibitors are arousing interest as potential therapeutic agents of FHF (See, McCormick, P. A. et al., 1999, Lancet 353: 40–41). However, the efficacy of these materials has not been clinically verified yet.

In the meantime, development of new drugs depends primarily on the availability of suitable animal models relevant to human hepatitis or hepatocytic damage. It is therefore very important to adopt a suitable animal model relevant to human FHF to test efficacy of a candidate for therapeutic agent. Two types of experimental hepatitis model were reported. One is hepatic injury induced by bacterial lipopolysaccharide together with D-galactosamine (See: Galanos, C. et al., 1979, Proc. Natl. Acad Sci., 76: 5939; Lehman, V. et al., 1987, J. Exp. Med. 165–657), and the other is a recently developed experimental model, Con A-induced hepatitis (See: Tiegs, G. et al., 1992, J. Clin. Invest. 90: 196–203; Mizuhara, H. et al., 1994, J. Exp. Med. 179: 1529–1537). Con A-induced hepatitis model closely mimics human FHF in many respects, especially in the role of Fas in pathogenesis. Fas is abundantly expressed on the hepatocyte and FasL is expressed on activated T cells and functions as an effector of cytotoxic lymphocytes. Injection of agonistic monoclonal anti-Fas antibody into adult mice caused rapid hepatic failure, indicating that abnormally activated Fas-FasL system may play a role in human fulminant hepatitis which can be caused by the activation of immune system such as cytotoxic T cells. Accumulating data such as the involvement of specific CTLs in the pathogenesis of FHF, the sensitivity of primary hepatocytes to Fas-mediated apoptosis in vitro, and the overexpression of Fas in hepatocytes transformed with human hepatitis virus are consistent with tis hypothesis. In recent studies, the activation of Fas-FasL system has been proved to play an important role in the liver cell injury by Con A-induced hepatitis (See: Tagawa, Y. et al., 1998, Eur. J. Immunol. 28: 4105–4113). FasL was induced in the liver shortly after the Con A injection was predominantly expressed on intrahepatic T cells. These results indicate thar Fas-FasL system is a critical element in the development of Con A-induced hepatitis. At the same time, the induction of Con A-hepatitis is associated with the production of various cytokines such as IL-2, TNFα, IL-6, IL-4, and IL-10.

DISCLOSURE OF INVENTION

The present inventors have conducted an extensive research for many years in order to develop new therapeutics suitable for caspase inhibitor which has a unique structure over those known in the art. As a result the inventors have surprisingly discovered a novel isoxazoline derivative of formula (I) which has a different structure over the known inhibitors and has an excellent inhibitory activity against various substrates for caspases, and have completed the present invention It is therefore an object of the present invention to provide a novel isoxazoline compound of the formula (I), the pharmaceutically acceptable salts, esters and stereochemically isomeric forms thereof which are useful as a caspase inhibitor.

Another object of the present invention is to provide a process for preparing the compound of formula (I).

Further object of the present invention is to provide a caspase inhibitor which comprises an isoxazoline derivative of the formula (I), the pharmaceutically acceptable salts, esters and stereochemically isomeric forms thereof.

Still other object of the present invention is to provide a pharmaceutical composition for inhibiting caspases activity which comprises as the active ingredient a therapeutically effective amount of the isoxazoline derivative of formula (I) and pharmaceutically acceptable carrier.

Still further object of the present invention is to provide a pharmaceutical composition for preventing inflammation and apoptosis which comprises the isoxazoline derivative, pharmaceutically acceptable salts, esters and stereochemically isomeric forms thereof and the process for preparing the same.

Further objects and advantages of the invention will become apparent through reading the remainder of the specification.

The foregoing has outlined some of the more pertinent objects of the present invention These objects should be construed to be merely illustrative of some of the more pent features of the invention. Many other beneficial results can be obtained by applying the disclosed invention in a different manner or by modifying the invention within the scope of the disclosure. Accordingly, other objects and a more thorough understanding of the invention may be found by referring to the detailed description of the preferred embodiment in addition to the scope of the invention defined by the claims.

BEST MODE FOR CARRYING OUT THE INVENTION

Figure 1:
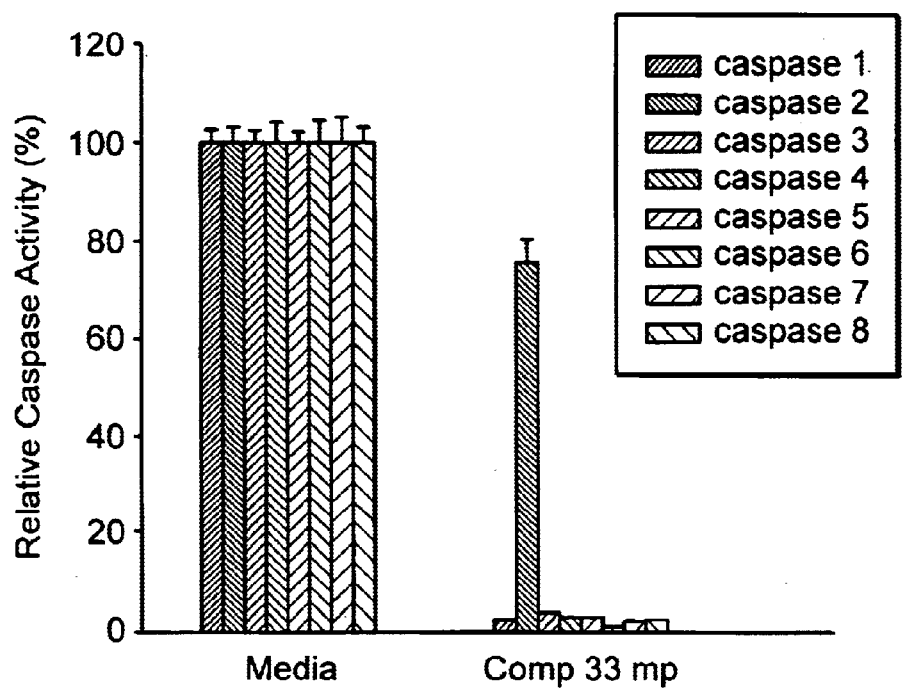
FIG. 1 represents a graph showing inhibition activity of the compound of the invention against recombinant caspase-1, -2, -3, -4, -6, -7, -8 and -9.

In advance of illustrating the present invention in detail some important terms are defined as follows:

a) Simple Alkyl Chain (hereinafter referred to as "SAC") is meant by a carbohydrate having $C_{1-8}$, and contains a branched isomeric form.

b) Simple CycloAlkyl Chain (hereinafter referred to as "SCAC" is meant by a cyclic compound having $C_{3-10}$.

c) Aryl group (hereinafter referred to as "Ar") represents benzene [1:2,3,4,5,6], naphthalene[1,2:1,2,3,4,5,6,7,8,], pyridine [2,3,4:2,3,4,5,6], indole[1,2,3,4,5,6,7:1,2,3,4,5, 6,7], quinoline[2,3,4,5,6,7,8:2,3,4,5,6,7,8], isoquinoline [1,3,4,5,6,7,8:1,3,4,5,6,7,8], furan[2,3:2,3,4,5], thiophene [2,3:2,3,4,5], pyrole[1,2,3:1,2,3,4,5], pyrimidine [2,4,5, 6:2,4,5,6], imidazole[1,2,4,5:1,2,4,5], benzofuran[2,3;2, 3,4,5,6,7], etc. in which the former digits within the bracket represents a position where the corresponding aryl group is connected to the inhibitor according to the present invention and the latter digits after the colon represents a position where the substituent Y defined later can be attached.

d) Side chain of amino acids represents the side groups which are attached to the chiral carbon of 20 natural amino acids.

Frequently referred terms are abbreviated as follows:

N-chlorosuccinimide: NCS

N-methylmorporline: NMM

N,N-dimethyl formamide: DMF 1-(3-dimethylaminopropyl)-3-ethylcarbodiimide: EDC 1-hydroxybenzotriazole hydrate: HOBt Trifluoroacetic acid: TFA t-butoxycarbonyl: Boc benzyloxycarbonyl: Cbz methyl: Me ethyl: Et equivalent: Eq or eq The term "stereochemically isomeric forms" as used in the foregoing and hereinafter defines all the possible isomeric forms which the derivative of formula (1) may possess. Unless otherwise mentioned or indicated, the chemical designation of compounds denotes a mixture of all possible stereochemically isomeric forms, said mixture containing all diastereomers of the basic molecular structure. Stereochemically isomeric forms of the derivatives of the formula (1) are intended to be embraced within the scope of this invention.

The pharmaceutically acceptable salts as used in the foregoing and hereinafter comprises the therapeutically active non-toxic salt forms which can form the derivative of formula (1).

Hereinafter, the invention will be illustrated in more detail.

In one aspect, the present invention provides a novel isoxazoline derivative of the formula (I), the pharmaceutically acceptable salts, esters and stereochemically isomeric forms thereof.

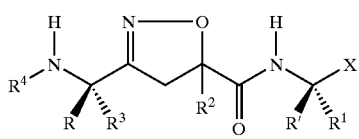

(I)

In the compound of formula (I), the substitutes are defined as follows:

R and R' each independently represents hydrogen, simple alkyl chain (—SAC), simple cycloalkyl (—SCAC), aromatic (—Ar), or simple alkyl chain substituted with aromatic (—SAC—Ar); preferably represents hydrogen. Throughout the description of the specification, R' has the same meaning as R unless specifically defined.

$R^1$ represents —SAC, —SCAC, —Ar, or —SAC—Ar, or represents side chain of amino acids, or —$(CH_2)_n$COOZ (in which n is 1 or 2, and Z is hydrogen, —SAC, —Ar or —SCAC); preferably represents —$CH_2$COOH.

$R^3$ represents —SAC, —SCAC, —Ar, —SAC—Ar, or side chain of amino acids; preferably represents —CH$(CH_3)_2$, —$CH_2$COOH, —$(CH_2)_2CO_2H$, —$CH_2$C(=O)$NH_2$ or —$(CH_2)_2$C(=O)$NH_2$.

In a case where an adjacent position of $R^1$ or $R^3$ become a stereogenic center, both the stereoisomeric compounds are intended to be embraced within the scope of the present invention. Similarly, a case where two forms of compounds are co-exist (a mixture of diastereomeric compounds) is embraced within the scope of the invention. In addition, the cases where $R^1$ or $R^3$ are composed of carboxylic acids or bases with side chain residue of amino acids, their protected forms such as simple esters or pharmaceutically acceptable salt forms are also embraced within the scope of the compounds according to the invention.

$R^2$ represents —H, —SAC, —SCAC, —Ar, or —SAC—Ar, or resents side chain of amino acids, or represents —$(CH_2)_n(O)_mR^5$ (in which $R^5$=—SAC, —SCAC, —Ar, —SAC—Ar, n=0, 1 or 2; and m=0 or 1), or —$(CH_2)_n$OC(=O)$R^6$ (in which $R^6$=—SAC, —SCAC, —Ar, or —SAC—Ar, and n=1 or 2). Preferable $R^2$ represents $(CH_2)_n(O)_m$Ar' (in which n=0, 1, or 2; and m=0 or 1; Ar'=substituted phenyl or imidazole), methyl or hydrogen.

In a case where an adjacent position due to $R^2$ become a stereogenic center, both the stereoisomeric compounds are embraced within the context of the compounds of the present invention, Similarly, a case where two forms of compounds are co-exist (a mixture of diastereomeric compounds) is embraced within the category of the compounds according to the invention. In addition, the cases where $R^2$ are composed of carboxylic acids or bases with side chain residue of amino acid, their protected forms such as simple esters or pharmaceutically acceptable salt forms are also embraced within the scope of the compounds according to tie invention.

$R^4$ represents a) amino acid residue in which ① the carboxyl group attached to the chiral carbon of amino acid is bound to the amine group to form an amide bond, ② the chiral carbon of amino acid has either R or S configuration, ③ the amino group attached to the chiral carbon of amino acid is protected by formyl, acetyl, propyl, cyclopropylcarbonyl, butyl, methanesulfonyl, ethanesulfonyl, propanesulfonyl, butanesulfonyl methoxycarbonyl, ethoxycarbonyl, propyloxycarbonyl, butyloxycarbonyl, methylcarbamoyl, ethylcarbamoyl, propylcarbamoyl, butylcarbamoyl, dimethylcarbamoyl, dimethylcarbamoyl dipropylcarbamoyl, dibutylcarbamoyl or cyclopropylaminocarbonyl, or the amino group may be replaced with a hydrogen atom, and ④ the carboxyl group in the side chain may form an ester group with —SAC or —SCAC, b) —C(=O)$R^7$ (in which $R^7$=—SAC, —SCAC, —Ar, —SAC—Ar), —$CO_2R^8$ (in which $R^8$=hydrogen or $R^7$), —C(=O)$NR^8R^8$, —$SOR^7$, —$SO_2^7$, or —C(=O)CH=CH—Ar, c) —(C=O)—L—$CO_2R^8$, in which L represents a divalent (=capable of double substitution) linker selected from a group consisting of $C_{1-6}$ alkyl, $C_{3-8}$ cycloalkyl furan, thiophene, diazole (1,2 or 1,3), triazole (1,2,3 or 1,3,4), tetrazole, oxazole, isoxazole, thiazole, isothiazole, diazine (1,2 or 1,3 or 1,4), triazine, —Ph(—$R^9$)— (in which $R^9$=H, F, Cl, Br, I, CHO, OH, $OCH_3$, $CF_3$, $OCF_3$, CN, C(=O)Me), tetrahydrofuran, tetahydrothiophene, 1,4-dioxane, —CH=C($R^{10}$)— (in which $R^{10}$=H, methyl, ethyl), —CH=CHCH($R^{10}$)—, —CH($OR^{10}$)$CH_2$—, —$CH_2$C(=O)$CH_2$—, —C(=O)$CH_2CH_2$—.

In cases where $R^1$ and the adjacent R', and/or $R^3$ and the adjacent R are connected to each other to form a cyclic compound, $R^1$—R' or $R^3$—R together represents —$(CH_2)_n$—, —$(CH_2)_n$—O—$(CH_2)_m$—, or —$(CH_2)_n$—$NR^{13}$—$(CH_2)_m$— (in which n+m<9, $R^{13}$=—SAC, —SCAC, —Ar, —SAC—Ar, —C(=O)—SAC, —C(=O)—SCAC, —C(=O)—Ar, or —C(=O)—SAC—Ar);

X represents —CN, —CHO, —C(=O)$R^{14}$ (in which $R^{14}$=—SAC, —SCAC, —Ar, —SAC—Ar, or —$CHN_2$), —C(=O)$OR^{15}$ (in which $R^{15}$=—SAC, —SCAC, —Ar, or —SAC—Ar), —$CONR^{16}R^{17}$ (in which $R^{16}$ and $R^{17}$ each represents —H, —SAC, —O—SAC, —SCAC, —Ar, or —SAC—Ar), —C(=O)$CH_2$O(C=O)Ar" (in which Ar"=2,6-disubstituted phenyl with F, Cl, Br, I, or $CH_3$), —C(=O)$CH_2OR^{18}$ (in which $R^{18}$ represents —SAC, —SCAC, —Ar, or —SAC—Ar), or —C(=O)$CH_2$OC(=O)$R^{19}$ (in which $R^{19}$=—SAC, —SCAC, —Ar, or —SAC—Ar), or X represents —$COCH_2$—W, wherein W represents —$N_2$, —F, —Cl, —Br, —I, —$NR^{20}OR^{21}$ or —$SR^{22}$ (in which wherein $R^{20}$, $R^{21}$ and $R^{22}$ each independently represents —SAC, —SCAC, —Ar, or —SAC—Ar or $R^{20}$ and $R^{21}$ are connected to form a cyclic compound); or W represents

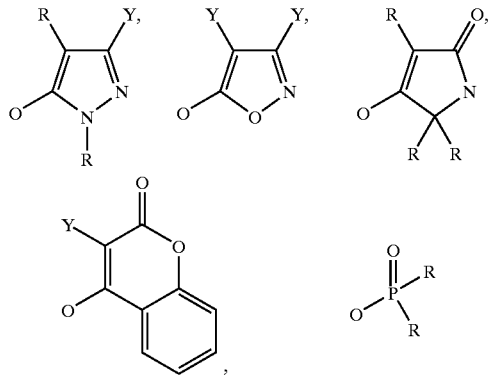

in which Y represents —OH, $OR^{23}$ (in which $R^{23}$=—SAC, or —SCAC), —C(=O)$R^{24}$ (in which $R^{24}$=—H —SAC, or —SCAC), —F, —Cl, —Br, —I, —CN, —NC, —$N_3$, —CO$_2$H, —CF$_3$, —CO$_2$R$^{25}$ (in which R$^{25}$=—SAC, or —SCAC), —C(=O)NHR$^{26}$ (in which R$^{26}$=—SAC, or —SCAC), and —C(=O)NR$^{27}$R$^{28}$ (in which R$^{27}$, R$^{28}$=—SAC, or —SCAC) and can be mono- or polysubstituted at its maximunm regardless of the order and the kinds.

Among the compound of formula (I), preferred are those in which R$^4$ represents —C(=O)(CH$_2$)$_p$COOZ (in which p is 1 to 4, and Z is hydrogen, —SAC, —Ar or —SCAC). Also preferred are those in which R$^1$ represents —(CH$_2$)$_n$COOZ (in which n is 1 or 2, and Z is hydrogen, —SAC, —Ar or —SCAC).

Among the compound of formula (I), more preferred are those in which a) R and R' represent hydrogen, b) R$^1$ represents —CH$_2$COOH, —CH$_2$COOCH$_3$, or CH$_2$COOCH$_2$CH$_3$, c) R$^2$ represents —(CH$_2$)$_n$(O)$_m$R$^5$ (in which R$^5$=—SAC, —SCAC, —Ar, —SAC—Ar; n=0, 1 or 2; and m=0 or 1), SAC, Ar, or Hydrogen, d) R$^3$ represents —CH(CH$_3$)$_2$, —CH$_2$COOH, —(CH$_2$)$_2$ CO$_2$H, —CH$_2$C(O)NH$_2$ or —(CH$_2$)$_2$C(O)NH$_2$, e) R$^4$ represents —C(=O)(O)$_n$R$^{29}$ (in which n=0, 1; R$^{29}$=—Ar or —SAC—Ar), —SO$_2$R$^{30}$ (in which R$^{30}$=—Ar or —SAC—Ar), or —C(=O)NHR$^{31}$ (in which R$^{31}$=—Ar, or —SAC—Ar), or f) X represents —C(=O)CHN$_2$, —C(=O)CH$_2$Br, —C(=O)CH$_2$Cl, —C(=O)CH$_2$OPh or —C(=O) CH$_2$OC(=O)Ar" (in which Ar"=2,6-dichlorophenyl, 2,6-difluorophenyl or 2,6-dimethylphenyl).

Most preferred compounds are selected from the group consisting of the following:

(3S)-3-{3-[(1S)-1-phenylmethyloxycarbonylamino-2-methyl-propyl]-4,5-dihydro-isoxazole-5-carbonylamino}-4-keto-pentanoic acid;

(3S)-3-{3-[(1S)-1-phenylmethyloxycarbonylamino-2-methyl-propyl]-5-phenoxymethyl-4,5-dihydro-isoxazole-5-carbonyl-amino}-4-keto-pentanoic acid;

(2S)-2-{3-[(1S)-1-phenylmethyloxycarbonylamino-2-methyl-propyl]-5-phenoxymethyl-4,5-dihydro-isoxazole-5-carbonyl-amino}-succinic acid 1(N-methyl-N-methoxy)-amide;

(3S)-3-{3-[(1S)-1-phenylmethyloxycarbonylamino-2-methyl-propyl]-4,5-dihydro-isoxazole-5-carbonylamino}-4-keto-5-diazo-pentanoic acid;

(3S)-3-{3-[(1S)-1-phenylmethyloxycarbonylamino-2-methyl-propyl]-4,5-dihydro-isoxazole-5cabonylamino}-4-keto-5-bromo-pentanoic acid;

(3S)-3-{3-[(1S)-1-phenylmethyloxycarbonylamino-2-methyl-propyl]-4,5-dihydro-isoxazole-5-carbonylamino}-4-keto-5-(2,6-dichlorobenzoyloxy)-pentanoic acid;

(3S)-3-{3-[(1S)-1-(naphthalene-1-carbonylamino)-2-methyl-propyl]-5-phenoxymethyl-4,5-dihydro-isoxazole-5-carbonylamino}-4-keto-5-phenoxy-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-phenoxy-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-diazo-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-bromo-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-(2,6-dichlorobenzoyloxy)pentanoic acid;

(3S)-3-{3-[(1S)-1-(naphthalene-2-(carbonylamino)-2-methyl-propyl]-5-phenylmethyl-4,5-dihydro-isoxazole-5-carbonylamino}-4-keto-5diazo-pentanoic acid(LP and MP);

(3S)-3-{3-[(1S)-1-(naphthalene-2-carbonylamino)-2-methyl-propyl]-5-phenylmethyl-4,5-dihydro-isoxazole-5-carbonylamino}-4-keto-5-bromo-pentanoic acid(LP and MP);

(3S)-3-{3-[(1S)-1-(naphthalene-2-carbonylamino}-2-methyl-propyl]-5-phenylmethyl-4,5-dihydro-isoxazole-5-carbonylamino}-4-keto-5-(2,6-dichlorobenzoyloxy)-pentanoic acid(LP and MP);

(3S)-3-{3-[(1S)-1-(naphthalene-2-carbonylamino)-3-carboxyl-propyl]-5-methyl-4,5-dihydro-isoxazole-5-carbonylamino}-4-keto-5-phenoxy-pentanoic acid;

(3S)-3-{3-[(1S)-1-(quinoline-2-yl-carbonylamino)-2-methyl-propyl]-5-phenoxymethyl-4,5-dihydro-isoxazole-5-carbonylamino}-4-keto-pentanoic acid;

(3S)-3-{3-[(1S)-1-(naphthalene-2-sulfonylamino)-2-methyl-propyl]-5-phenoxymethyl-4,5-dihydro-isoxazole-5-carbonylamino}-4-keto-5-phenoxy-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-(2-naphthyloxy)-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4keto-5-(1-naphthyloxy)-pentanoic acid;

(3S)-3-{3-[(1S)-1-(2S)-2-acetylamino-succinoylamino)-3-carboxy-propyl]-5-methyl-4,5-dihydro-isoxazole-5-carbonylamino}-4-keto-5-phenoxy-pentanoic acid;

(3S)-3-{3-[(1S)-1-(naphthalene-2-carbonylamino)-2-methyl-propyl]-4,5-dihydro-isoxazole-5-carbonylamino}-4-keto-5-(2-naphthyloxy)-pentanoic acid;

(3S)-3-{3-[2-methyl-(1S)-1-(2-naphthalenecarbonylamino)-propyl]-4,5-dihydro-isoxazole-5-carbonylamino}-4-keto-5-phenoxy-pentanoic acid (diastereomeric mixture);

(3S)-3-{3-[2-methyl-(1S)-1-(phenylmethyloxycarbonylamino)-propyl]-5-phenylmethyl-4,5-dihydro-isoxazole-5-carbonylamino}-4-keto-5-diazo-pentanoic acid;

(3S)-3-{3-[2-methyl-(1S)-1-(phenylmethyloxycarbonylamino)-propyl]-5-phenylmethyl-4,5dihydro-isoxazole-5-carbonylamino}-4-keto-5-bromo-pentanoic acid;

(3S)-3-{3-[2-methyl-(1S)-1-(phenylmethyloxycarbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(phenylethylcarbonylamino)-propyl]-5-phenylmethyl-4,5-dihydro-isoxazole-5-carbonylamino}-4-keto-5-diazo-pentanoic acid;

(3S)-3-{3-[2-methyl-(1S)-1-(phenylethylcarbonylamino)-propyl]-5-phenylmethyl-4,5-dihydro-isoxazole-5-carbonylamino}-4-keto-5-bromo-pentanoic acid;

(3S)-3-{3-[2-methyl-(1S)-1-(phenylethylcarbonylamino)-propyl]-5-phenylmethyl-4,5-dihydro-isoxazole-5-carbonylamino}-4-keto-5-(2,6dichlorobenzoyloxy)-pentanoic acid;

(3S)-3-{3-[2-methyl-(1S)-1-(1-naphthalenecarbonylamino)-propyl]-5-phenylmethyl-4,5dihydro-isoxazole-5-carbonylamino}-4-keto-5-diazo-pentanoic acid;

(3S)-3-{3-[2-methyl-(1S)-1-(1-naphthalenecarbonylamino)-propyl]-5-phenylmethyl-4,5-dihydro-isoxazole-5-carbonylamino}-4-keto-5-bromo-pentanoic acid;

(3S)-3-{3-[2-methyl-(1S)-1-(1-naphthalenecarbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(1-naphtalenesulfonylamino)-propyl]-5-phenylmethyl-4,5-dihydro-isoxazole-5-carbonylamino}-4-keto-5-diazo-pentanoic acid (diastereomeric mixture);

(3S)-3-{3-[2-methyl-(1S)-1-(1-naphtalenesulfonylamino)-propyl]-5-phenylmethyl-4,5-dihydro-isoxazole-5-carbonylamino}-4-keto-5-bromo-pentanoic acid (diastereomeric mixture);

(3S)-3-{3-[2-methyl-(1S)-1-(1-naphtalenesulfonylamino)-propyl]-5-phenylmethyl-4,5-dihydro-isoxazole-5-carbonylamino}-4-keto-5-(2,6-dichlorobenzoyloxy)-pentanoic acid (diastereomeric mixture);

(3S)-3-{3-[2-methyl-(1S)-1-((3-indolyl)ethylcarbonylamino)-propyl]5-phenylmetyl-4,5-dihydro-isoxazole-5-carbonylamino}-4-keto-5-diazo-pentanoic acid;

(3S)-3-{3-[2-methyl-(1S)-1-((3-indolyl)ethylcarbonylamino)-propyl]-5-phenylmethyl-4,5-dihydro-isoxazole-5-carbonylamino}-4-keto-5-bromo-pentanoic acid;

(3S)-3-{3-[2-methyl-(1S)-1-((3-indolyl)ethylcarbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-((3-indolyl)methylcarbonylamino-propyl]-5-phenylmethyl-4,5-dihydro-isoxazole-5-carbonylamino}-4-keto-5-diazo-pentanoic acid;

(3S)-3-{3-[2-methyl-(1S)-1-((3-indolyl)methylcarbonylamino)-propyl]-5-phenylmethyl-4,5-dihydro-isoxazole-5-carbonylamino}-4-keto-5-bromo-pentanoic acid;

(3S)-3-{3-[2-methyl-(1S)-1-((3-indolyl)methylcarbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(cinnamoylamino)-propyl]-5-phenylmethyl-4,5-dihydro-isoxazole-5-carbonylamino}-4-keto-5-diazo-pentanoic acid;

(3S)-3-{3-[2-methyl-(1S)-1-(cinnamoylamino)-propyl]-5-phenylmethyl-4,5-dihydro-isoxazole-5-carbonylamino}-4-keto-5-bromo-pentanoic acid;

(3S)-3-{3-[2-methyl-(1S)-1-(cinnamoylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(phenylmethylsulfonylamino)-propyl]-5-phenylmethyl-4,5-dihydro-isoxazole-5-carbonylamino}-4-keto-5-diazo-pentanoic acid;

(3S)-3-{3-[2-methyl-(1S)-1-(phenylmethylsulfonylamino)-propyl]-5-phenylmethyl-4,5-dihydro-isoxazole-5-carbonylamino}-4-keto-5-bromo-pentanoic acid;

(3S)-3-{3-[2-methyl-(1S)-1-(phenylmethylsulfonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(quinoline-2-yl-carbonylamino)-propyl]-4,5-dihydro-isoxazole-5-carbonylamino}-4-keto-5-diazo-pentanoic acid;

(3S)-3-{3-[2-methyl-(1S)-1-(quinoline-2-yl-carbonylamino)-propyl]-4,5-dihydro-isoxazole-5-carbonylamino}-4-keto-5-bromo-pentanoic acid;

(3S)-3-{3-[2-methyl-(1S)-1-(quinoline-2-yl-carbonylamino)-propyl]-4,5-dihydro-isoxazole-5-carbonylamino}-4-keto-5-(2,6-dichlorobenzoyloxy)-pentanoic acid;

(3S)-3-{3-[2-methyl-(1S)-1-(quinoline-2-yl-carbonylamino)-propyl]-4,5-dihydro-isoxazole-5-carbonylamino}-4-keto-5-phenoxy-pentanoic acid;

(3S)-3-{3-[2-methyl-(1S)-1-(quinoline-2-yl-carbonylamino)-propyl]-5-phenylmethyl-4,5-dihydro-isoxazole-5-carbonylamino}-4-keto-5-diazo-pentanoic acid;

(3S)-3-{3-[2-methyl-(1S)-1-(quinoline-2-yl-carbonylamino)-propyl]-5-phenylmethyl-4,5-dihydro-isoxazole-5-carbonylamino}-4-keto-5-bromo-pentanoic acid;

(3S)-3-{3-[2-methyl-(1S)-1-(quinoline-2-yl-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(quinoline-2-yl-carbonylamino)-propyl]-5-phenylmethyl-4,5-dihydro-isoxazole-5-carbonylamino}-4-keto-5-phenoxy-pentanoic acid;

(3S)-3-{3-[2-methyl-(1S)-1-(quinoline-2-yl-carbonylamino)-propyl]-5-(1-imidazolyl-methyl)-4,5-dihydro-isoxazole-5-carbonylamino}-4-keto-5-phenoxy-pentanoic acid;

(3S)-3-{3-[2-methyl-(1S)-1-(2-naphthalenecarbonylamino)-propyl]-4,5-dihydro-isoxazole-5-carbonylamino}-4-keto-pentanoic acid;

(3S)-3-{3-[(1S)-1-(succinoylamino)-3-carboxy-propyl]-5-methyl-4,5-dihydro-isoxazole-5-carbonylamino}-4-keto-5-phenoxy-pentanoic acid;

(3S)-3-{3-[2-methyl-(1S)-1-(succinoylamino)-propyl]-5-methyl-4,5-dihydro-isoxazole-5-carbonylamino}-4-keto-5-phenoxy-pentanoic acid;

(3S)-3-{3-[2-methyl-(1S)-1-(1-naphthalenecarbonylamino)-propyl]-5-phenylmethyl-4,5-dihydro-isoxazole-5-carbonylamino}-4-keto-5-(1-piperidinyl)-pentanoic acid;

(3S)-3-{3-[2-methyl-(1S)-1-(isoquinoline-1-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(isoquinoline-3-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(quinoline-4-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(benzofuran-2-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(naphthalene-1-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(quinoline-3-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(naphthalene-1-carbonylamino)-propyl]-5-phenylmethyl-4,5-dihydro-isoxazole-5-carbonylamino}-4-keto-5-(2,6-dimethylbenzoyloxy)-pentanoic acid[diastereomeric mixture];

(3S)-3-{3-[2-methyl-(1S)-1-(quinoline-8-carbonylamino)-propyl]-5-phenylmethyl-4,5-dihydro-isoxazole-5-carbonylamino}-4-keto-5-(2,6-dichlorobenzoyloxy)-pentanoic acid [diastereomeric mixture];

(3S)-3-{3-[2-methyl-(1S)-1-(indole-2-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(indole-3-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(naphthalene-1-carbonylamino)-propyl]-5-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(benzofuran-2-carbonylamino)-propyl]-5-methyl-4,5-dihydro-isoxazole-5-cabonylamino}-4-keto-5-(2,6-dichlorobenzoyloxy)-pentanoic acid;

(3S)-3-{3-[3-carboxy-(1S)-1-(succinoylamino)-propyl]-5-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-propyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-methyl-4,5-dihydro-isoxazole-5-carbonylamino}-4-keto-5-(N-piperidine)-pentanoic acid[diastereomeric mixture];

(3S)-3-{3-[2-methyl-(1S)-1-(succinoylamino)-propyl]-5-methyl-4,5-dihydro-isoxazole-5-cabonylamino}-4-keto-5-(N-pyrrolidine)-pentanoic acid [diastereomeric mixture];

(3S)-3-{3-[2-methyl-(1S)-1-(succinoylamino)-propyl]-5-butyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-methyl-4,5-dihydro-isoxazole-5-carbonylamino}-4-keto-5-(2-naphthyloxy)-pentanoic acid;

(3S)-3-{3-[2-methyl-(1S)-1-(succinoylamino)-propyl]-5-propyl-4,5-dihydro-isoxazole-5-carbonylamino}-4-keto-5-phenoxy-pentanoic acid [diastereomeric mixture];

(3S)-3-{3-[2-methyl-(1S)-1-succinoylamino)-propyl]-5-hydroxymethyl-4,5-dihydro-isoxazole-5-carbonylamino}-4-keto-5-(2,6-dichlorobenzoyloxy)-pentanoic acid [diastereomeric mixture];

(3S)-3-{3-[2-methyl-(1S)-1-(succinoylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-methoxymethyl-4,5-dihydro-isoxazole-5-carbonylamino}-4-keto-5-(2,6-dichlorobenzoyloxy)-pentanoic acid [diastereomeric mixture];

(3S)-3-{3-[2-methyl-(1S)-1-(succinoylamino)-propyl]-5-n-pentyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-ethyl-4,5-dihydro-isoxazole-5-carbonylamino}-4-keto-5-(2,6-dichlorobenzoyloxy)-pentanoic acid;

(3S)-3-{3-[2-methyl-(1S)-1-(glutaroylamino)-propyl]-5-methyl-4,5-dihydro-isoxazole-5-carbonylamino}-4-keto-5-(2,6-dichlorobenzoyloxy)-pentanoic acid; and (3S)-3-{3-[2-methyl-(1S)-1-(phenylmethyloxycarbonylamino)-propyl]-4,5-dihydro-isoxazole-5-carbonylamino}-4-keto-pentanoic acid methyl ester.

In another aspect, the present invention provides a process for preparing a compound of formula (I).

Hereinafter, a process for preparing the isoxazoline derivatives of formula (I) according to the present invention will be explained with respect to Reaction Schemes 1 and 2. It should be understood that the reaction schemes generally illustrate the specific process used in the present invention, but any modification of the unit operations may be made without departure of the spirit of the invention Therefore, the present invention should not be limited to the following preferred embodiments.

In the first step, amino protected amino acid (II) (commercially available from Novabiochem) is reduced to give N-protected amino alcohol (III) which is then oxidized to give N-protected amino aldehyde (IV).

N-protected amino aldehyde (IV) is reacted with hydroxylamine-hydrochloride and sodium carbonate in a mixed solution of an alcohol and water to give an oxime (V) (syn- and anti-oxime). The resulting oxime derivative (V) is treated with NCS (N-chlorosuccinimide) in an aqueous solution of dimethylformamide to give hydroxamoyl chloride (VI). As the representative substituents used in the synthesis of hydroxamoyl chloride, the following groups may be exemplified: $P_1$ represents Cbz, t-Boc, Fmoc, Teoc (trimethylsilyl-ethyloxycarbonyl), etc.; R represents H and $R^3$ represents —$CH_2CH_2CO_2Bu(t)$, —$CH_2CO_2Me$, —$CH_2CO_2Bu(t)$, -isopropyl, phenylmethyl and the like.

Reaction Scheme 1

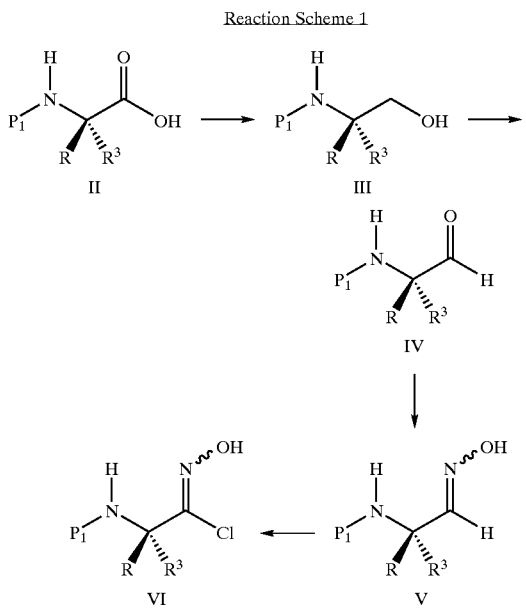

In the above Reaction Scheme 1, the following combinations of a) to g) for the commercially available compounds (II) to (VI) may be synthesized.
a) $P_1$=Cbz, R=H, $R^3$=i-Pr
b) $P_1$=t-Boc, R=H, $R^3$=i-Pr
c) $P_1$=Fmoc, R=H, $R^3$=$CH_2CH_2CO_2Bu(t)$
d) $P_1$=t-Boc, R=H, $R^3$=$CH_2CO_2Me$
e) $P_1$=Cbz, R=H, $R^3$=$CH_2CO_2Bu(t)$
f) $P_1$=Fmoc, R=H, $R^3$=$CH_2CO_2Bu(t)$
g) $P_1$=Boc or Cbz, R=H, $R^3$=$CH_2Ph$ Reaction Scheme 2

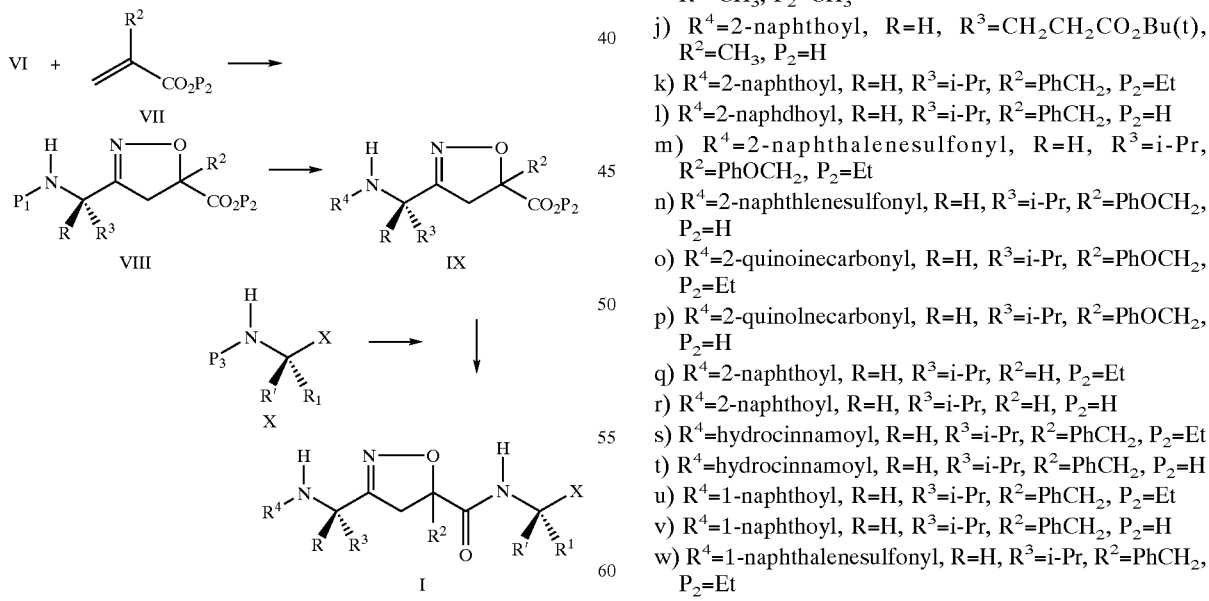

In the second step, the hydroxamoyl chloride (VI) thus obtained is then reacted with acrylate derivative (VII) to give isoxazoline derivative (VIII). If necessary, isoxazoline derivative (VIII) may be synthesized directly from the oxime derivative (V).

If a compound having the protecting group $P_1$can be used as the inhibitor (for example, $P_1$is a Cbz group), the isoxazoline derivative (VIII) is directly reacted with the compound (X) to give a compound of formula (I), and there is need to convert the protecting group $P_1$into other substituent, $P_1$ is removed and $R^4$ is introduced thereinto.

In the above Reaction Scheme 2, the following combination of substituents may be synthesized.
In the compound (VIII),
a) $P_1$=Cbz, R=H, $R^3$=i-Pr, $R^2$=H, $P_2$=Et
b) $P_1$=Cbz, R=H, $R^3$=i-Pr, $R^2$=H, $P_2$=H
c) $P_1$=Cbz, R=H, $R^3$=i-Pr, $R^2$=$CH_2OPh$, $P_2$=Et
d) $P_1$=Cbz, R=H, $R^3$=i-Pr, $R^2$=$CH_2OPh$, $P_2$=H
e) $P_1$=Fmoc, R=H, $R^3$=$CH_2CH_2CO_2Bu(t)$, $R^2$=$CH_3$, $P_2$=$CH_3$(or Et)
f) $P_1$=Teoc, R=H, $R^3$=i-Pr, $R^2$=$CH_3$, $P_2$=H
g) $P_1$=t-Boc, R=H, $R^3$=i-Pr, $R^2$=$PhCH_2$, $P_2$=Et
h) $P_1$=t-Boc, R=H, $R^3$=i-Pr, $R^2$=$PhOCH_2$, $P_2$=Et
i) $P_1$=t-Boc, R=H, $R^3$=i-Pr, $R^2$=1-naphthyl, $P_2$=Et
j) $P_1$=t-Boc, R=H, $R^3$=i-Pr, $R^2$=2-naphthyl, $P_2$=Et
k) $P_1$=t-Boc, R=H, $R^3$=i-Pr, $R^2$=phenyl, $P_2$=Et
l) $P_1$=t-Boc, R=H, $R^3$=i-Pr, $R^2$=4-bromophenyl, $P_2$=Et
m) $P_1$=t-Boc, R=H, $R^3$=i-Pr, $R^2$=$AcOCH_2$, $P_2$=Et
In the compound (IX),
a) $R^4$=Cbz, R=H, $R^3$=i-Pr, $R^2$=H, $P_2$=Et
b) $R^4$=Cbz, R=H, $R^3$=i-Pr, $R^2$=H, $P_2$=H
c) $R^4$=Cbz, R=H, $R^3$=i-Pr, $R^2$=$CH_2OPh$, $P_2$=Et
d) $R^4$=Cbz, R=H, $R^3$=i-Pr, $R^2$=$CH_2OPh$, $P_2$=H
e) $R^4$=1-naphthoyl, R=H, $R^3$=i-Pr, $R^2$=$CH_2OPh$, $P_2$=Et
f) $R^4$=1-naphthoyl, R=H, $R^3$=i-Pr, $R^2$=$CH_2OPh$, $P_2$=H
g) $R^4$=2-naphthoyl, R=H, $R^3$=i-Pr, $R^2$=$CH_2OPH$, $P_2$=Et
h) $R^4$=2-naphthoyl, R=H, $R^3$=i-Pr, $R^2$=$CH_2OPh$, $P_2$=H
i) $R^4$=2-naphthoyl, R=H, $R^3$=$CH_2CH_2CO_2Bu(t)$, $R^2$=$CH_3$, $P_2$=$CH_3$
j) $R^4$=2-naphthoyl, R=H, $R^3$=$CH_2CH_2CO_2Bu(t)$, $R^2$=$CH_3$, $P_2$=H
k) $R^4$=2-naphthoyl, R=H, $R^3$=i-Pr, $R^2$=$PhCH_2$, $P_2$=Et
l) $R^4$=2-naphdhoyl, R=H, $R^3$=i-Pr, $R^2$=$PhCH_2$, $P_2$=H
m) $R^4$=2-naphthalenesulfonyl, R=H, $R^3$=i-Pr, $R^2$=$PhOCH_2$, $P_2$=Et
n) $R^4$=2-naphthlenesulfonyl, R=H, $R^3$=i-Pr, $R^2$=$PhOCH_2$, $P_2$=H
o) $R^4$=2-quinoinecarbonyl, R=H, $R^3$=i-Pr, $R^2$=$PhOCH_2$, $P_2$=Et
p) $R^4$=2-quinolnecarbonyl, R=H, $R^3$=i-Pr, $R^2$=$PhOCH_2$, $P_2$=H
q) $R^4$=2-naphthoyl, R=H, $R^3$=i-Pr, $R^2$=H, $P_2$=Et
r) $R^4$=2-naphthoyl, R=H, $R^3$=i-Pr, $R^2$=H, $P_2$=H
s) $R^4$=hydrocinnamoyl, R=H, $R^3$=i-Pr, $R^2$=$PhCH_2$, $P_2$=Et
t) $R^4$=hydrocinnamoyl, R=H, $R^3$=i-Pr, $R^2$=$PhCH_2$, $P_2$=H
u) $R^4$=1-naphthoyl, R=H, $R^3$=i-Pr, $R^2$=$PhCH_2$, $P_2$=Et
v) $R^4$=1-naphthoyl, R=H, $R^3$=i-Pr, $R^2$=$PhCH_2$, $P_2$=H
w) $R^4$=1-naphthalenesulfonyl, R=H, $R^3$=i-Pr, $R^2$=$PhCH_2$, $P_2$=Et
x) $R^4$=1-naphthalenesulfonyl, R=H, $R^3$=i-Pr, $R^2$=$PhCH_2$, $P_2$=H
y) $R^4$=3-indoleacetyl, R=H, $R^3$=i-Pr, $R^2$=$PhCH_2$, $P_2$=Et
z) $R^4$=3-indoleacetyl R=H, $R^3$=i-Pr, $R^2$=$PhCH_2$, $P_2$=H
aa) $R^4$=3-indolepropionyl, R=H, $R^3$=i-Pr, $R^2$=$PhCH_2$, $P_2$=Et ab) $R^4$=3-indolepropionyl, R=H, $R^3$=i-Pr, $R^2$=PhCH$_2$, P$_2$=H
ac) $R^4$=trans-cinnamoyl, R=H, $R^3$=i-Pr, $R^2$=PhCH$_2$, P$_2$=Et
ad) $R^4$=trans-cinnamoyl, R=H, $R^3$=i-Pr, $R^2$=PhCH$_2$, P$_2$=H
ae) $R^4$=phenylmethylsulfonyl, R=H, $R^3$=i-Pr, $R^2$=PhCH$_2$, P$_2$=Et
af) $R^4$=phenylmethylsulfonyl, R=H, $R^3$=i-Pr, $R^2$=PhCH$_2$, P$_2$=H
ag) $R^4$=2-quilnolinecarbonyl, R=H, $R^3$=i-Pr, $R^2$=H, P$_2$=Et
ah) $R^4$=2-quilnolinecarbonyl, R=H, $R^3$=i-Pr, $R^2$=H, P$_2$=H
ai) $R^4$=2-quilnolinecarbonyl, R=H, $R^3$=i-Pr, $R^1$=PhCH$_2$, P$_2$=Et
aj) $R^4$=2-quinolinecarbonyl, R=H, $R^3$=i-Pr, $R^2$=PhCH$_2$, P$_2$=H
ak) $R^4$=2-quinolinecarbonyl, R=H, $R^3$=i-Pr, $R^2$=1-imidazolyl, P$_2$=Et
al) $R^4$=1-quolinecarbonyl, R=H, $R^3$=i-Pr, $R^2$=1-imidazolyl, P$_2$=H
am) $R^4$=COCH$_2$CH$_2$CO$_2$Bu(t), R=H, $R^3$=CH$_2$CH$_2$CO$_2$Bu(t), $R^2$=CH$_3$, P$_2$=CH$_3$
an) $R^4$=COCH$_2$CH$_2$CO$_2$Bu(t), R=H, $R^3$=CH$_2$CH$_2$CO$_2$Bu(t), $R^2$=CH$_3$, P$_2$=H
ao) $R^4$=COCH$_2$CH$_2$CO$_2$Bu(t), R=H, $R^3$=i-Pr, $R^2$=CH$_3$, P$_2$=CH$_3$
ap) $R^4$=COCH$_2$CH$_2$CO$_2$Bu(t), R=H, $R^3$=i-Pr, $R^2$=CH$_3$, P$_2$=H In the compound (X),
a) P$_3$=Cbz, R=H, $R^1$=CH$_2$CO$_2$Bu(t), X=CO$_2$Me
b) P$_3$=HCl+H, R=H, $R^1$=CH$_2$CO$_2$Bu(t), X=CO$_2$Me
c) P$_3$=Cbz, R=H, $R^1$=CH$_2$CO$_2$Bu(t), X=COCH$_2$N$_2$
d) P$_3$=Cbz, R=H, $R^1$=CH$_2$CO$_2$Bu(t), X=COCH$_2$Br
e) P$_3$=Cbz, R=H, $R^1$=CH$_2$CO$_2$Bu(t), X=COCH$_2$OPh
f) P$_3$Cbz, R=H, $R^1$=CH$_2$C$_2$Bu(t), X=CH(OH)CH$_2$OPh
g) P$_3$=H R=H, $R^1$=CH$_2$CO$_2$Bu(t), X=CH(OH)CH$_2$OPh
h) P$_3$=Cbz, R=H, $R^1$=CH$_2$CO$_2$Bu(t), X=CH(OH)CH$_2$OC(O)Ph(2,6-dichloro)
i) P$_3$=H, R=H, $R^1$=CH$_2$OBu(t), X=CH(OH)CH$_2$OC(O)Ph(2,6-dichloro)
j) P$_3$=Cbz, R=H, $R^1$=CH$_2$CO$_2$Bu(t), X=CONMe(OMe)
k) P$_3$=H, R=H, $R^1$=CH$_2$CO$_2$Bu(t), X=CONMe(OMe)
l) P$_3$=Cbz, R=H, $R^1$=CH$_2$COBu(t), X=CH(OH)CH$_2$O-(1-naphthyl)
m) P$_3$=H, R=H, $R^1$=CH$_2$CO$_2$Bu(t), X=CH(OH)CH$_2$O-(1-naphthyl)

In the compound (I),
a) $R^4$=2-naphthoyl, R=H, $R^3$=i-Pr, $R^2$=PhOCH$_2$, $R^1$=CH$_2$CO$_2$Bu(t), X=CO$_2$H
b) $R^4$=2-naphthoyl, R=H, $R^3$=i-pr, $R^2$=PhOCH$_2$, $R^1$=CH$_2$CO$_2$Bu(t), X=C(=O)CH$_2$N$_2$
c) $R^4$=2-naphthoyl, R=H, $R^3$=i-Pr, $R^2$=PhOCH$_2$, $R^1$=CH$_2$CO$_2$BU(t), X=C(=O)CH$_2$Br
d) $R^4$=2-naphthoyl, R=H, $R^3$=i-Pr, $R^2$=PhOCH$_2$, $R^1$=CH$_2$CO$_2$Bu(t), X=C(=O)CH$_2$OPh
e) $R^4$=2-naphthoyl, R=H, $R^3$=i-Pr, $R^2$=PhOCH$_2$, $R^1$=CH$_2$CO$_2$Bu(t), X=C(=O)CH$_2$OC(=O)Ph(2,6-dichloro)
f) $R^4$=2-naphthoyl, R=H, $R^3$=i-Pr, $R^2$=PhOCH$_2$, $R^1$=CH$_2$CO$_2$Bu(t), X=2-naphthyloxymethylcarbonyl
g) $R^4$=2-naphthoyl R=H, $R^3$=i-Pr, $R^2$=PhOCH$_2$, $R^1$=CH$_2$CO$_2$Bu(t), X=1-naphthyloxymethylcarbonyl
h) $R^4$=2-naphthoyl, R=H, $R^3$=i-Pr, $R^2$=PhOCH$_2$, $R^1$=CH$_2$CO$_2$Bu(t), X=CH(OH)CH$_2$OPh
i) $R^4$=1-naphthoyl, R=H, $R^3$=i-Pr, $R^2$=PhOCH$_2$, $R^1$=CH$_2$CO$_2$Bu(t), X=C(=O)CH$_2$OPh
j) $R^4$=2-naphthalenesulfonyl, R=H, $R^3$=i-Pr, $R^2$=PhOCH$_2$, $R^1$=CH$_2$CO$_2$Bu(t), X=CH(OH)CH$_2$OPh
k) $R^4$=2-naphthalenesulfonyl, R=H, $R^3$=i-Pr, $R^2$=PhOCH$_2$, $R^1$=CH$_2$CO$_2$Bu(t), X=C(=O)CH$_2$OPh
l) $R^4$=2-quinolinecarbonyl, R=H, $R^3$=i-Pr, $R^2$=PhOCH$_2$, $R^1$=CH$_2$CO$_2$Bu(t), X=CH(OH)CH$_2$OPh
m) $R^4$=2-quinolinecarbonyl, R=H, $R^3$=i-Pr, $R^2$=PhOCH$_2$, $R^1$=CH$_2$CO$_2$Bu(t), X=CH(OH)CH$_2$OPh
n) $R^4$=2-naphthoyl, R=H, $R^3$=i-Pr, $R^2$=PhCH$_2$, $R^1$=CH$_2$CO$_2$Bu(t), X=C(=O)CH$_2$N$_2$
o) $R^4$=2-naphthoyl, R=H, $R^3$=i-Pr, $R^2$=PhCH$_2$, $R^1$=CH$_2$CO$_2$Bu(t), X=C(=O)CH$_2$Br
p) $R^4$=2-naphthoyl, R=H, $R^3$=i-Pr, $R^2$=PhCH$_2$, $R^1$=CH$_2$CO$_2$Bu(t), X=C(=O)CH$_2$OPh
q) $R^4$=2-naphthoyl, R=H, $R^3$=i-Pr, $R^2$=PhCH$_2$, $R^1$=CH$_2$CO$_2$Bu(t), X=C(=O)CH$_2$OC(=O)—Ph-2,6-dichloro)
r) $R^4$=N-acetyl-β-t-butyl aspartyl, R=H, $R^3$=CH$_2$CH$_2$CO$_2$Bu(t), $R^2$=CH$_3$, $R^1$=CH$_2$CO$_2$Bu(t), X=CH(OH)CH$_2$OPh
s) $R^4$=N-acetyl-β-t-butyl aspartyl, R=H, $R^3$=CH$_2$CH$_2$CO$_2$Bu(t), $R^2$=CH$_3$, $R^1$=CH$_2$CO$_2$Bu(t), X=C(=O)CH$_2$OPh
t) $R^4$=Cbz, R=H, $R^3$=i-Pr, $R^2$=H, $R^1$=CH$_2$CO$_2$Bu(t), X=C(=O)NMe(OMe)
u) $R^4$=Cbz, R=H, $R^3$=i-Pr, $R^2$=H, $R^1$=CH$_2$CO$_2$Bu(t), X=C(=O)CH$_3$
v) $R^4$=Cbz, R=H, $R^3$=i-Pr, $R^2$=PhOCH$_2$, $R^1$=CH$_2$CO$_2$Bu(t), X=CO$_2$CH$_3$
w) $R^4$=Cbz, R=H, $R^3$=i-Pr, $R^2$=PhOCH$_2$, $R^1$=CH$_2$CO$_2$Bu(t), X=CO$_2$H
x) $R^4$=Cbz, R=H, $R^3$=i-Pr, $R^2$=PhOCH$_2$, $R^1$=CH$_2$CO$_2$Bu(t), X=C(=O)CH$_2$N$_2$
y) $R^4$=Cbz, R=H, $R^3$=i-Pr, $R^2$=PhOCH$_2$, $R^1$=CH$_2$CO$_2$Bu(t), X=C(=O)CH$_2$Br
z) $R^4$=Cbz, R=H, $R^3$=i-Pr, $R^2$=PhOCH$_2$, $R^1$=CH$_2$CO$_2$Bu(t), X=C(=O)CH$_2$OC(=O)—Ph-2,6-dichoro
aa) $R^4$=Cbz, R=H, $R^3$=i-Pr, $R^2$=PhOCH$_2$, $R^1$=CH$_2$CO$_2$Bu(t), X=C(=O)NMe(OMe)
ab) $R^4$=Cbz, R=H, $R^3$=i-Pr, $R^2$=PhOCH$_2$, $R^1$=CH$_2$CO$_2$Bu(t), X=C(=O)CH$_3$
ac) $R^4$=Cbz, R=H, $R^3$=i-Pr, $R^2$=H, $R^1$=CH$_2$CO$_2$Bu(t), X=CO$_2$CH$_3$
ad) $R^4$=Cbz, R=H, $R^3$=i-Pr, $R^2$=H, $R^1$=CH$_2$CO$_2$Bu(t), X=C(=O)CH$_2$OC(=O)Ph(2,6-dichloro)
ae) $R^4$=2-naphthoyl, R=H, $R^3$=i-Pr, $R^2$=H, $R^1$=CH$^2$CO$^2$Bu(t), X=C(=O)CH$_2$OPh
af) $R^4$=hydrocinnamoyl, R=H, $R^3$=i-Pr, $R^2$=PhCH$_2$, $R^1$=CH$_2$CO$_2$Bu(t), X=C(=O)CH$_2$OC(=O)Ph(2,6-dichloro)
ag) $R^4$=1-naphthoyl, R=H, $R^3$=i-Pr, $R^2$=PhCH$_2$, $R^1$=CH$_2$CO$_2$Bu(t), X=C(=O)CH$_2$OC(=O)Ph(2,6-dichloro)
ah) $R^4$=1-naphthalenesulphonyl, R=H, $R^3$=i-Pr, $R^2$=PhCH$_2$, $R^1$=CH$_2$CO$_2$Bu(t), X=C(=O)CH$_2$OC(=O)Ph(2,6-dichloro)
ai) $R^4$=3-indoleacetyl, R=H, $R^3$=i-Pr, $R^2$=PhCH$_2$, $R^1$=CH$_2$CO$_2$Bu(t), X=C(=O)CH$_2$OC(=O)Ph(2,6-dichloro)
aj) $R^4$=3-indolepropionyl, R=H, $R^3$=i-Pr, $R^2$=PhCH$_2$, $R^1$=CH$_2$CO$_2$Bu(t), X=C(=O)CH$_2$OC(=O)Ph(2,6-dichloro)
ak) $R^4$=trans-cinnamoyl, R=H, $R^3$=i-Pr, $R^2$=PhCH$_2$, $R^1$=CH$_2$CO$_2$Bu(t), X=C(=O)CH$_2$OC(=O)Ph(2,6-dichloro)

al) $R^4$=phenylmethylsulfonyl, R=H, $R^3$=i-Pr, $R^2$=PhCH$_2$, $R^1$=CH$_2$CO$_2$Bu(t), X=C(=O)CH$_2$OC(=O)Ph(2,6-dichloro)

am) $R^4$=2-quinolinecarbonyl, R=H, $R^3$=i-Pr, $R^2$=H, $R^1$=CH$_2$CO$_2$Bu(t), X=C(=O)CH$_2$OC(=O)Ph(2,6-dichloro)

an) $R^4$=2-quinolinecarbonyl, R=H, $R^3$=i-Pr, $R^2$=H, $R^1$=CH$_2$CO$_2$Bu(t), X=C(=O)CH$_2$OPh ao) $R^4$=2-quinolinecarbonyl, R=H, $R^3$=i-Pr, $R^2$PhCH$_2$, $R^1$=CH$_2$CO$_2$Bu(t), X=C(=O)CH$_2$OC(=O)Ph(2,6-dichloro)

ap) $R^4$=2-quinolinecarbonyl, R=H, $R^3$=i-Pr, $R^2$=PhCH$_2$, $R^1$=CH$_2$CO$_2$Bu(t), X=C(=O)CH$_2$OPh aq) $R^4$=2-quinolinecarbonyl, R=H, $R^3$=i-Pr, $R^2$=1-imidazolyl, $R^1$=CH$_2$CO$_2$Bu(t), X=C(=O)CH$_2$OCPh ar) $R^4$=2-naphthoyl, R=H, $R^3$=i-Pr, $R^2$=H, $R^1$=CH$_2$CO$_2$Bu(t), X=C(=O)CH$_3$ as) $R^4$=COCH$_2$CH$_2$CO$_2$Bu(t), R=H, $R^3$=(CH$_2$CH$_2$CO$_2$Bu(t), $R^2$=CH$_3$, $R^1$=CH$_2$CO$_2$Bu(t), X=C(=O)CH$_2$OPh at) $R^4$=COCH$_2$CH$_2$CO$_2$Bu(t), R=H, $R^3$=i-Pr, $R^2$=CH$_3$, $R^1$=CH$_2$CO$_2$Bu(t), X=C(=O)CH$_2$OPh au) $R^4$=1-naphthoyl, R=H, $R^3$=i-Pr, $R^2$=PhCH$_2$, $R^1$=CH$_2$CO$_2$Bu(t), X=C(=O)CH$_2$N(CH$_2$)$_5$ In Reaction Scheme 2, the functional group X of compound (X) may be introduced by several unit operations after the reactions involved in the synthesis of the compound (VIII) or (IX), or the compound (VII) or (IX) already having desired substituent X may be proceed with the subsequent reactions.

The acrylate derivative (VII) may be synthesized by any one of two processes as depicted in Reaction Scheme 3 below.

Reaction Scheme 3

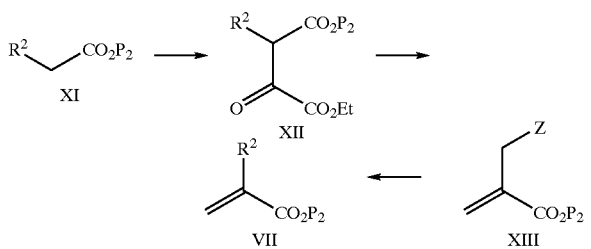

Ester derivative (XI) is reacted with diethyl oxalate to give oxalate derivative (XII) which is then reacted in the presence of a base to give desired acrylate derivative (VII). Alternatively, it may be synthesized by various processes starting from the known compound (XIII). That is, the known compound (XIIIa) is easily converted into compounds (XIIIb), (VIIe), (VIIf), (VIIg), etc.

In the compounds (XI) and (XII), the substituents are exemplified as follows:

a) $P_2$=Et, $R^2$=Ph
b) $P_2$=Et, $R^2$=4-bromophenyl
c) $P_2$=Et, $R^2$=1-naphthyl
d) $P_2$=Et, $R^2$=2-naphthyl In the compounds (VII) and (XIII), the following combination of the substituents can be synthesized by the above process.

In the compound of (VII), a) $R^2$=Ph, $P_2$=Et
b) $R^2$=4-bromophenyl, $P_2$=Et
c) $R^2$=1-naphthyl, $P_2$=Et
d) $R^2$=2-naphthyl, $P_2$=Et
e) $R^2$=CH$_2$OAc, $P_2$=Et
f) $R^2$=CH$_2$Ph, $P_2$=Et
g) $R^2$=CH$_2$OPh, $P_2$=Et In the compound (XII), a) $R^2$=Et, Z=OH
b) $R^2$=Et, Z=Br Hereinafter, the representative compounds synthesized by the process of the invention will be listed according to their structural formulae. The representative compounds according to the invention are numbered by the inventors for convenience' sake in which MP represents more polar fractions from HPLC at the previous step of deprotection while LP represents less polar fractions from HPLC. However, they are presented for the purpose of illustration of the synthesis of the compounds of the invention and for substantiating the fact that the compounds of the invention can be synthesized by the above mentioned process, but the present invention should not be limited to the listed compounds in any manner.

(3)

(10)

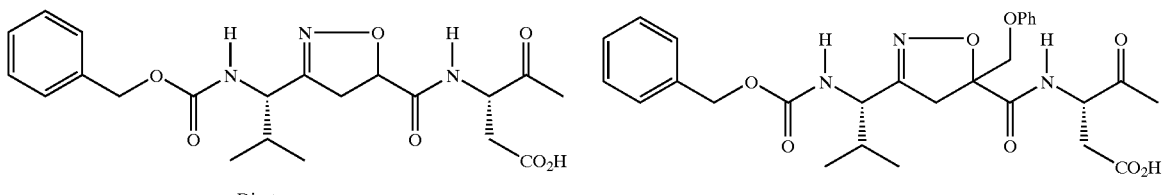

Diastereomer

Diastereomer (less polar)

(11)

(12)

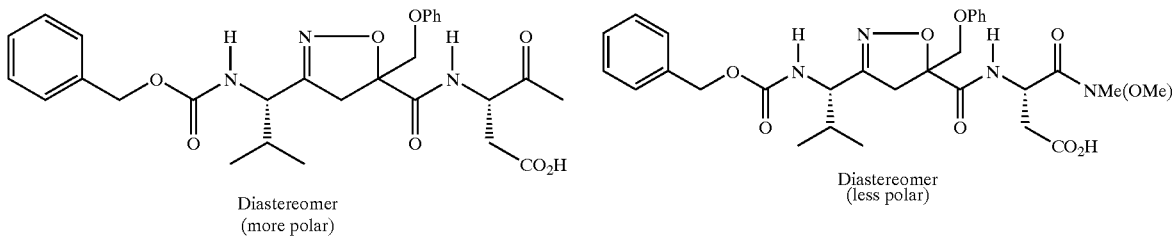

Diastereomer (more polar)

Diastereomer (less polar)

-continued
(13)
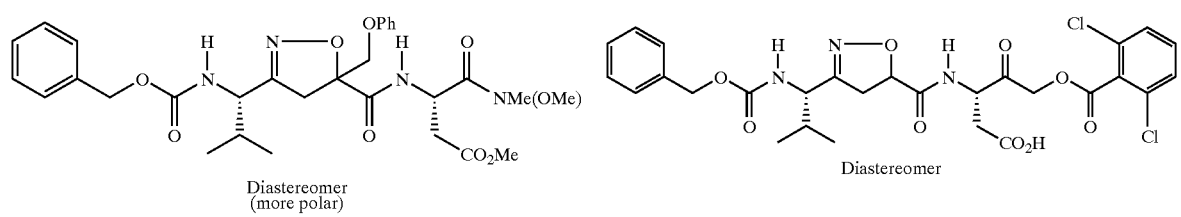
(14)
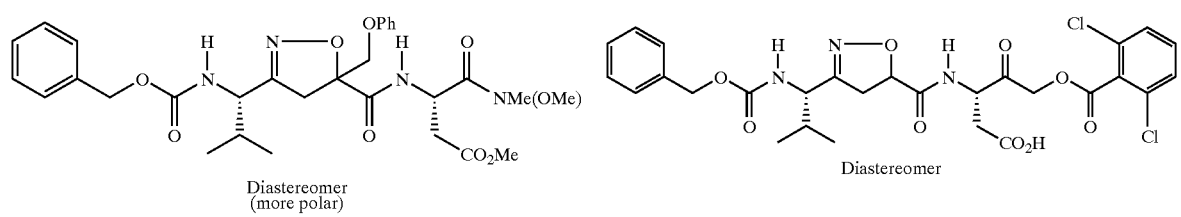
(17)
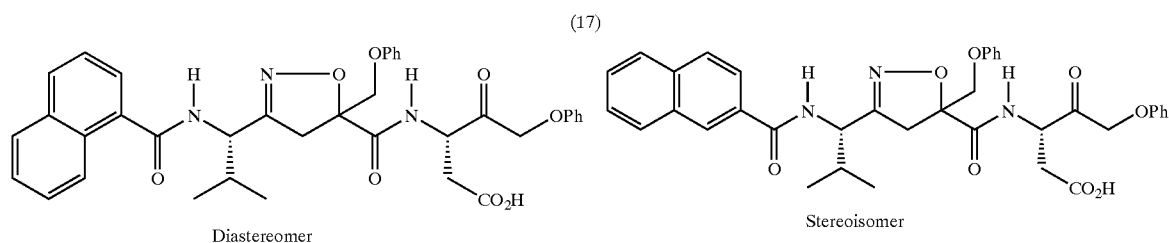
(18)
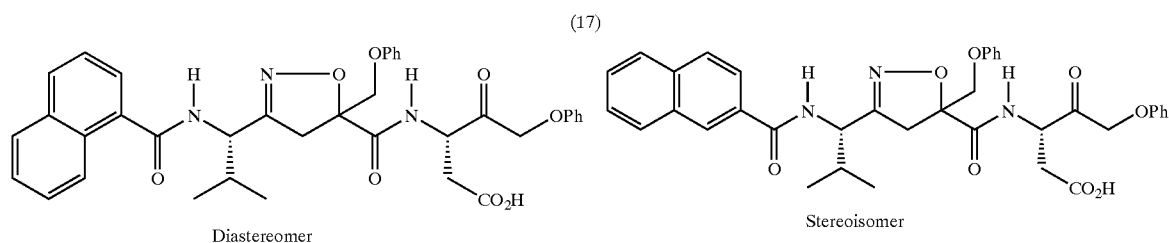
(19)
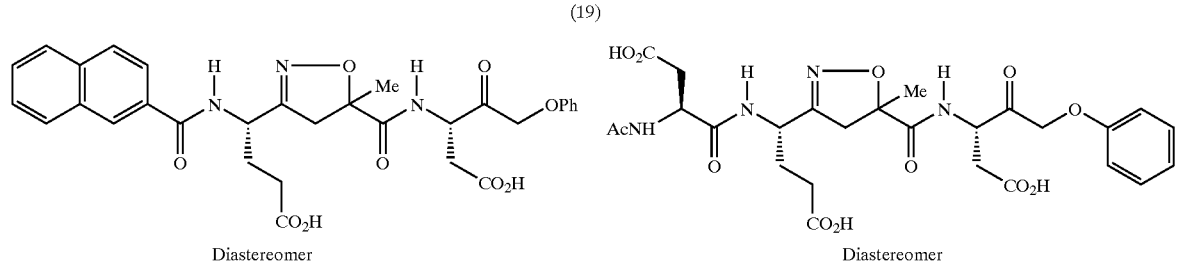
(20)
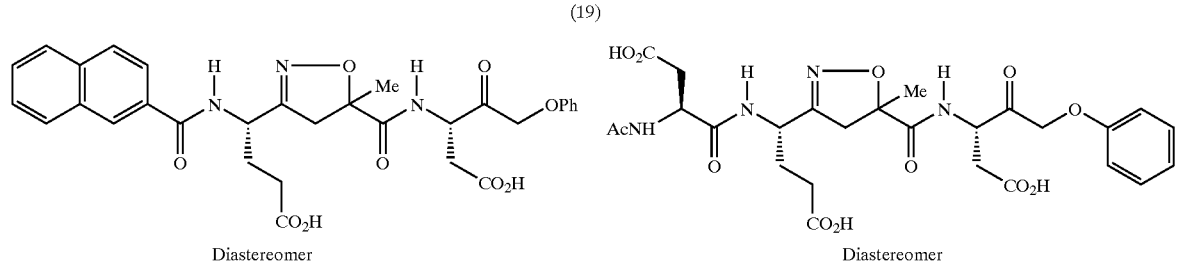
(22)
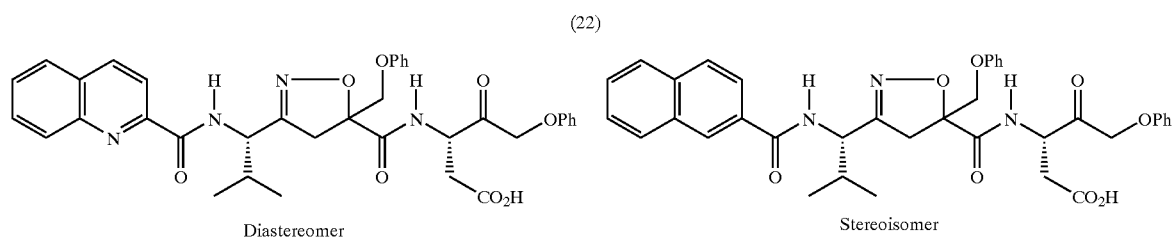
(23)
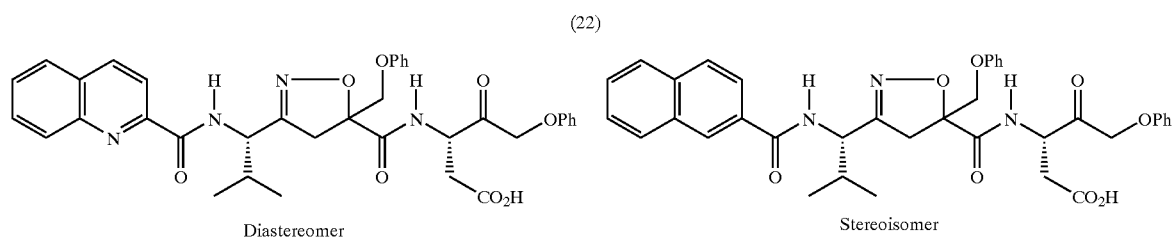
(24)
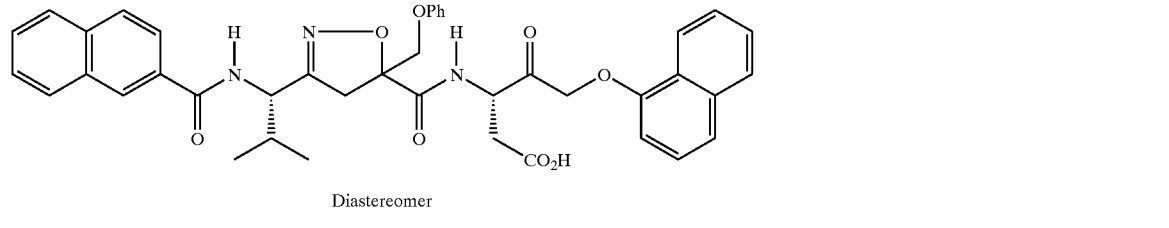
(25)
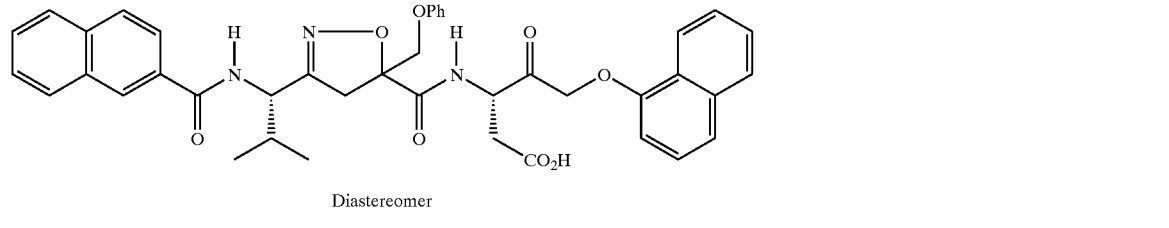

-continued
(26)
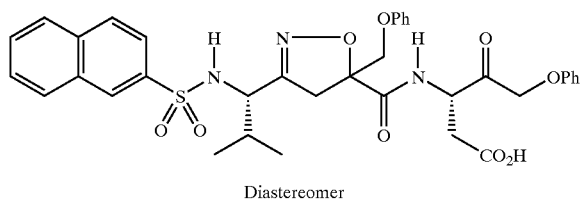
Diastereomer
(27)
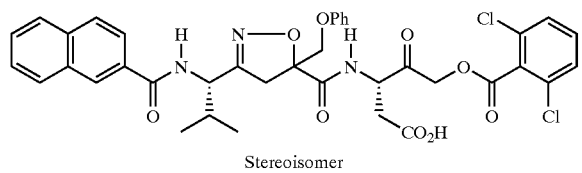
Stereoisomer
(28)
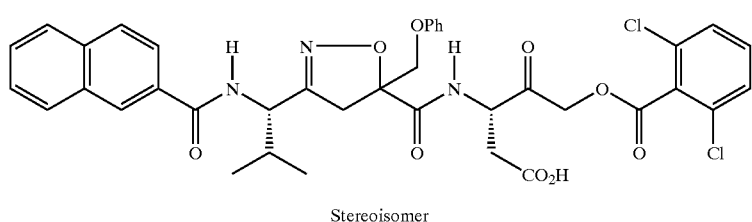
Stereoisomer
(29)
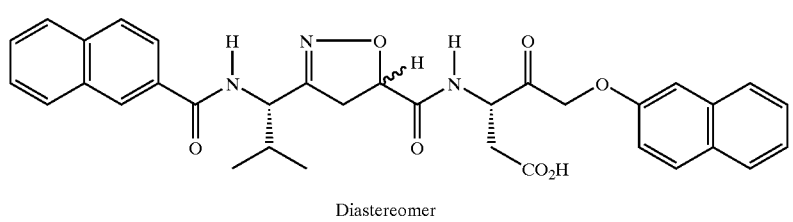
Diastereomer
(30)
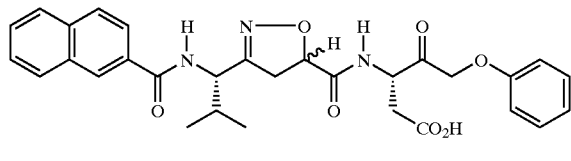
(31)
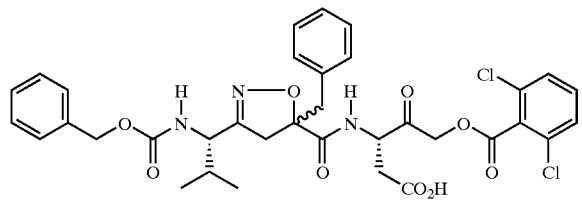
(32)
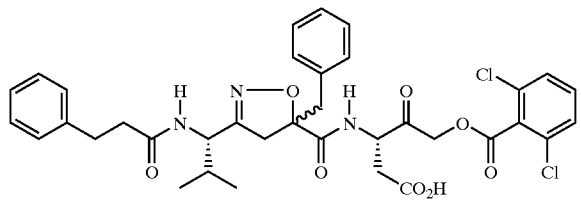
(33)
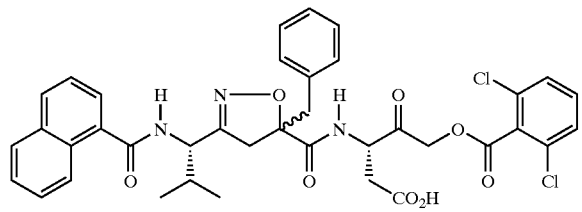
(34)
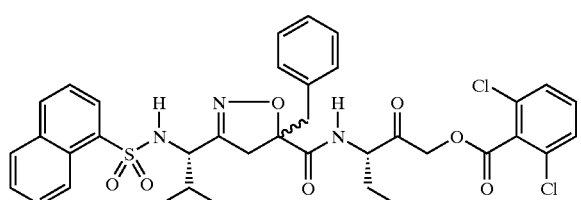
(35)
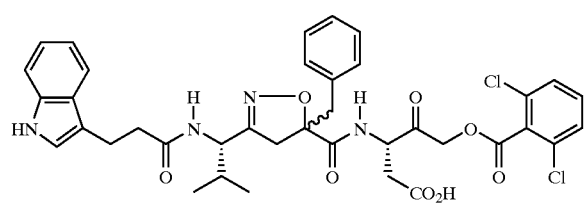
(36)
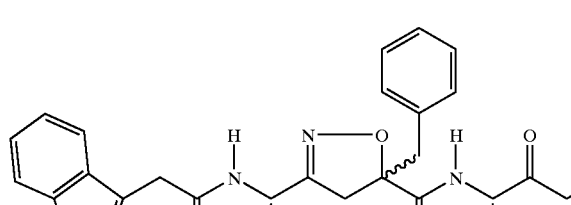

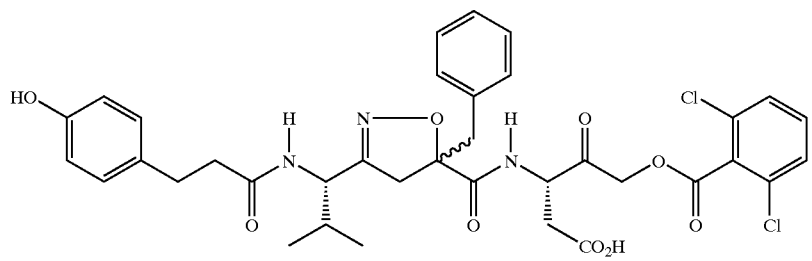
(37)
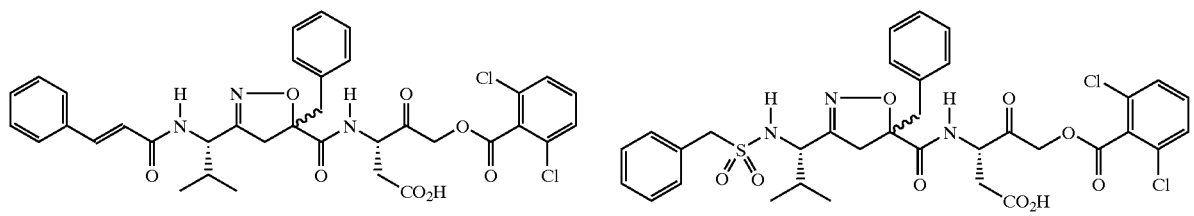
(38) (39)
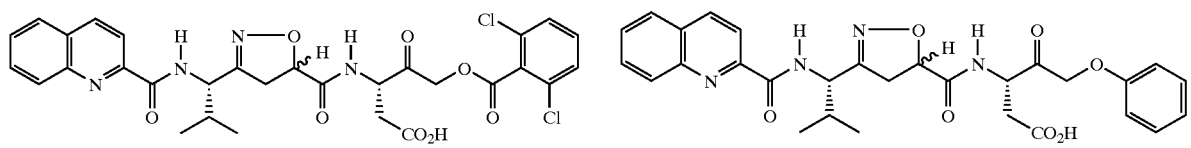
(40) (41)
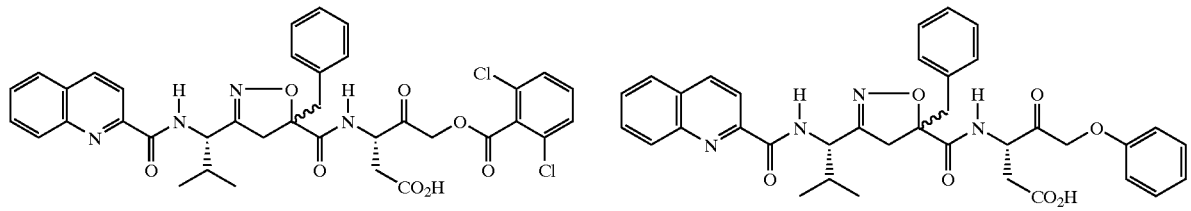
(42) (43)
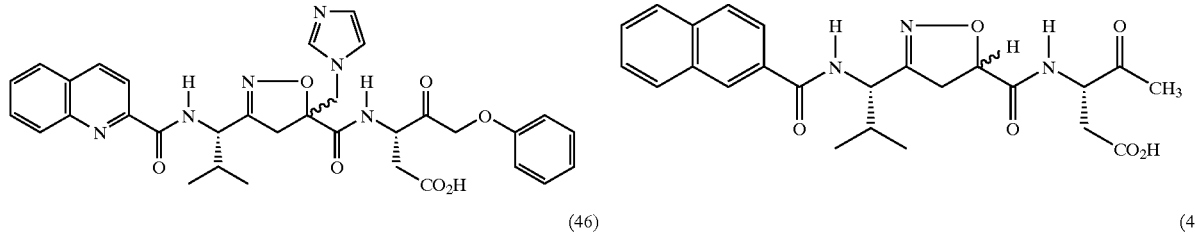
(44) (45)
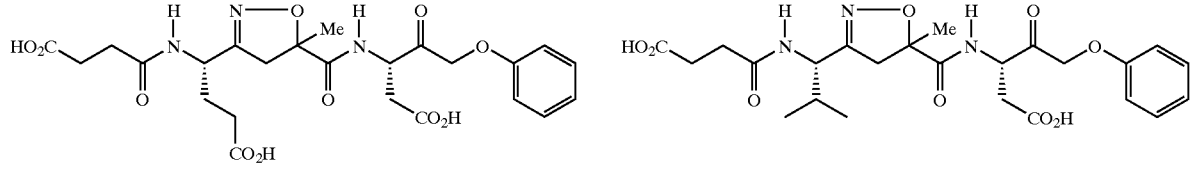
(46) (47)
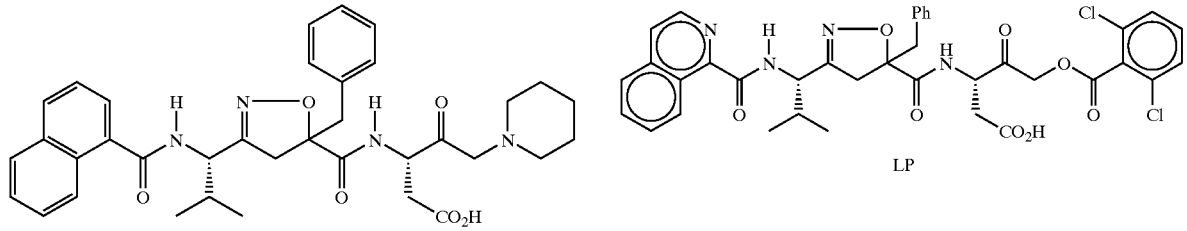
(48) (49)

-continued
(50)
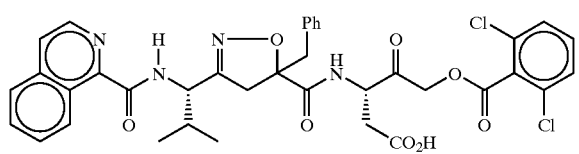
MP
(51)
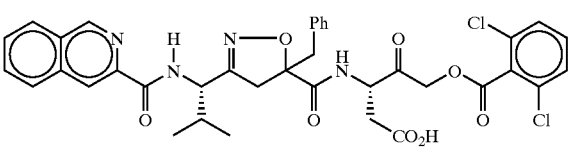
LP
(52)
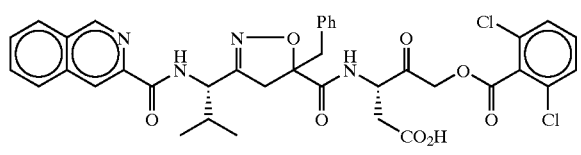
MP
(53)
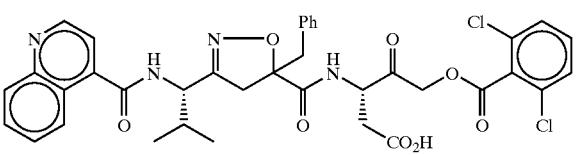
LP
(54)
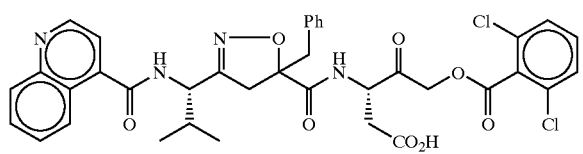
MP
(55)
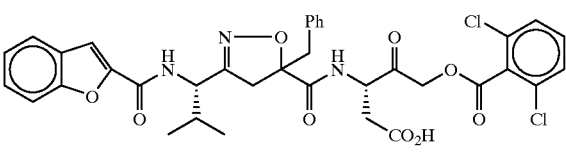
LP
(56)
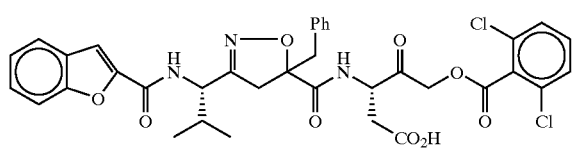
MP
(57)
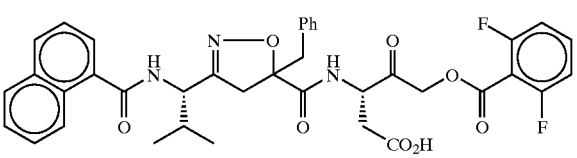
LP
(58)
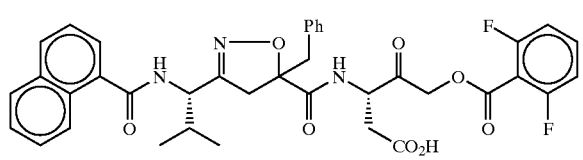
M
(59)
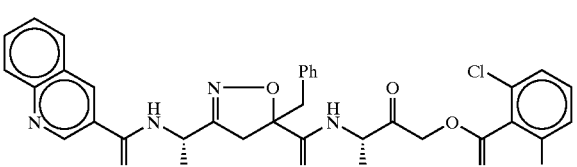
LP
(60)
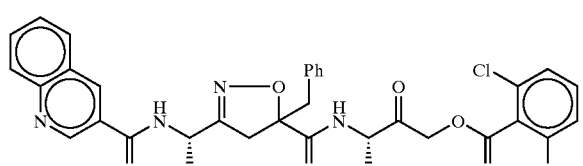
M
(61)
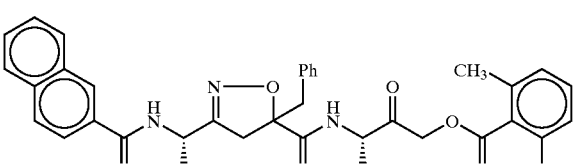
Mi
(62)
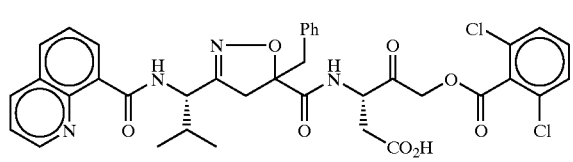
Mi
(63)
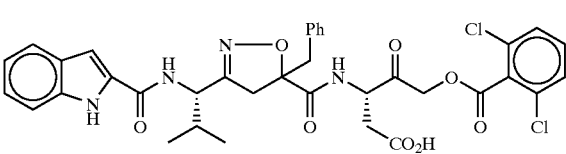
LP

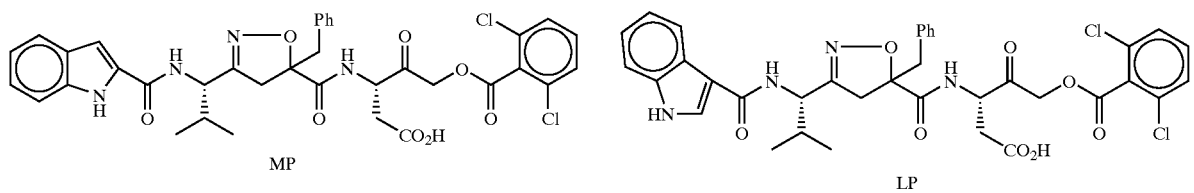
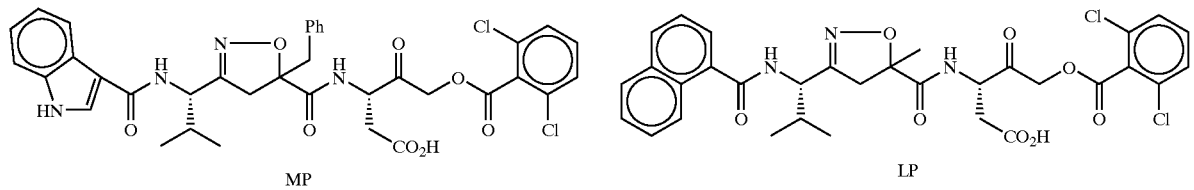
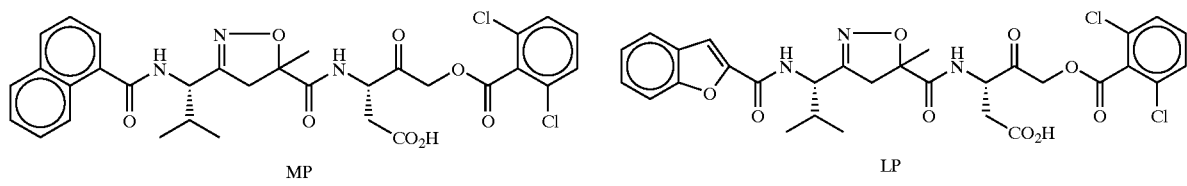
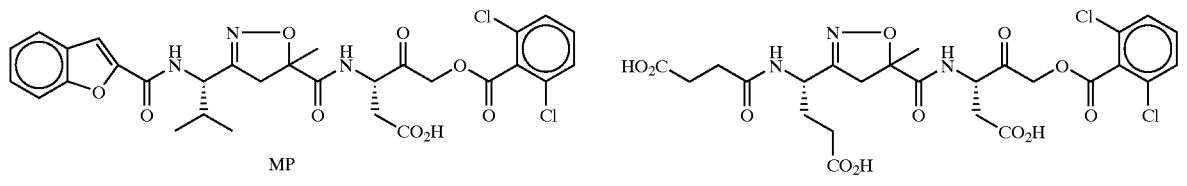
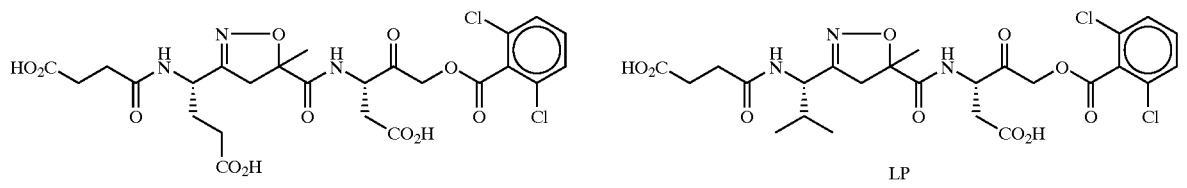
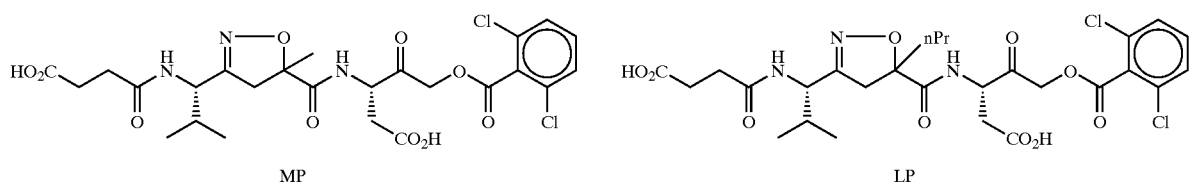
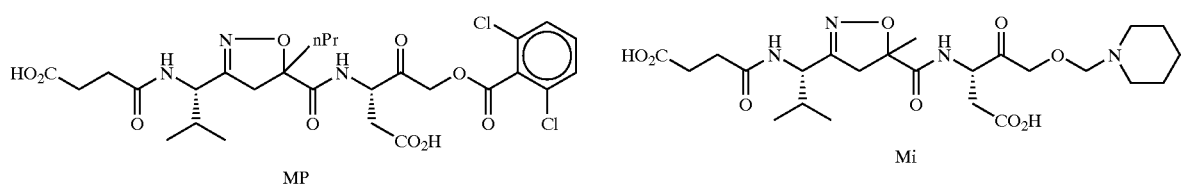

-continued
(78)
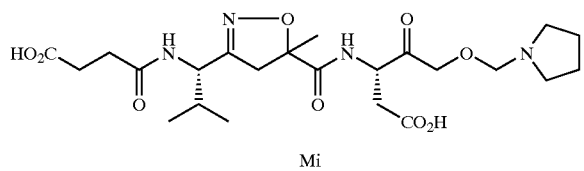
Mi
(79)
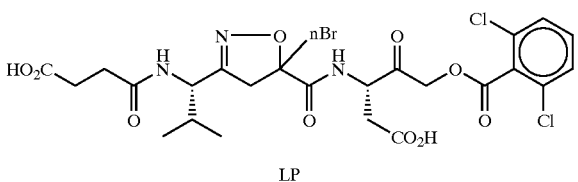
LP
(80)
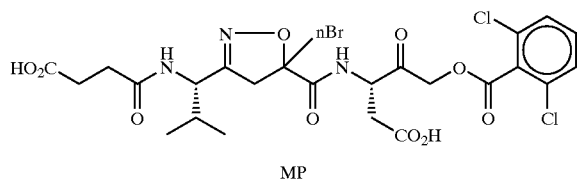
MP
(81)
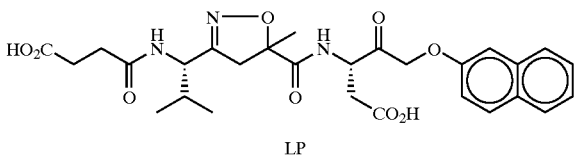
LP
(82)
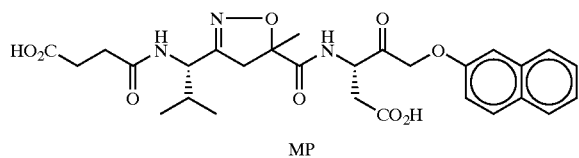
MP
(83)
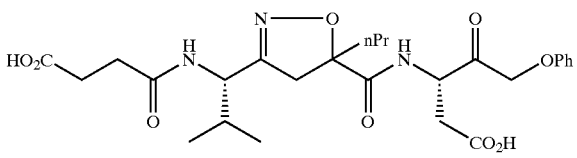
Mix
(84)
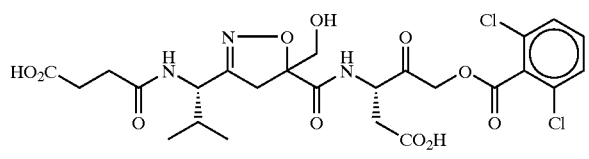
Mix
(85)
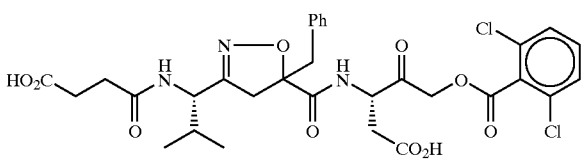
LP
(86)
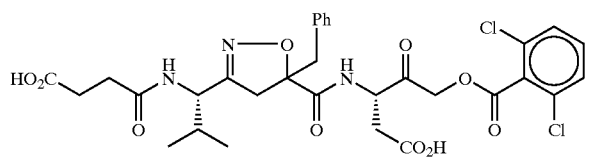
MP
(87)
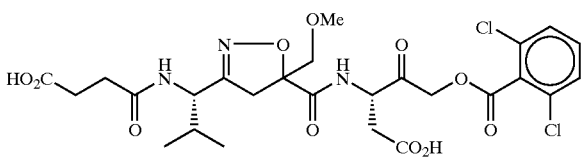
Mix
(89)
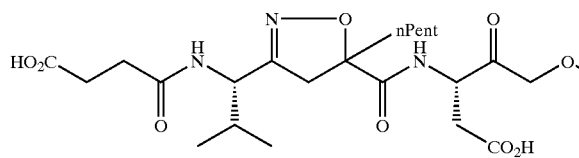
LP
(90)
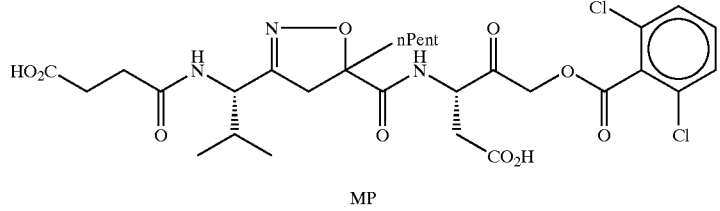
MP

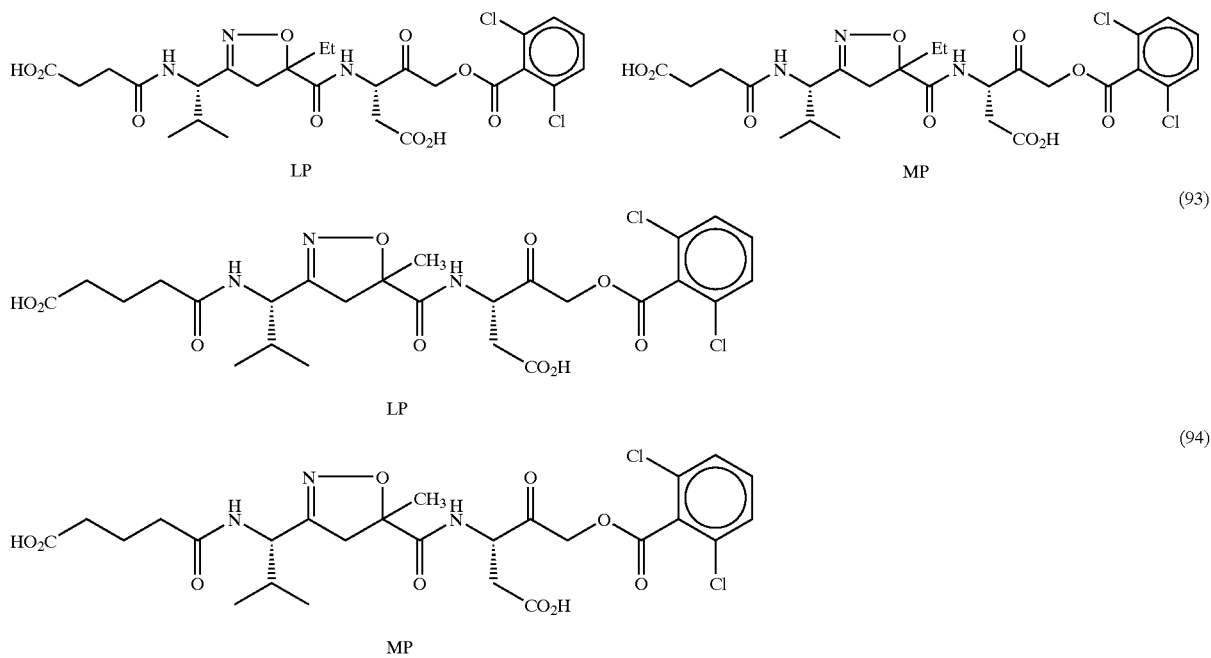

The isoxazoline derivative of formula (I) and the pharmaceutically acceptable salts, esters, and isomers thereof have useful pharmacological properties. For example, they have an inhibitory activity for caspases. Due to their pharmacologcal activity such as effects on anti-inflammation or inhibition of apoptosis, they can effectively be used as the therapeutics for a number of diseases, for example, the disease in which cells are abnormally died, dementia, cerebral stroke, brain impairment due to AIDS, diabetes, gastric ulcer, cerebral injure by hepatitis, fulminant hepatic failure, (FHF), sepsis, organ transplantation rejection reaction, rheumatic arthritis, cardiac cell apoptosis due to ischaemic cardiac diseases and anti-inflammation.

In particular, the composition according to the invention can preferably be used as the therapeutics for fulminating hepatic failure.

As described in detail hereinafter, the present inventors examined, using the compound of formula (I), in vitro and in vivo caspase inhibitory activities, the viability ratio of hepatocytes in case where hepatic diseases were induced by ConA or TNFα/Actinomycin D, therapeutic effect against hepatitis, reduction of hepatocytic apoptosis, and inhibition of PARP cleavage.

The present inventors have also conducted experiments on the effect of the compound of formula (I) according to the invention on cellular viability in case where apoptosis was induced by IFNγ and anti-Fas antibody, and compared the results thereof with the existing caspase inhibitors, Ac-DEVD-CHO and/or z-DEVD-cmk. Briefly, we examined the efficacy of the new caspase inhibitor of formula (I) to inhibit Con A-induced acute hepatic failure in mice. As a result, this small-molecule, non-peptide-based inhibitor showed inhibition of not only caspase activities but also apoptotic death of hepatocytes in vitro and in vivo. These results suggest that the compound of formula (I) according to the present invention could be a candidate of therapeutic agent for human FHF caused by massive apoptotic death of hepatocytes.

Figure 2:
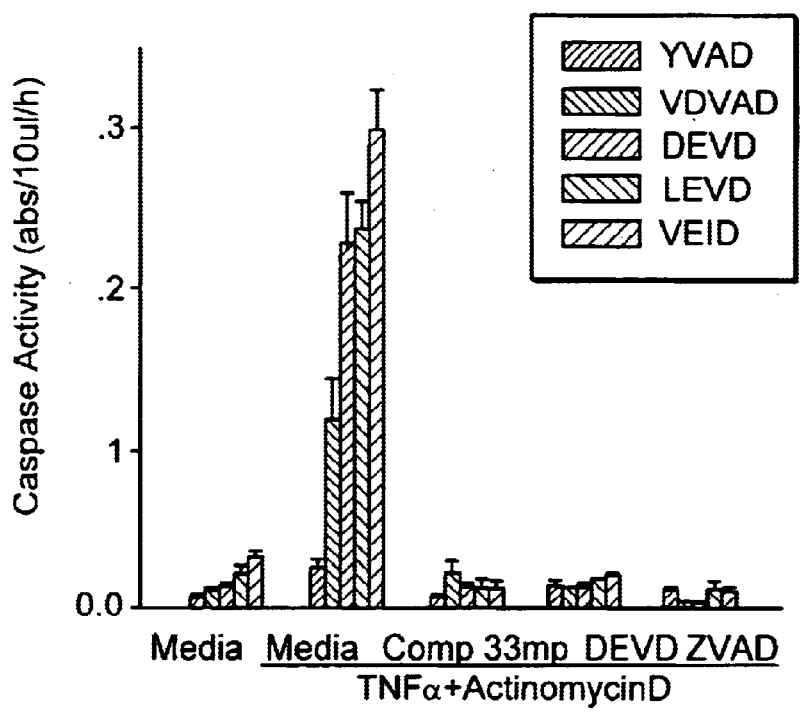
FIG. 2 represents a graph showing caspase inhibition activities of the compound of the invention in rat hepatocytes in which apoptosis was derived by TNFα and Actinomycin D treatment.

The compound of the invention is a small-molecule, non-peptide-based caspase inhibitor which has a broad-spectrum activity (see FIGS. 1 & 2). The compound of formula (I) is different from BCNU or COX-2inhibitor in the fact that it was originally designed as a specific inhibitor of caspase family enzymes. It is noteworthy that apoptotic process is very complicated and caspases are critically involved in several steps of this process. Moreover, relatively little is known about caspase regulation largely because many of the known substrates have been found serendipitously. Thus, to block short-term, massive apoptosis of hepatocytes during acute phase of FHF, a broad-spectrum caspase inhibitor might exert more potent effect than a specific-spectrum caspase inhibitor. In this regard, the compound of formula (I) could be an ideal candidate.

The present inventors used ConA-induced hepatitis model to test the apoptosis-blocking effect of caspase inhibitor, the compound of formula (I).

Several cytokines are involved in Con A-induced hepatitis: IL-2, IFNγ, TNFα, IL-6, IL-4, and IL-10. The present inventors assessed the effect of the compound of formula (I) to serum IL-1β, IL-2, IL-4, and IFNγ concentrations elevated by Con A. As a result, the compound of formula (I) according to the present invention significantly suppressed IL-1β level in a dose-dependent manner (see FIG. 5A) due to its caspase-1-inhibiting activity shown in FIGS. 1 and 2. However, the compound of formula (I) did not significantly affect IL-2, IL-4, and IFNγ levels (FIGS. 5B, C, D). These results could be attributed to the fact that the major cell population to which the compound of formula (I) exerted its activity as a caspase inhibitor is Fas-expressing hepatocytes. The compound of formula (I) rescued hepatocytes from caspase-involved apoptosis, but did not directly suppress activated T cells. One of the biosubstates for caspase-3-like protease in cells is PARP (116 kDa) which is cleaved into 85- and 31-kDa fragments in cells undergoing apoptosis. Therefore, the appearance of an 85 kDa-cleavage product of PARP has been proposed as an early marker of apoptosis (See, Lazebnik, Y. A. et al., 1994, *Nature* 371: 346–347; Kaufmann, S. H. et al., 1993, *Cancer Res.* 53: 3976–3985).

Figure 6A:
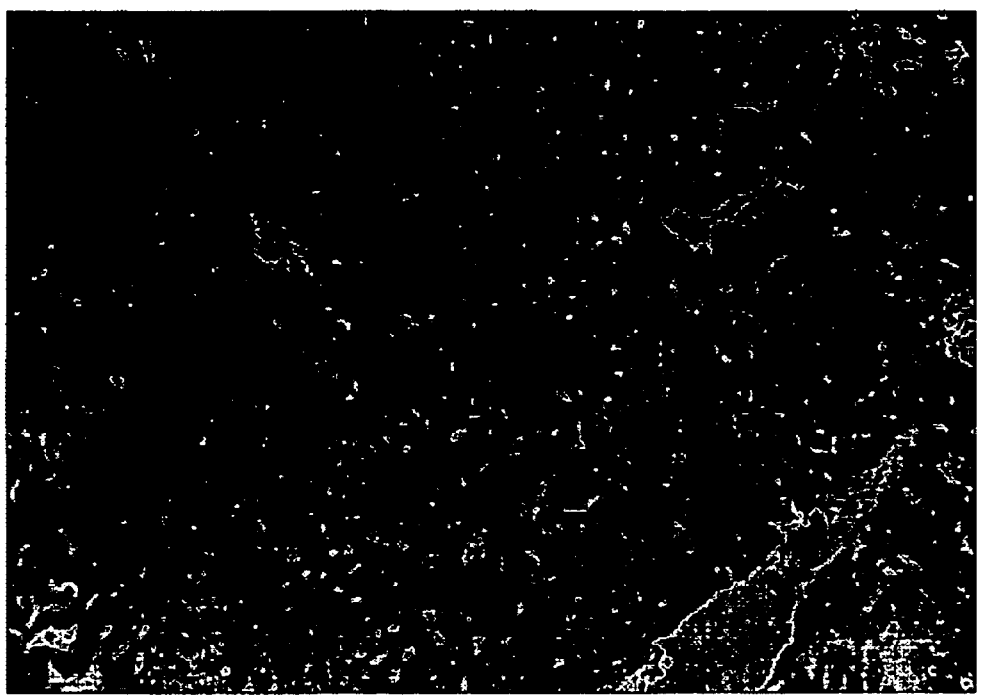
FIG. 6 represents a photograph showing inhibition activities of the compound of the invention in apoptotic lesions and morphological histological changes of hepatocytes in ConA-treated mouse liver.
Figure 6B:
Figure 6C:
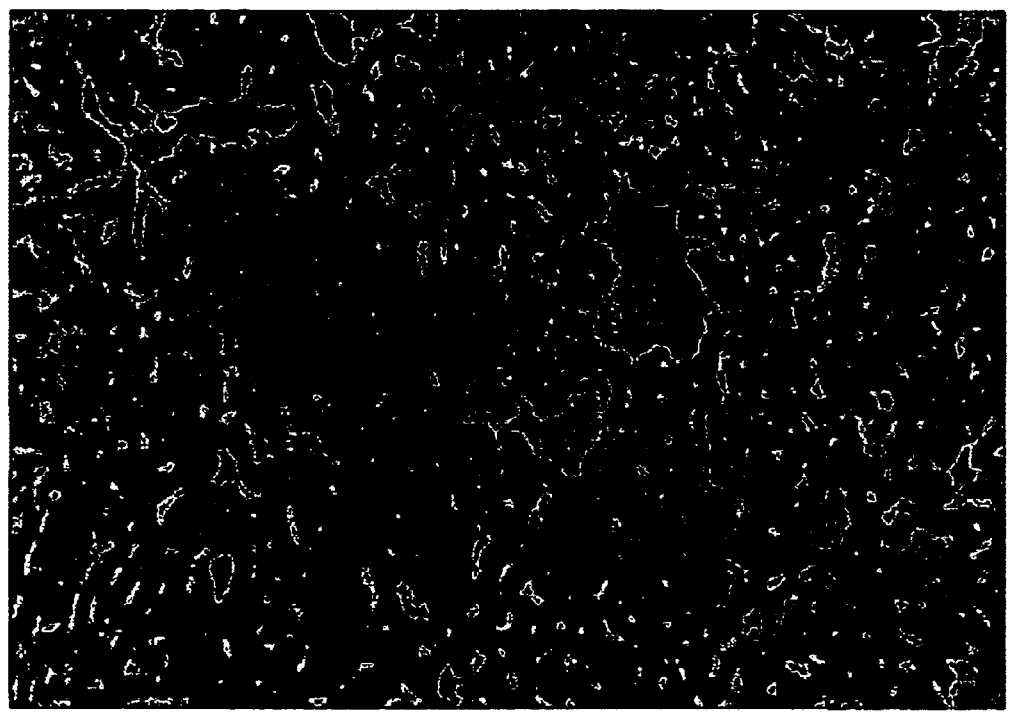
Figure 6D:
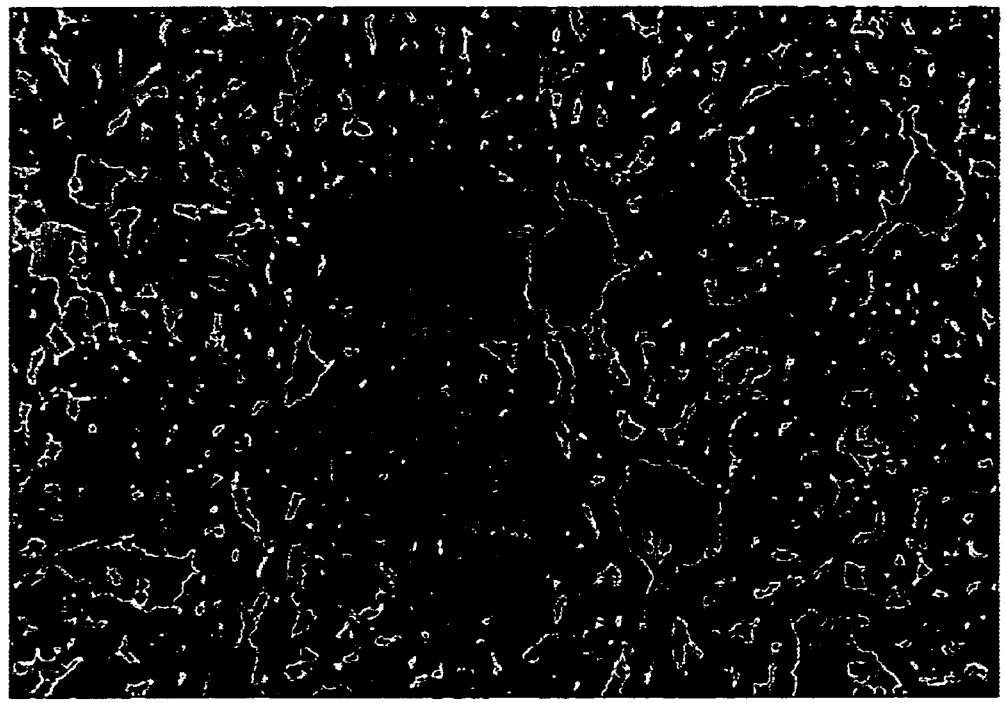
Figure 6E:
Figure 6F:
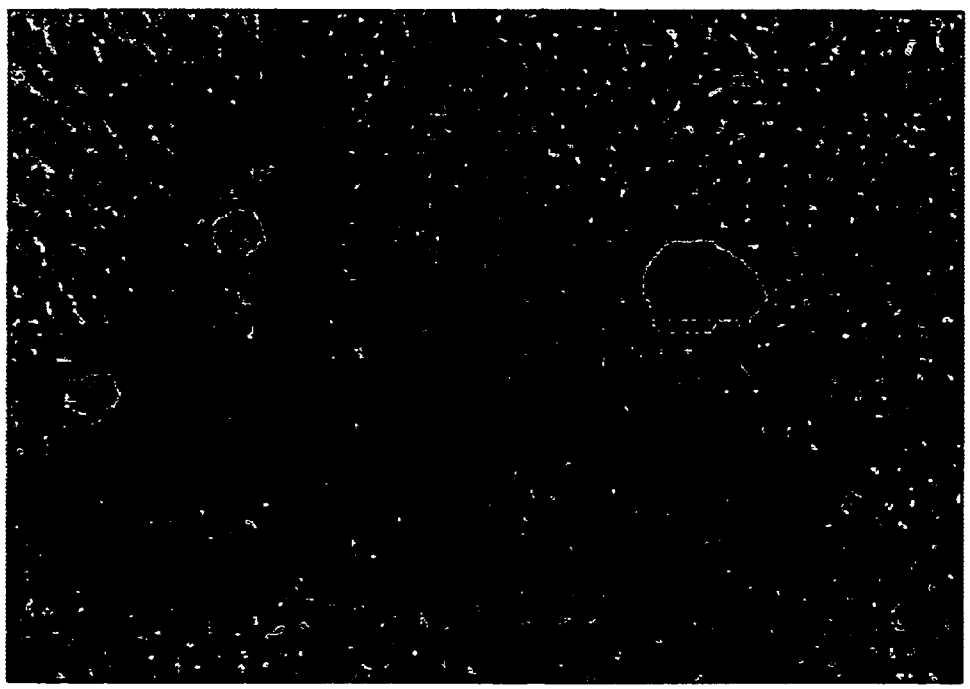
Figure 6G:
Figure 6H:
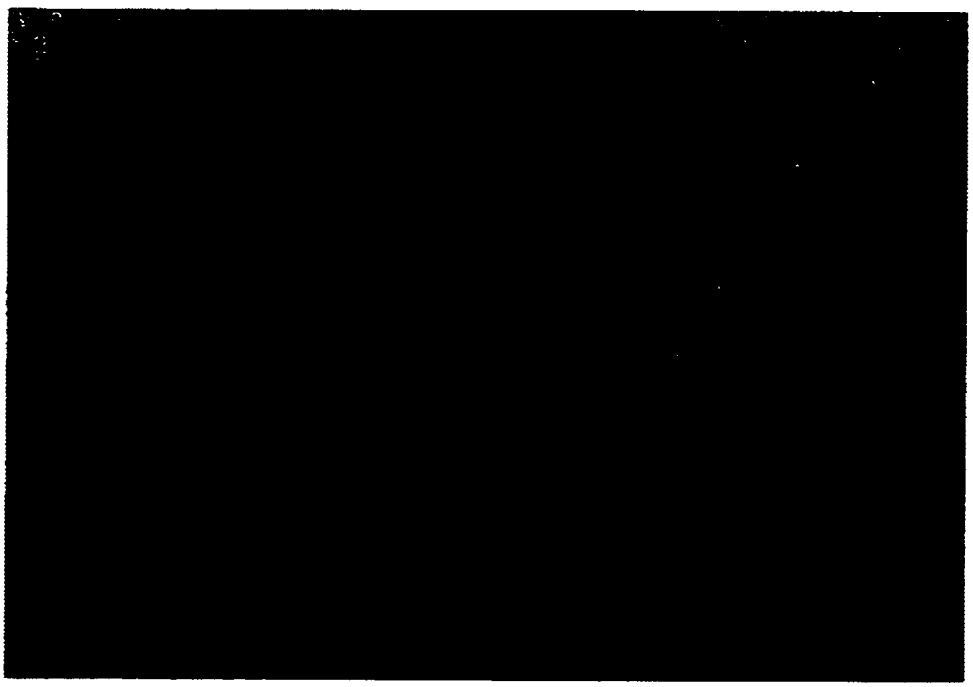
Figure 6I:
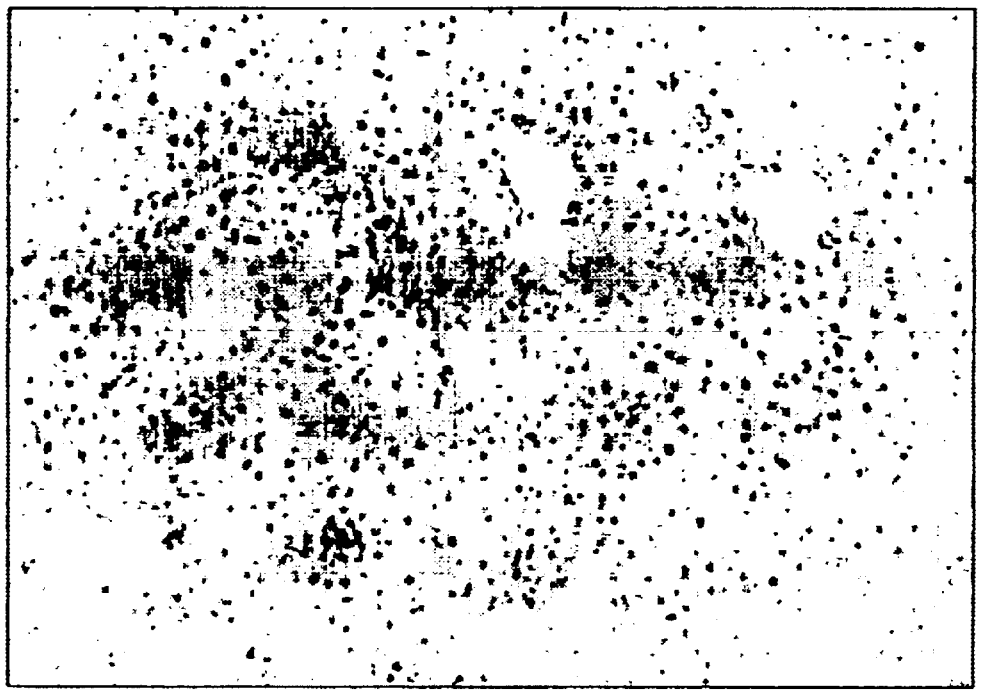
Figure 6J:
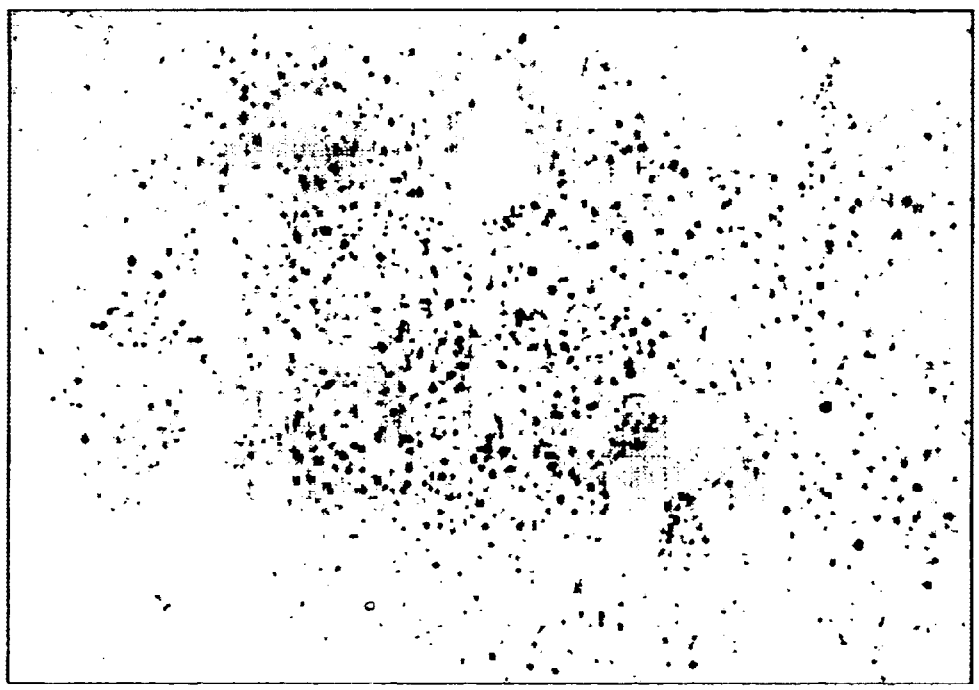
Figure 6K:
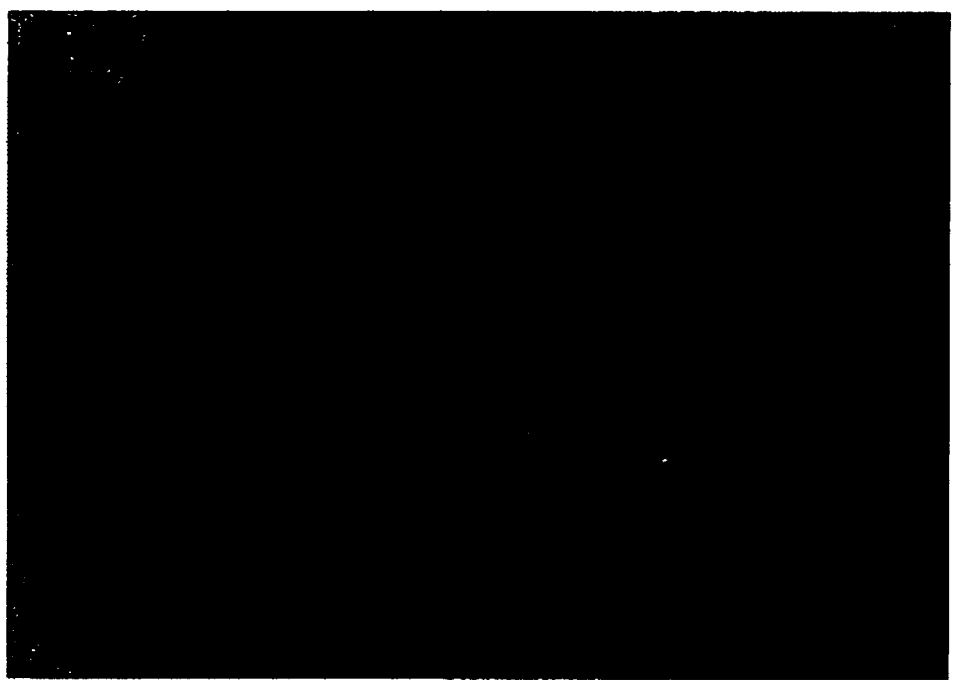
Figure 6L:
Figure 7:
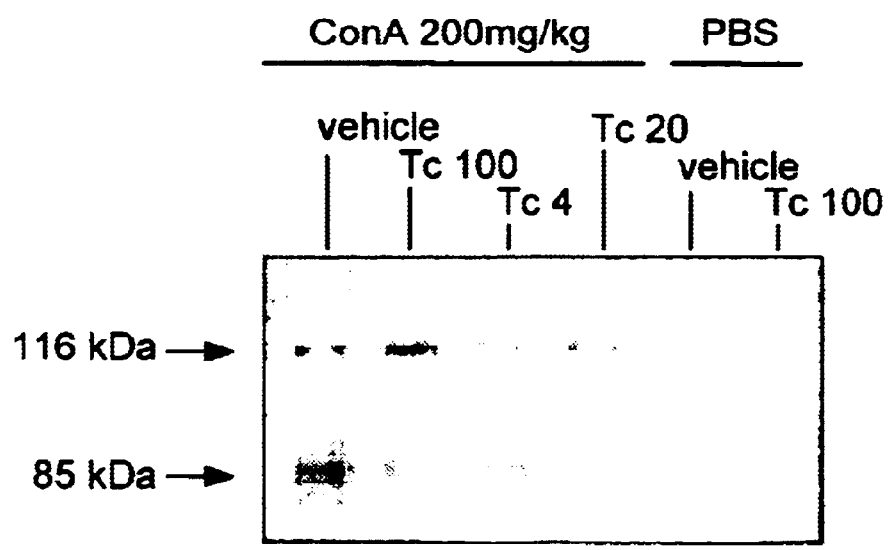
FIG. 7 represents an electrophoresis image showing inhibition activities of the compound of the invention on PARP cleavage caused by ConA-induced apoptotic death of hepatocytes. Each lane is representative of 10 mice per group.

The compound of formula (I) inhibited PARP cleavage caused by Con A-induced apoptotic death of hepatic cells in a dose-dependent manner (see FIG. 7). On Western blot analysis, the amount of 85 kDa-cleavage product gradually reduced as dose of compound 33 is increased, but intact 116 kDa PARP appeared relatively constant. It is considered the hepatocytes which virtually underwent apoptosis comprise only a small portion compared with the whole liver mass. This result is consistent with histological examination. As shown in FIG. 6, Con A induced severe morphological and histological changes to hepatocytes and the apoptotic lesions were clearly detectable. However, a large proportion of hepatocytes still remained alive and apoptotic cells comprise a part. This phenomenon explains the appearance of intact 116 kDa PARP even in the liver of ConA/vehicle mice.

Figure 8:
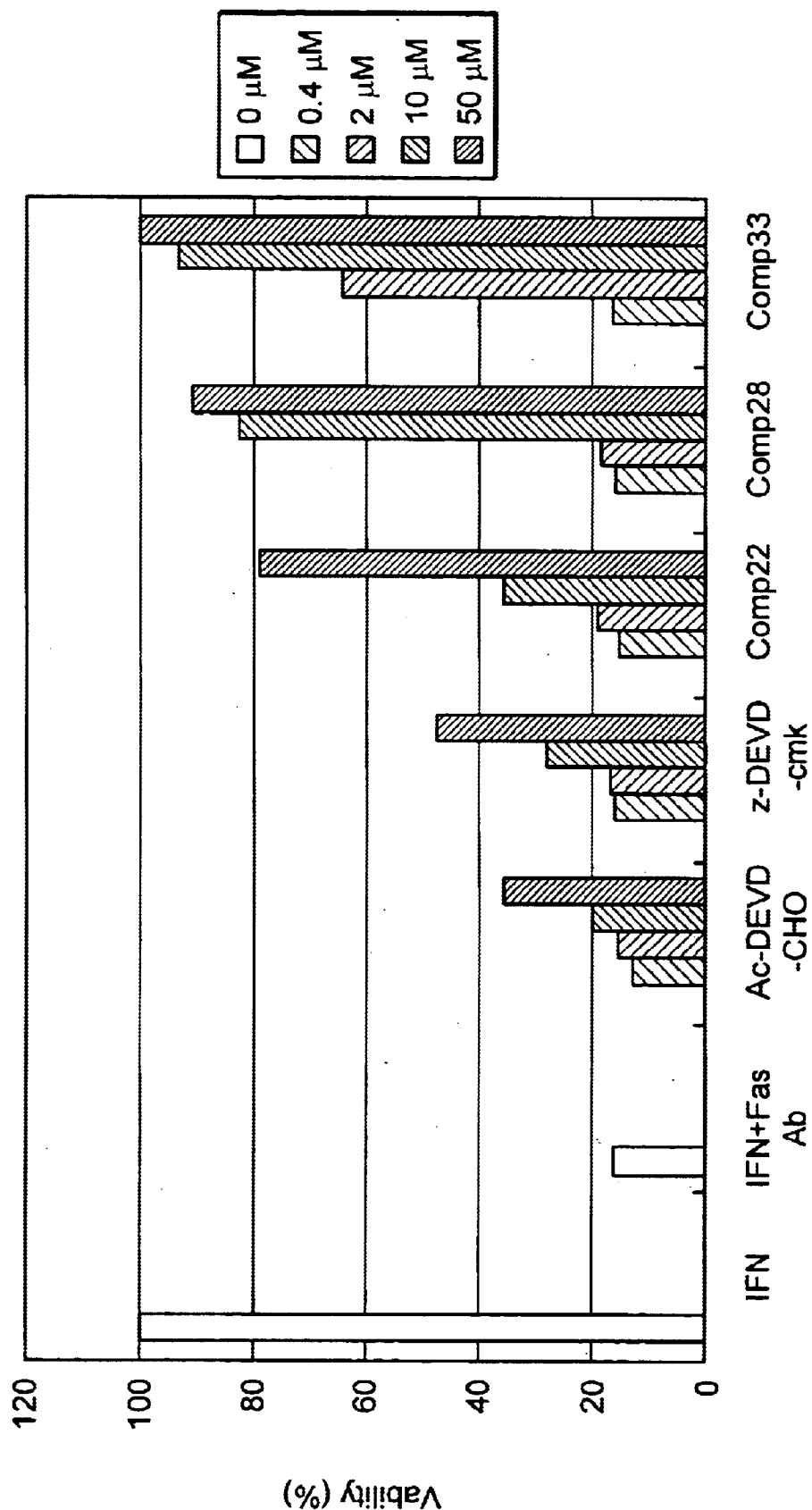
FIG. 8 is a graphical representation showing hepatic protection of the compound of the invention from IFNγ and anti-Fas antibody-induced apoptosis.

Meantime, the present inventors induced an artificial apoptosis by treating Fas responsive cell with IFNγ and anti-Fas antibody, and conducted experiments in order to evaluate the inhibitory activity of the compound of formula (I) on the cells against apoptosis. As a result, the inventors discovered that the compound of formula (I) revealed 2-fold or more superior inhibitory effect over the known Ac-DEVD-CHO or z-DEVD-cmk (At the same concentration, the cell viability was 35.1% (Ac-DEVD-CHO), 47.3% z-DEVD-cmk and 100% (Compound 33), see Table 1 and FIG. 8).

From the above experiment results, it is noted that the non-peptidic compound of formula (I) has a wide variety of caspase inhibitory activities and thus, anti-inflammation and apoptosis prevention effects, especially can effectively be used as therapeutics for preventing massive apoptosis of hepatocytes in human FHF.

The compound of formula (I) is a new, non-peptide based caspase inhibitor. Its broad-spectrum activity could be a beneficial property as a therapeutic agent blocking the massive apoptosis of hepatocytes in human FHF.

The compounds of the present invention, therefore, may be used as medicines against above-mentioned diseases. Said use as a medicine or method of treatment comprises local or systemic administration to patients of an effective amount of the compounds according to the invention for treating the diseases.

The subject compounds may be formulated into various pharmaceutical forms for administration purposes. Said pharmaceutical forms or compositions are deemed to novel and consequently constitute a further aspect of the present invention. Also the preparation of said composition constitutes a further aspect of the present invention. To prepare the pharmaceutical composition of this invention, an effective amount of the compound, in base or salt form, as the active ingredient is combined in intimate admixture with a pharmaceutically acceptable carrier which may take a wide variety of forms depending on the form of preparation desired for administration. These pharmaceutical compositions are desirably in unitary dosage form suitable, preferably, for administration orally, percutaneously, or by parenteral injection. It is especially advantageous to formulate the above pharmaceutical composition in unit dosage form for ease of administration and uniformity of dosage. For example, in preparing the composition in oral dosage form, any of the usual pharmaceutical media may be employed for example, water, glycols, oils, alcohols and the like in the case of oral liquid preparations such as suspensions, syrups, elixirs and solutions: or solid carriers such as starches, sugars, kaolin, lubricants, binders, disintegrating agent and the like in the case of powders, pills, capsules and tablets. Because of their ease of administration, tablets and capsules represent the most advantageous oral dosage unit form, in which case solid pharmaceutical carriers are obviously employed It is preferable that tablets and fills are enteric-coated.

For parenteral compositions, the carrier will usually include sterile water, at least in large part, though other ingredients, for example, to aid solubility, may be included. Injectable solutions, for example sterilized aqueous injection suspension or oil suspension, may be prepared with suitable dispersing agents, wetting agents or suspending agents. Solvents which can be used for this purpose include water, Linger's solution, isotonic NaCl solution, etc. Sterilized fixed oils can also be used as a solvent or a suspending medium. Any non-excitatory fixed oils including mono-, diglycerides can be used for this purpose and fatty acids such as oleic acid can be used in the injectable preparation.

In the preparation suitable for percutaneous administration, the carrier optionally includes a penetration enhancing agents and/or a suitable wetting agent, optionally combined with suitable additives of any nature in minor proportions, wherein the additives do not give a significant deleterious effect on the skin. Said additives may facilitate the administration to the skin and/or may assist preparation of the desired compositions. These compositions may be administered in various routes, e.g., as a tnansdermal patch, as a spot-on or as an ointment Dosage unit as used in the specification and claims herein refers to physically discrete units suitable as unitary dosage, each unit containing a predetermined quantity of active ingredient calculated to produce the desired therapeutic effect in association with the required pharmaceutical carrier. Examples of such dosage unit forms are tablets, capsules, pills, powder packets, wafers, injectable solutions or suspensions, teaspoonfuls, tablespoonfuls and the like, and segregated multiples thereof.

In view of the usefulness of the subject compounds in the treatment of the disease in which cells are abnormally died, dementia, cerebral stroke, AIDS, diabetes, gastric ulcer, hepatic injure by hepatitis, sepsis, organ transplantation rejection reaction and anti-inflammation, it is evident that the present invention provides a method of treating patients suffering from the diseases, which comprises the local or systemic administration of a pharmaceutically effective amount of the compound of formula (I) or the pharmaceutically acceptable salt, ester or stereochemically isomeric form thereof in admixture with a pharmaceutical carrier.

Those skilled in the treatment of the diseases associated could easily determine the effective amount of the caspase inhibitor, especially the compound of formula (I) to be administered into a subject. In general, it is contemplated that an effective amount would range from 0.01 mg/kg to 100 mg/kg body weight a day in a unit dosage or divided dosage. However, it is evident to those skilled in the art that such amount ranges are guidelines only and are not intended to limit the scope or use of the invention in any manner. The specific dosage level for a specific subject would depend upon the particular compound to be employed, weight of a subject, health conditions, regimen, administration period of the drug, administration route, excretion rate, combination of drug, the severity of diseases, etc.

The present invention will be described in greater detail through the following examples. The examples are presented for illustrating purposes only and should not be construed as limiting the invention which is properly delineated in the claims.

EXAMPLES

(A) Hydroxamoyl Chloride Synthesis (Examples 1 to 4)

Example 1

Synthesis of N-t-Butoxycarbonyl-(S)-valinal and N-t-Butoxy-carbonyl-(S)-valinal Oxime To a solution of dimethyl sulfoxide (11.7 mL, 3.0 eq) in dry $CH_2Cl_2$ (~200 mL) under $N_2$ at $-60°$ C. was added slowly oxalyl chloride (5.78 mL, 1.2 eq). After 10 min., a solution of N-t-butoxycarbonyl-(S)-valinol (11.23 g, 55.2 mmol) in $CH_2Cl_2$ (30 mL) was added slowly, and the flask was rinsed with 20 mL of $CH_2Cl_2$. The resulting white suspension was stirred for 1 h at ~-50° C. The reaction solution was treated with diisopropylethylamine (28.8 mL. 3.0 eq) and stirred for about 20 min. at $-23°$ C. then diluted with hexanes (400 mL). The mixture was washed with water(150 mL), 1N-$KHSO_4$ solution (×3, total 1 L), dried with anhydrous $Na_2SO_4$, filtered and concentrated. The yellowish liquid obtained was used directly in next step without further purification.

The crude valinal in ethanol (60 mL)-water (30 mL) at water bath temperature was treated with hydroxylamine hydrochloride (5.76 g, 1.5 eq) and $Na_2CO_3$ (4.39 g, 0.75 eq.). The reaction generated a lot of solid in 1min., thus diluted with ethanol-water (1:1, 60 mL) and stirred for 1 h. The reaction solution was poured into saturated NaCl (100 mL), and then extracted with ethyl acetate twice (300 mL). Organic extracts were washed with said $NaHCO_3$(100 mL×2), dried (anh. $Na_2SO_4$), filtered and concentrated to yield white powder (11.34 g, syn, anti mixture of oximes).

Example 2

Synthesis of (2S)-2-(t-Butoxycarbonyl)amino-1-chloro-3-methyl-butane-1-one Oxime N-t-butoxy-carbonyl-(S)-valinal oxime (11.34 g) in DMF (100 mL) was treated with NCS (7.75 g) and stirred in warm water bath (~40° C.) for 1 h. After removal of DMF, the residue was extracted with ethyl acetate-hexanes (1:1, 150 mL), washed with water (100 mL×3), dried (anh. $Na_2SO_4$), filtered and concentrated to give 13.69 g of the title compound.

Example 3

Synthesis of 4-(9-Fluorenylmethoxycarbonyl)amino-(4S)-5-hydroxy-pentanoic Acid t-Butyl Ester To a solution of N-(9-fluorenylmethoxycarbonyl)-γ-t-butyl glutamic acid (8.51 g, 20.0 mmol) and NMM (2.42 mL, 1.1 eq) in dry THF (110 mL) under $N_2$ at 0° C. was added isobutyl chloroformate (2.72 mL, 1.05 eq). After 20 min., the reaction e was filter-added to a solution of $NaBH_4$ (1.5 g) in THF (120 mL)-MeOH (30 mL) at $-78°$ C. under $N_2$ and rinsed with dry THF (20 mL). After stirring for 2.5 h at $-78°$ C., the reaction was quenched with acetic acid (13 mL). After concentrating to ~50 mL, the residue was dissolved in ethyl acetate-hexanes (200 mL, 1:1), washed with water (150 mL×2). Aqueous layer was re-extracted with ethyl acetate-hexanes (150 mL, 1:1). Combined extract was washed with sat'd $NaHCO_3$ (150 mL×2), dried (anhydrous $Na_2SO_4$), filtered and concentrated to give 8.30 g of the title compound as glasslike solid. The crude alcohol was used directly.

$^1$H-NMR (500 MHz, $CDCl_3$) δ 7.77 (2H, d, J=7.3 Hz), 7.66 (2H, d, J=7.8 Hz), 7.41 (2H, t, J=7.3 Hz), 7.31 (2H, pseudo t, J=7.8, 7.3 Hz), 5.18 (NH, d), 4.41 (2H, m), 4.22 (1H, m), 3.72–3.57 (3H, m), 2.33 (2H, m), 1.93–1.77 (2H, m), 1.45 (9H, s).

Example 4

Synthesis of 4-(9-Fluorenylmethyloxycarbonyl)amino-(4S)-5-chloro-5-hydroxyimino-pentanoic Acid t-Butyl Ester To a solution of DMSO (3.0 mL) in dry $CH_2Cl_2$ (100 mL) at $-65°$ C. under $N_2$ was added oxalyl chloride (2.10 mL, 1.2 eq) slowly. After 15 min., a solution of 4-(9-fluorenylmethoxycarbonyl)amino-(4S)-5-hydroxypentanoic acid t-butyl ester (8.30 g, 20 mmol) in $CH_2Cl_2$ (50 mL) was added and rinsed with dry $CH_2Cl_2$ (20 mL). The resulting solution was stirred for 2 h at $-40$~$-50°$ C. EtN(i-Pr)$_2$ (10.45 mL, 3.0 eq) was added thereto and the reaction solution was slowly warmed up to $-10°$ C. with TLC checking (conversion to aldehyde is relatively slow, ~1 h). The reaction mi ctue was diluted with hexanes (300 mL), washed with water(150 mL), with 1N-$KHSO_4$ (×3, total 500 mL), dried with anh. $Na_2SO_4$, filtered and concentrated to give the corresponding aldehyde.

The crude aldehyde in ethanol(60 mL)-$CH_2Cl_2$ (30 mL)-water(10 mL) at 0° C. was treated with $H_2OH.HCl$ (2.08 g, 1.5 eq) and $Na_2CO_3$ (1.60 g, 0.75 eq). The reaction was stirred at room temperature for 30 min, then water (10 mL) was added and stirred for additional 1 h. The reaction was stirred further(1 h) with additional $H_2NOH.HCl$ (400 mg) and $Na_2CO_3$ (320 mg). Most of the volatiles were removed in vacuo, and the residue was taken up with ethyl acetate (200 mL), washed with water(100 mL), sat'd $NaHCO_3$ (100 mL), dried (anh. $Na_2SO_4$), filtered and concentrated to give the desired oxime (8.30 g, syn+anti) as white powder.

The crude oxime in DMF (35 mL) was treated with NCS (2.67 g, 20.0 mmol). The reaction was stirred in warm (40° C.) bath for 1 h. After removal of the DMP in high vacuum rotary evaporator, the residue was taken up with hexane-ethyl acetate (1:1, 150 mL), washed with water (100 mL×3), dried (anh $Na_2SO_4$), filtered and concentrated to give the title compound (9.25 g, syn+anti).

$^1$H-NMR (500 MHz, $CDCl_3$) δ 8.88 (1H, s), 7.75 (2H, d, J=7.3 Hz), 7.57 (2H, m), 7.39 (2H, t, J=7.32 Hz), 7.30 (2h, pseudo t, J=7.8,7.3 Hz), 5.46 (1H, d), J=9.3 Hz), 4.63 (1H, m), 4.43–4.38 (2H, m), 4.19 (1H, m), 2.3 (2H, m), 2.03 (2H, m), 1.43 (9H, s). (NMR data reported for major isomer.)

The Following compounds were prepared in the same manner as the above examples.

1-chloro-3-methyl-(2S)-2-phenylmethyloxycarbonylamino-butane-1-one oxime, 3-(t-butoxycarbonylamino)-(3S)-4-chloro-4-hydroxyimino-butanoic acid methyl ester, 3-(phenylmethyloxycarbonylamino)-(3S)-4-chloro-4-hydroxyimino-butenoic acid t-butyl ester, and 3-(9-fluorenylmethyloxycarbonylamino)-(3S)-4-chloro-4-hydroxyimino-butanoic acid t-butyl ester.

(B) Synthesis of Acrylate Derivatives (Examples 5 to 8)

Example 5

Synthesis of Ethyl 2-Acetoxymethylacrylate

A solution of ethyl 2-hydroxymethyl acrylate (17.3 g, 133 mmol, purity ~70%, ref: Villieras, J. and Rambaud, M.

Synthesis, 1982, 914) in dry CH$_2$C$_2$ (200 mL) under N$_2$ at 0° C. was treated with acetic anhydride (18.8 mL, 1.5 eq) and triethyl amine (37 mL, 2.0 eq). After overnight stirring at room temperature, the reaction was diluted with hexanes (400 mL), washed with sat'd NaHCO$_3$ (300 mL×2), dried (anh Na$_2$SO$_4$), filtered and concentrated Simple distillation gave 4.6 g of the title compound as clear liquid. NMR analysis showed ~70% purity.

$^1$H-NMR (500 MHz, CDCl$_3$) δ 6.36 (1H, s), 5.84 (1H, s), 4.81 (2H, s), 4.25 (2H, q, J=7.3 Hz), 2.11 (3H, s), 1.31 (3H, t, J=7.3 Hz).

Example 6

Synthesis of Ethyl 2-Phenoxymethylacrylate

A solution of ethyl 2-bromomethylacrylate (2.00 g, 10.4 mmol, ref: Villieras, J. and Rambaud, M. Synthesis, 1982, 914) and phenol(975 mg, 1.0 eq) in dry THF (20 mL) under N$_2$ at 0° C. was treated with anhydrous K$_2$CO$_3$ (1.43 g, 1.0 mol eq). No reaction was observed for 1 h. Anhydrous DMF (20 mL) was added and stirred for 2 h at 0° C. and for 1 h at room temperature. After evaporation of DMF, water(100 mL) was added, and the reaction was extracted with ethyl acetate (100 mL×2). The organic extract was washed with brine (100 mL), dried (anh. Na$_2$SO$_4$), filtered and concentrated. Flash chromatography (40% CH$_2$Cl$_2$/hexanes) gave 1.712 g (80%) of the title compound.

$^1$H-NMR (500 MHz, CDCl$_3$) δ 7.30 (2H, yt, J=7.3 Hz), 6.99–6.96 (3H, m), 6.41 (1H, s), 6.01 (1H, s), 4.78 (2H, s), 4.27 (2H, q, J=7.33 Hz).

Example 7

Synthesis of Ethyl 2-Benzylacrylate

To a solution of bromobenzene (7.15 g, 45.5 mmol) in THF (30 mL) was added n-BuLi (16.6 mL, 2.5 M in Hexane, 41.4 mmol) under N$_2$ at –78° C.

It was stirred for 10 min. To a suspension of CuCN (3.71 g, 41.4 mmol) in THF (30 mL) was added lithiated benzene solution via cannula under N$_2$ at –78° C. The reaction mixture was stirred for another 10 min. at –78° C. and ethyl 2-bromomethyl acrylate (4.00 g, 20.7 mmol) in THF was added. The reaction mixture was warmed up to room temperature slowly and quenched with 2N HCl. All precipitates were filtered off and the filtrate was diluted with hexanes (400 mL), washed with sat'd NaHCO$_3$ (300 mL×2), dried (anh Na$_2$SO$_4$), filtered and concentrated. Flash chromatography (2% ethyl acetate-hexanes) gave 3.04 g(77%) of the title compounds.

$^1$H-NMR (500 MHz, CDCl$_3$) δ 7.34–7.22 (5H, m), 6.26 (1H, s), 5.48 (1H, s), 4.22 (2H, q, J=6.3 Hz), 3.66 (2H, s), 1.29 (3H, q, J=6.3 Hz).

Example 8

Synthesis of Ethyl 2-(4-Bromophenyl)acrylate

The title compound was prepared according to the known procedure (Helvetica Chimica Acta 1986, 69 2048).

$^{1H-NMR}$ (500 MHz, CDCl$_3$) δ 7.46 (2H, d), 7.29 (2H, d), 6.37 (1H, s), 5.90 (1H, s), 4.29 (2H, q), 1.33 (3H, t).

The following compounds were similarly prepared.
Ethyl 2-(1-Naphthyl)acrylate $^1$H-NMR (500 MHz, CDCl$_3$) δ 7.86 (2H, t, J=7.3 Hz), 7.44 (1H, d, J=8.8 Hz), 7.48–7.43 (3H, m), 7.37 (1H, d, J=6.8 Hz), 6.70 (1H, d, J=2.0 Hz), 5.89 (1H, d, J=2.0 Hz), 4.22 (2H, q, J=7.3 Hz), 1.21 (3H, t, J=7.3 Hz), Ethyl 2-(2-Naphthyl)acrylate $^1$H-NMR (500 MHz, CDCl$_3$) δ 7.95 (1H, s), 7.90–7.86 (3H, m), 7.59–7.52 (3H, m), 6.47 (1H, d, J=1.0 Hz), 6.06 (1H, d, J=1.0 Hz), 4.38 (2H, q, J=6.8 Hz), 1.40 (3H, t, J=6.8 Hz).

Ethyl 2-Butyl Acrylate $^1$H-NMR (500 MHz, CDCl$_3$) δ 6.11 (s, 1H), 5.49 (d, J=1.4 Hz, 1H), 4.19 (q, J=6.9 Hz, 2H), 2.29 (m, 2H), 1.45–1.28 (m, 7H), 0.90 (t, J=7.3 Hz, 3H).

Ethyl 2-Propyl Acrylate $^1$H-NMR (500 MHz, CDCl$_3$) δ 6.12 (d, J=0.9 Hz, 1H), 5.49 (d, J=1.4 Hz, 1H), 4.20 (q, J=6.9 Hz, 2H), 2.27 (m, 2H), 1.49 (m, 2H), 1.29 (t, J=7.3 Hz, 3H), 0.92 (t, J=7.3 Hz, 3H).

Ethyl 2-Ethyl Acrylate $^1$H-NMR (500 MHz, CDCl$_3$) δ 6.11 (d, J=0.9 Hz, 1H), 5.50 (s, 1H), 4.20 (q, J=6.9 Hz, 2H), 2.32 (m, 2H), 1.29 (t, J=6.9 Hz, 3H), 1.07 (t, J=7.4 Hz, 3H).

Ethyl 2-Pentyl Acrylate $^1$H-NMR (300 MHz, CDCl$_3$) δ 6.12 (s, 1H), 5.50 (s, 1H), 4.21 (q, J=7.1 Hz, 2H), 2.29 (m, 2H), 1.51–1.13 (m, 9H), 0.89 (t, J=6.8 Hz, 3H).

(C) General Procedure for Isoxazoline Synthesis
(Examples 9 and 10)

Example 9

Synthesis of 3-((1S)-1-Phenylmethyloxycarbonylamino-2-methyl-propyl)-5-phenoxymethyl-4,5-dihydro-isoxazole-5-carboxylic Acid Ethyl Ester A solution of (2S)-2-phenylmethyloxycarbonylamino-1-chloro-3-methyl-butane-1-one oxime (640 mg, 2.25 mmol) and ethyl 2-phenoxymethylacrylate (464 mg) in dry ether(10 mL) under N$_2$ at –78° C. was treated with triethylamine (627 uL, 2.0 eq). The reaction was stirred overnight, allowing to warm up to room temperature slowly. Water(100 mL) was added, and the reaction was extracted with ethyl acetate (100 mL×2), washed with water(100 mL), dried (anh. Na$_2$SO$_4$), filterd and concentrated. Flash chromatography (15% ethyl acetate-hexanes) gave 851 mg(83%) of the title compounds as 1:1 mixture of diastereomers.

$^1$H-NMR (500MHz, CDCl$_3$) δ 7.34 (7H, m), 6.98 (1H, t, J=7.3 Hz), 6.89 (2H, d, J=7.7 Hz), 5.61 (1H, d, J=9.3 Hz), 5.15–5.08 (2H, m), 4.50 (1H, br s), 4.33–4.22 (4H, m), 3.60–3.54 (1H, m), 3.32–3.27 (1H, m), 2.10 (1H, m), 1.29 (3H, m), 1.02–0.94 (6H, m).

The following compounds were prepared similarly:
Ethyl 3-[(1S)-1-Phenylmethyloxycarbonylamino-2-methyl-propyl]-5-phenylmethyl-4,5-dihydro-isoxazole-5-caboxylate (Diastereomeric)

$^1$H-NMR (500 MHz, CDCl$_3$) δ 7.45–7.15 (m, 10H), 5.07 (m, 2.5H), 4.90 (d, 0.5H), 4.30–4.18 (m, 3H), 3.36–2.88 (m, 4H), 1.95–1.80 (m, 1H), 1.27 (m, 3H), 0.86–0.55 (m, 6H).

3-[(1S)-1-t-Butoxycarbonylamino-2-methyl-propyl]-5-(2-naphthyl)4,5-dihydro-isoxazole-5-carboxylic Acid Ethyl Ester $^1$H-NMR (500 MHz, CDCl$_3$) δ 7.97 (1H, s), 7.86–7.82 (3H, m), 7.52–7.48 (3H, m), 4.93 (1H, br), 4.37 (1H, m), 4.25–4.18 (2H, m), 4.10–4.05 (1H, two doublets, J=17.1, 17.6 Hz), 3.28–3.22 (1H, two doublets, J=17.1, 17.1 Hz), 2.05 (1H, m), 1.43 ((H, s), 1.24–1.20 (3H, m), 0.98–0.91 (6H, m).

3-[(1S)-1-t-Butoxycarbonylamino-2-methyl-propyl]-5-phenylmethyl-4,5-dihydro-isoxazole-5-carboxylic Acid Ethyl Ester (~1:1 Diastereomers)

$^1$H-NMR (500 MHz, CDCl$_3$) δ 7.25 (5H, m), 4.82 and 4.60 (1H, two m), 4.25–4.15 (3H, m), 3.38–3.29 (2H, m), 3.10 (1H, m), 2.90 (1H, m), 1.43 and 1.42 (9H, two s), 1.27 (3H, m), 0.90–0.80 (6H, m).

5-Acetoxymethyl-3-[(1S)-1-t-butoxy-carbonylamino-2-methyl-propyl]-4,5-dihydro-isoxazole-5-carboxylic Acid Ethyl Ester $^1$H-NMR (500 MHz, CDCl$_3$) δ 4.93 (1H, br), 4.44–4.26 (5H, m), 3.50 (1H, m), 3.10 (1H, m), 2.08 (4H, s+br 1H), 1.46 (9H, s), 1.32–1.30 (3H, m), 1.02–0.96 (6H, m).

Ethyl 3-[2-Methyl-(1S)-1-(tert-butoxycarbonylamino)-propyl]-5-butyl-4,5-dihydro-isoxazole-5-caboxylate (Diastereomeric Mixture)

$^1$H-NMR (500 MHz, CDCl$_3$) δ 4.96 & 4.87 (two br s, 1H), 4.34–4.18 (m, 3H), 3.42–3.36 (m, 1H), 2.90–2.83 (m, 1H), 2.02 (m, 1H), 1.91 (m, 2H), 1.43 (s, 9H), 1.37–1.26 (m, 7H), 0.98–0.87 (m, 9H).

Ethyl 3-[2-Methyl-(1S)-1-(tert-butyloxycarbonylamino)-propyl]-5-propyl-4,5-dihydro-isoxazole-5-carboxylate (Diastereomeric Mixture)

$^1$H-NMR (500 MHz, CDCl$_3$) δ 4.96–4.86 (m, 1H), 4.33–4.18 (m, 3H), 3.42–3.36 (m, 1H), 2.90–2.83 (m, 1H), 2.02 (m, 1H), 1.89 (m, 2H), 1.43 (s, 9H), 1.29 (m, 5H), 0.98–0.87 (m, 9H).

Methyl 3-[2-Methyl-(1S)-1-(tert-butyloxycarbonylamino)-propyl]-5-methoxy-methyl-4,5-dihydro-isoxazole-5-carboxylate (Diastereomeric Mixture)

$^1$H-NMR (500 MHz, CDCl$_3$) δ 4.92 (m, 1H), 4.35 (m, 1H), 3.80 & 3.79 (two s, 3H), 3.40 (s, 3H), 3.88–3.13 (m, 4H), 2.04 (m, 1H), 1.44 (s, 9H), 0.99–0.91 (m, 6H).

Ethyl 3-[2-Methyl-(1S)-1-(tert-butyloxycarbonylamino)-propyl]-5-n-pentyl-4,5-dihydro-isoxazole-5-carboxylate (Diastereomeric Mixture)

$^1$H-NMR (500 MHz, CDCl$_3$) δ 4.95 & 4.88 (two br s, 1H), 4.30–4.17 (m, 3H), 3.42–3.36 (m, 1H), 2.89–2.83 (m, 1H), 2.02 (m, 1H), 1.90 (m, 2H), 1.43 (s, 9H), 1.28 (m, 9H), 0.98–0.85 (m, 9H).

Ethyl 3-[2-Methyl-(1S)-1-(tert-butyloxycarbonylamino)-propyl]-5-ethyl-4,5-dihydro-isoxazole-5-carboxylate (Diastereomeric Mixture)

$^1$H-NMR (500 MHz, CDCl$_3$) δ 4.96 & 4.88 (two br s, 1H), 4.3–4.18 (m, 3H), 3.42–3.36 (m, 1H), 2.89–2.80 (m, 1H), 2.03 (m, 1H), 1.94 (m, 2H), 1.43 (s, 9H), 1.29 (m, 3H), 0.97–0.86 (m, 9H).

Example 10

Synthesis of 3-[(1S)-1-(9-Fluorenylmethyloxycarbonylamino)-3-t-butoxycarbonyl-propyl]-5-methyl-4,5-dihydro-isoxazole-5-carboxylic Acid Methyl Ester A solution of 4-(9-fluorenylmethoxycarbonyl)amino-(4S)-5-chloro-5-hydroxy-imino-pentanoic acid t-butyl ester (3.44 g, 7.50 mmol) and methyl methacrylate (2.40 mL, 3.0 eq) in dry ether under N$_2$ at –78° C. was treated with EtN(i-Pr)$_2$ (1.96 mL, 1.5 eq). Similar treatment as described previously followed by flash chromatography with 25–30% ethyl acetate/hexanes gave 3.46 g (89% overall) of the title compound as diastereomeric mixture.

$^1$H-NMR (500 MHz, CDCl$_3$) δ 7.77 (2H, d, J=7.3 Hz), 7.59 (2H, d, J=7.3 Hz), 7.40 (2H, t, J=7.3 Hz), 7.31 (2H, t, J=7.3 Hz), 5.34 (1H, m), 4,58–4.38 (3H, m), 4.21 (1H, m), 3.78 (3H, s), 3.48 (1H, m), 2.90–2.81 (1H, m), 2.42–2.27 (2H, m), 2.18 (1H, m), 1.93 (1H, m), 1.63 (3H, s), 1.45 (9H, s).

(D) Transformations of Isoxazolines (Deprotection, Introduction of P$_4$ Group, Hydrolysis of Ester Group) (Examples 11 and 12)

Example 11

Synthesis of 3-{2-Methyl-(1S)-1-(naphthalene-2-carbonylamino)-propyl}-5-phenoxymethyl-4,5-dihydro-isoxazole-5-carboxylic Acid Ethyl Ester A solution of 3-{(1S)-1-(t-butoxycarbonylamino)-2-methyl-propyl}-5-phenoxymethyl-4,5-dihydro-isoxazole-5-carboxylic acid ethyl ester (2.00 g, 4.76 mmol) in dry CH$_2$Cl$_2$ (10 mL) at 0° C. under N$_2$ was treated with TFA (6 mL) and stirred for 1.5 h. After removal of volatiles, the residue was taken up with ethyl acetate (200 mL), washed with sat'd NaHCO$_3$(100 mL×2), dried (anh Na$_2$SO$_4$), filtered and concentrated. To a solution of the crude product, EDC (1.09 g, 1.2 eq), 2-naphthoic acid (983 mg, 1.2 eq) and HOBt (771 mg, 1.2 eq) in DMF (20 mL) at 0° C. was added triethylamine (663 uL, 1.0 eq). The reaction was stirred overnight at room temperature. After removal of volailes in vacuo, the residue was taken up with ethyl acetate (250 mL), washed with water(100 mL), sat'd NaHCO$_3$ (100 mL×2), dried (anh Na$_2$SO$_4$), filtered and concentrated. Flash chromatography with 25–33% ethyl acetate/hexanes gave 2.04 g (90%) of the title compound.

$^1$H-NMR (500 MHz, CDCl$_3$) δ 8.30 (1H, s), 7.93–7.84 (4H, m), 7.58–7.52 (2H, m), 7.29–7.22 (2H, m), 7.00–6.81 (4H, m), 5.06–5.01 (1H, m), 4.36–4.24 (4H, m), 3.68–3.61 (1H, m), 3.43–3.39 (1H, m), 2.28 (1H, m), 1.31–1.26 (3H, m), 1.12–1.05 (6H, m).

Hydrolysis of isoxazoline 5-carboxylic acid ester. The above compound (2.04 g) in distilled THF (40 mL) (not completely soluble) was treated with 1N—NaOH(5.2 mL, 1.2 eq). After 4 h (~50% completion), additional 1N—NaOH (1.0 mL) was added. After stirring overnight, the reaction was neutralized with concentrated 1N-HCl. The residue was taken up with CH$_2$Cl$_2$ (>700 mL), washed with water, dried (anh Na$_2$SO$_4$), filtered and concentrated to give 1.948 g (103%) of the free carboxylic acid, which was used directly in next step.

The following compounds were prepared similarly:

3-{2-Methyl-(1S)-1-(naphthalene-1-carbonylamino)-propyl}-5-phenoxymethyl-4,5-dihydro-isoxazole-5-carboxylic Acid Ethyl Ester $^1$H-NMR (500 MHz, CDCl$_3$) δ 8.23 (1H, d, J=8.3 Hz), 7.93–7.86 (2H, m), 7.66 (1H, m), 7.54–7.42 (3H, m), 7.29–7.25 (2H, m), 7.00–6.90 (3H, m), 6.49 (1H, m), 5.13–5.09 (1H, m), 4.40–4.26 (4H, m), 3.69–3.64 (1H, m), 3.44–3.41 (1H, m), 2.28 (1H, m), 1.32–1.01 (9H, m).

3-{2-Methyl-(1S)-1-(naphthalene-2-carbonylamino)-propyl}-4,5-dihydro-isoxazole-5-carboxylic Acid Ethyl Ester $^1$H-NMR (500MHz, CDCl$_3$) δ 8.30 (1H, s), 7.94–7.83 (4H, m), 7.59–7.53 (2H, m), 6.80–6.70 (NH, two d), 5.07–5.03 (2H, m), 4.28–4.21 (2H, m), 3.37–3.33 (2H, m), 2.28 (1H, m), 1.34–1.25 (3H, m), 1.12–1.02 (6H, m).

3-[(1S)-1-(1-Naphthalenecarbonylamino)-2-methyl-propyl]-5-phenylmethyl-4,5-dihydro-isoxazole-5-carboxylic Acid Ethyl Ester (Diastereomeric)

$^1$H-NMR (500 MHz, CDCl$_3$) δ 8.28 (d, J=7.8 Hz, 1H), 7.94–7.86 (m, 2H), 7.61–7.11 (m, 9H), 6.36 (d, J=9.3 Hz, 0.5H), 6.09 9d, J=9.3 Hz, 0.5H), 4.94–4.85 (m, 1H), 4.27–4.21 (m, 2H), 3.49–2.98 (m, 4H), 2.15 & 1.97 (two m, 1H), 1.30–1.26 (m, 3H), 1.03–0.59 (m, 6H).

Ethyl 3-[(1S)-1-Phenethylcarbonylamino-2-methyl-propyl]-5-phenylmethyl-4,5-dihydro-isoxazole-5-carboxylate (Diastereomeric)

$^1$H-NMR (500 MHz, CDCl$_3$) δ 7.28–7.17 (m, 10H), 5.74 & 5.50 (two d, J=9.3 Hz, NH), 4.58–4.52 (m, 1H), 4.24–4.20 (m, 2H), 3.34–3.25 (m, 2H), 3.11–2.82 (m, 4H), 2.52–2.45 (m, 2H), 1.93 & 1.75 (two m, 1H), 1.29–1.25 (m, 3H), 0.79–0.41 (m, 6H).

3-[(1S)-1-(1-Naphthalenesulfonylamino)-2-methyl-propyl]-5-phenylmethyl-4,5-dihydro-isoxazole-5-carboxylic Acid Ethyl Ester (Diastereomeric)

$^1$H-NMR (500 MHz, CDCl$_3$) δ 8.68–8.64 (m, 1H), 8.29–8.25 (m, 1H), 8.07 (m, 1H), 7.93 (m, 1H), 7.71–7.52

(m, 3H), 7.23–6.98 (m, 5H), 5.27 & 5.19 (two m, 1H), 4.12–4.07 (m, 2H), 3.75 & 3.66 (two m, 1H), 3.16–2.43 (m, 4H), 1.77–1.62 (m, 1H), 1.25–1.16 (m, 3H), 0.86–0.57 (m, 6H).

3-[(1S)-1-(Indole-3-yl-ethylcarbonylamino)-2-methyl-propyl]-5-phenylmethyl-4,5-dihydro-isoxazole-5-carboxylic Acid Ethyl Ester (Diastereomeric)

$^1$H-NMR (500 MHz, CDCl$_3$) δ 8.16–8.12 (m, 1H), 7.62–7.56 (m, 1H), 7.36–6.94 (m, 9H), 5.71 (d, J=9.3 Hz, 0.5H), 5.42 (d, J=8.8 Hz, 0.5H), 4,56–4,50 (m, 1H), 4.25–4.17 (m, 2H), 3.30–2.51 (m, 8H), 1.89–1.70 (m, 1H), 1.28–1.24 (m, 3H), 0.73–0.41 (m, 6H).

3-[(1S)-1-(Indole-3-yl-methylcarbonylamino)-2-methyl-propyl]-5-phenylmethyl-4,5-dihydro-isoxazole-5-carboxylic Acid Ethyl Ester (Diastereomeric)

$^1$H-NMR (500 MHz, CDCl$_3$) δ 8.56 & 8.52 (two br s, 1H), 7.55–7.05 (m, 10H), 5.98–5.91 (m, 1H), 4,57 (m, 1H), 4.22–4.15 (m, 2H), 3.73 (m, 2H), 3.28–2.79 (m, 4H), 1.87–1.68 (m, 1H), 1.27–1.20 (m, 3H), 0.75–0.34 (m, 6H).

3-[(1S)-1-(Cinnamoylamino)-2-methyl-propyl]-5-phenylmethyl-4,5-dihydro-isoxazole-5-carboxylic Acid Ethyl Ester (Diastereomeric)

$^1$H-NMR (500 MHz, CDCl$_3$) δ 7.61–7.23 (m, 11H), 6.40–6.34 (m, 1H), 6.06 (d, J=8.8 Hz, 0.5H), 5.81 (d, J=9.3 Hz, 0.5H), 4.76–4.69 (m, 1H), 4.26–4.19 (m, 2H), 3.42–2.94 (m, 4H), 2.06 & 1.88 (two m, 1H), 1.28–1.24 (m, 3H), 0.93–0.57 (m, 6H).

3-[(1S)-1-(Phenylmethylsufonylamino)-2-methyl-propyl]-5-phenylmethyl-4,5-dihydro-isoxazole-5-carboxylic Acid Ethyl Ester (Diastereomeric)

$^1$H-NMR (500 MHz, CDCl$_3$) δ 7.35–7.16 (m, 10H), 4.66–4.61 (m, 1H), 4.25 (m, 2H), 4.11–3.84 (m, 3H), 3.71–2.82 (m, 4H), 1.80 & 1.70 (two m, 1H), 1.28 (m, 3H), 0.85–0.58 (m, 6H).

Methyl 3-[2-Methyl-(1S)-1-(4-tert-butyloxycarbonylbutanoylamino)-propyl]-5-methyl-4,5-dihydro-isoxazole-5-carboxylate (Diastereomeric Mixture)

$^1$H-NMR (500 MHz, CDCl$_3$) δ 6.05–5.99 (two d, 1H), 4.71 (m, 1H), 3.77 (s, 3H), 3.49–3.44 (m, 1H), 2.87–2.80 (m, 1H), 2.27 (m, 4H), 2.07 (m, 1H), 1.92 (m, 2H), ~1.6 (s, 3H), 1.43 (s, 9H), 1.29 (m, 3H), 0.99–0.86 (m, 9H).

Ethyl 3-[2-Methyl-(1S)-1-(3-tert-butyloxycarbonylbutanoylamino)-propyl]-5-ethyl-4,5-dihydro-isoxazole-5-carboxylate (Diastereomeric Mixture)

$^1$H-NMR (500 MHz, CDCl$_3$) δ 6.20–6.15 (two d, 1H), 4.68 (m, 1H), 4.21 (m, 2H), 3.40–3.36 (m, 1H), 2.90–2.82 (m, 1H), 2.57 (m, 2H), 2.46 (m, 2H), 2.07 (m, 1H), 1.94 (m, 2H), 1.43 (s, 9H), 1.29 (m, 3H), 0.96–0.88 (m, 9H).

Ethyl 3-[2-Methyl-(1S)-1-(3-tert-butyloxycarbonylproanoylamino)-propyl]-5-n-pentyl-4,5-dihydro-isoxazole-5-carboxylate (Diastereomeric Mixture)

$^1$H-NMR (500 MHz, CDCl$_3$) δ 6.18–6.13 (two d, 1H), 4.68 (m, 1H), 4.23 (m, 2H), 3.41–3.36 (m, 1H), 2.90–2.82 (m, 1H), 2.57 (m, 2H), 2.46 (m, 2H), 2.08 (m, 1H), 1.88 (m, 2H), 1.43 (s, 9H), 1.28 (m, 9H), 0.96–0.85 (m, 9H).

Methyl 3-[2-Methyl-(1S)-1-(3-tert-butyloxycarbonylproanoylamino)-propyl]-5-methoxymethyl-4,5-dihydro-isoxazole-5-caboxylate (Diastereomezic Mixture)

$^1$H-NMR (500 MHz, CDCl$_3$) δ 6.17 (m, 1H), 4.71 (m, 1H), 3.78 (s, 3H), 3.72–3.65 (m, 2H), 3.39 (two s, 3H), 3.39–3.34 (m, 1H), 3.17–3.12 (m, 1H), 2.57 (m, 2H), 2.46 (m, 2H), 2.08 (m, 1H), 1.43 (s, 9H), 0.97–0.88 (m, 6H).

3-[2-Methyl-(1S)-1-amino-propyl]-5-(2-naphthyl)-4,5-dihydro-isoxazole-5-carboxylic Acid Ethyl Ester (~1.3:1 Diastereomers)

$^1$H-NMR (500 MHz, CDCl$_3$) δ 7.99 (1H, s), 7.86–7.82 (3H, m), 7.53–7.49 (3H, m), 4.25–4.02 (3H, m), 3.55–3.48 (1H, two d, J=7.3, 6.8 Hz), 3.35 (0.45H, d, J=17.1 Hz), 3.19 (0.55H, d, J=17.1 Hz), 1.78 (1H, m), 1.22 (3H, t, J=7.3 Hz), 0.96–0.82 (6H, m).

Example 12

Synthesis of 3-{(1S)-1-(2-Naphthoylamino)-3-t-butoxycarbonyl-propyl}-5-methyl-4,5-dihydro-isoxazole-5-carboxylic Acid Methyl Ester A solution of 3-[(1S)-1-(9-fluorenylmethyloxycarbonylamino)-3-t-butoxycarbonyl-propyl]-5-methyl-4,5-dihydro-isoxazole-5-carboxylic acid methyl ester (440 mg, 0.842 mmol) in DMF (8.0 mL) at room temperature was treated with piperidine (2.5 mL) for 5 min. After concentration, the residue was dissolved in DMF (10 mL), and treated with 2-naphthoic acid (174 mg, 1.2 eq), EDC (210 mg, 1.3 eq), HOBt (148 mg, 1.3 eq) and triethylamine (0.35 mL, 3.0 eq), then sired overnight (0° C. to room temperature). Usual workup followed by chromatography gave 133 mg of the title compound and 260 mg (~50% purity) mixture.

$^1$H-NMR (500 MHz, CDCl$_3$) δ 8.33 (1H, s), 7.92–7.83 (4H, m), 7.58–7.48 (2H, m), 7.34 (1H, d, J=7.8 Hz), 5.04 (1H, m), 3.78 and 3.74 (3H, two s), 3.62–3.53 (1H, two d, J=17.1, 17.6 Hz), 3.00–2.96 (1H, two d, J=17.1, 17.6 Hz), 2.56–2.08 (4H, m), 1.63 and 1.59 (3H, two s), 1.41 and 1.40 (9H, two s).

(E) Synthesis of Aspartic Acid Derivatives (Examples 13 to 18)

Example 13

Synthesis of N-Phenylmethyloxycarbonyl-β-t-butyl Aspartic Acid (N-Methoxy)methyl Amide A solution of N-benzyloxycarbonyl-β-t-butyl aspartic acid (2.0 g, 6.2 mmol), N,O-dimethylhydroxylamine hydrochloride (724 mg, 1.2 eq) and HOBt (1.00 g, 1.2 eq) in DMF (20 mL) at 0° C. was treated with EDC (1.42 g, 1.2 eq) and triethylamine (1.29 mL, 1.5 eq). After stirring overnight (0° C. to room temperature), the reaction was diluted with water(100 mL), extracted with ethyl acetate-hexanes (1:1, 100 mL×2), washed with water(100 mL), dried (anh Na$_2$SO$_4$), filtered and concentrated. Flash chromatography with ethyl acetate-hexanes (3:7) gave 2.039 g (90%) of the title compound.

$^1$H-NMR (500 MHz, CDCl$_3$) δ 7.36–7.31 (5H, m), 5.70 (1H, br), 5.16–5.08 (3H, m), 3.80 (3H, s), 3.23 (3H, s), 2.74–2.71 (1H, m), 2.59–2.57 (1H, m), 1.43 (9H, s).

Example 14

Synthesis of β-t-Butyl Aspartic Acid N,O-Dimethylhydroxylamine Amide

Conventional hydrogenolysis of N-phenylmethyloxycarbonyl-β-t-butyl aspartic acid (N-methoxy)methyl amide (H$_2$ balloon, 10% Pd/C, EtOH) gave the title compound (100%).

$^1$H-NMR (500MHz, CDCl$_3$) δ 4.13 (1H, m), 3.77 (3H, s), 3.22 (3H, s), 2.71–2.67 (1H, m), 2.42–2.38 (1H, m), 1.46 (9H, s).

Example 15

Synthesis of N-Phenylmethyloxycarbonyl-β-t-butyl Aspartic Acid Methyl Ester

Treatment of N-benzyloxycarbonyl-β-t-butyl aspartic acid with diazomethane/ether gave the desired methyl ester (100%).

¹H-NMR (500 MHz, CDCl₃) δ 7.35–7.27 (5H, m), 5.75 (1H, d), 5.13 (2H, s), 4.60 (1H, m), 3.75 (3H, m), 2.90 (1H, m), 2.76 (1H, m), 1.42 (9H, s).

Example 16

Synthesis of β-t-Butyl Aspartic Acid Methyl Ester Hydrochloride

Conventional hydrogenolysis of N-phenylmethyloxycarbonyl-β-t-butyl aspartic acid methyl ester (H₂ balloon, 10% Pd/C, EtOH-HCl) gave the desired product as hydrochloride salt.

Example 17

Synthesis of (3S)-3-Phenylmethyloxycarbonylamino-4-hydroxy-5-phenoxy-pentanoic Acid t-Butyl Ester A solution of N-phenylmethyloxycarbonyl-β-t-butyl-aspartic acid (5.03 g, 15.6 mmol), NMM (1.90 mL, 17.1 mmol) in dry THF (60 mL) under N₂ at −15° C. was treated with isobutyl chloroformate (2.12 mL, 16.3 mmol) and the resulting suspension was stirred for 20 min. To the mixture at 0° C. was added dry diazomethaneether (synthesized from 2.0 eq of 1-methyl-3-nitro-1-nitroso-guanidine, 60 mL) and stirred for 30 min. When the diazo ketone synthesis was completed (TLC analysis), 30% HBr/AcOH (6.42 mL, 2.0 eq) was introduced thereto (stirred for 30–60 min.) at 0° C. The reaction was extracted with ethyl acetate, washed with sat'd NaHCO₃ (×2), brine, dried (anh. Na₂SO₄), filtered and concentrated to give bromomethyl ketone derivative (6.4 g).

The bromomethyl ketone(4.36 g) and phenol (1.13 g, 1.1 eq) in DMF (18 mL) at room temperature were treated with freshly dried KF (1.58 g, 2.5 eq) and stirred for 2 h. Usual extractive workup gave crude phenoxy ketone. The crude phenoxy ketone in methanol (20 mL) at −78° C. was treated with NaBH₄ (412 mg) in MeOH (40 mL) (78° C. to room temperature, 2 h). The reaction was quenched with acetic acid. Usual extractive workup followed by flash chromatography (ethyl acetate-hexanes=1:5) gave 2.58 g (57%) of the title compound as diastereomeric mixture.

¹H-NMR (500 MHz, CDCl₁) δ 7.36–7.26 (7H, m), 6.98–6.87 (3H, m), 5.71–5.53 (NH, two d), 5.10 (2H, s), 4.24–3.92 (4H, m), 2.70–2.63 (2H, m), 1.44 and 1.43 (9H, two s).

The following compound was prepared similarly:
(3S)-3-Phenylmethyloxycarbonylamino-4-hydroxy-5-(1-naphthyl)oxypentanoic Acid t-Butyl Ester ¹H-NMR (500 MHz, CDCl₃) δ 8.21 (1H, m), 7.80 (1H, m), 7.50–7:33 (9H, m), 6.80 (1H, m), 5.73 and 5.55 (1H, two d, J=8.3 Hz), 5.10 (2H, s), 4.30–4.15 (4H, m), 2.76–2.69 (2H, m), 1.44 (9H, s).

Example 18

Synthesis of (3S)-3-Amino-4-hydroxy-5-phenoxy-pentanoic Acid t-Butyl Ester

Conventional hydrogenolysis of (3S)-3-phenylmethyloxycarbonylamino-4-hydroxy-5-phenoxy-pentanoic acid t-butyl ester (H₂ balloon, Pd/C, EtOH) gave the desired product (100%).

¹H-NMR (500 MHz, CDCl₃) δ 7.29–7.26 (2H, m), 6.97–6.90 (3H, m), 4.08–3.82 (3H, m), 3.43 (1H, m), 2.63–2.37 (2H+NH₂+OH, m), 1.46 and 1.45 (9H, two s).

The following compound was prepared similarly;
(3S)-3-Amino-4-hydroxy-5-(1-naphthyl)oxy-pentanoic Acid t-Butyl Ester ¹H-NMR (500 MHz, CDCl₃) δ 8.22 (1H, m), 7.80 (1H, m), 7.50–7.34 (4H, m), 6.84 (1H, m), 4.26–4.20 (2H, m), 4.03–3.94 (1H, m), 3.51 (1H, m), 2.70–2.40 (2H, m), 1.47 and 1.46 (9H, two s).

(F) Coupling of Isoxazoline Derivatives and Aspartic Acid Derivatives and Further Transformations Thereof (Examples 19 to 24)

Example 19

Synthesis of (2S)-2-{3-[(1S)-1-Phenylmethyloxycarbonylamino-2-methyl-propyl]-5-phenoxymethyl-4,5-dihydro-isoxazole-5-carbonyl-amino}-succinic Acid 4-t-Butyl Ester 1-(N-Methyl-N-methoxy)amide A solution of 3-[(1S)-1-phenylmethyloxycarbonylamino-2-methyl-propyl]-5-phenoxymethyl-4,5-dihydro-isoxazole-5-carboxylic acid ethyl ester (502 mg, 1.10 mmol) in THF (6.6 mL) was treated with 1N—NaOH (1.33 mL). After stirring for 2.5 h at room temperature, the reaction solution was quenched with 1N-HCl (1.33 mL), then concentrated in vacuo. The residue together with sat'd NaCl(50 mL+2–3 mL of 1N-HCl) was extracted with ethyl acetate (100 mL×2), dried (anh Na₂SO₄), filtered and concentrated to give 476 mg (10%) of 3-[(1S)-1-phenylmethyl-oxycarbonylamino-2-methyl-propyl]-5-phenoxymethyl-4,5-dihydro-isoxazole-5-carboxylic acid.

The crude acid (320 mg, 0.75 mmol) and β-t-butyl aspartic acid N-methyl-(N-methoxy)amide (209 mg, 1.2 eq) in DMF (5 mL) at 0° C. were treated with HOBt (122 mg, 1.2 eq), EDC (172 mg, 1.2 eq) and triethylamine 0.3 mL, 3.0 eq), and then stirred for 3 h (0° C. to room temperature). Concentration, conventional workup followed by flash chromatography gave less polar isomer (160 mg) and more polar isomer (213 mg, 33%).

More polar isomer: ¹H-NMR (500 MHz, CDCl₃) δ 7.64 (1H, d), 7.35–7.24 (7H, m), 6.95 (1H, t, J=7.3 Hz), 6.88 (2H, d, J=7.8 Hz), 5.55 (1H, d), 5.18–5.08 (3H, m), 4.44 (1H, m), 4.32–4.25 (2H, m), 3.75 (3H, s), 3.32–3.25 (2H, m), 3.12 (3H, s), 2.77–2.71 (1H, m), 2.62–2.56 (1H, m), 2.12 (1H, m), 1.44 (9H, s), 1.03–2.91 (6H, m). Less polar isomer: ¹H-NMR (500 MHz, CDCl₃) δ 7.65 (1H, d, J=8.3 Hz), 7.36–7.23 (7H, m), 6.95 (1H, t, J=7.3 Hz), 6.88 (2H, d, J=8.3 Hz), 5.19–5.11 (4H, m), 4.46 (1H, m), 4.33–4.22 (2H, ABq, J=10.3 Hz), 3.75 (3H, s), 3.33 (2H, s), 3.23 (3H, s), 2.73 (1H, m), 2.57 (1H, m), 2.07 (1H, m), 1.43 (9H, s), 1.03–0.92 (6H, m).

Example 20

Synthesis of (3S)-3-{3[(1S)-1-phenylmethyloxycarbonylamino-2-methyl-propyl]-5-phenoxymethyl-4,5-dihydro-isoxazole-5-carbonyl-amino}-4-keto-pentanoic Acid t-Butyl Ester The title compound was obtained from treatment of excess MeMgBr (3.0M in ether, >3.0 eq) to a solution of less polar isomer of (2S)-2-{3-[(1S)-1-phenylmethyloxycarbonylamino-2-methyl-propyl]-5-phenoxymethyl-4,5-dihydro-isoxa-zole-5-carbonyl-amino}-succinic acid 4-t-butyl ester 1-(N-methyl-N-methoxy)amide (110 mg, 0.17 mmol) in THF (5 mL)+LiCl satuated THF (2 mL) at 0° C.—room temperature (44 mg, 43%).

From less polar isomer: ¹H-NMR (500 MHz, CDCl₃) δ 8.00 (1H, d, J=9.3 Hz), 7.36–7.24 (7H, m), 6.96 (1H, t, J=7.2 Hz), 6.87 (2H, d, J=8.3 Hz), 5.26 (1H, d, J=8.8 Hz), 5.12–5.09 (2H, m), 4.66 (1H, m), 4.43 (1H, d, J=9.8 Hz), 4.21 (1H, d, J=9.8 Hz0, 3.37–3.19 (2H, ABq, J=18.0 Hz), 2.88 (1H, m), 2.58 (1H, m), 2.25 (3H, s), 2.03 (1H, m), 1.42 (9H, s), 0.99–0.89 (6H, m).

Similar treatment of more polar isomer of (2S)-2-{3-[(1S)-1-phenylmethyl-oxy-carbonylamino-2-methyl-propyl]-5-phenoxymethyl-4,5-dihydro-isoxazole-5-carbonyl-amino}-succinic acid 4-t-butyl ester 1-(N-methyl-N-methoxy)amide (135 mg) gave 52 mg (41%) of the corresponding methyl ketone.

Example 21

Synthesis of (2S)-2-{3-[2-Methyl-(1S)-1-(naphthalene-2-carbonyl-amino)-propyl]-5-phenylmethyl-4,5-dihydro-isoxazole-5-carbonyl-amino}-succinic Acid 4-t-Butyl Ester 1-Methyl Ester A solution of 3-[2-methyl-(1S)-1-(naphthalene-2-carbonylamino)-propyl]-5-phenyl-methyl-4,5-dihydro-isoxazole-5-carboxylic acid (2.14 g, 5.07 mmol), aspartic acid β-t-butyl ester methyl ester hydrochloride (1.46 g, 1.2 eq), EDC (1.17 g, 1.2 eq) and HOBt (822 mg, 1.2 eq) in DMF (19 mL) was treated with triethylamine (2.12 mL, 3.0 eq), and stirred overnight. Conventional workup followed by flash chromatography (40–50% ethyl acetate-hexanes) gave the title compound (294 g, 94%) as a white foam.

¹H-NMR (500 MHz, CDCl₃) δ 8.30 and 8.25 (1H, two s), 7.96–7.79 (4H, m), 7.65–7.54 (3H, m), 7.31–7.18 (5H, m), 6.76 (0.5H, d, J=9.3 Hz), 6.43 (0.5H, d, J=8.8 Hz), 4.96–4.70 (2H, m), 3.71 and 3.60 (3H, two s), 3.45–3.14 (4H, m), 3.08–2.34 (2H, m), 2.15 (1H, m), 1.47 and 1.44 (9H, two s), 1.04–0.88 (6H, m).

The above compound was hydrolyzed according to the above described method (1N—NaOH in THF) to obtain the coresponding carboxylic acid (100%).

The following esters and free carboxylic acids were prepared similarly.

(2S)-2-{3-[2-Methyl-(1S)-1-(naphthalene-2-carbonylamino)-propyl]-5-phenoxymethyl-4,5-dihydro-isoxazole-5-carbonyl-amino}-succinic Acid 4-t-Butyl Ester 1-Methyl Ester ¹H-NMR (500 MHz, CDCl₃) δ 8.33 and 8.30 (1H, two s), 7.95–7.74 (5H, m), 7.59–7.53 (2H, m), 7.28–7.22 (2H, m), 6.99–6.89 (3.5H, m), 6.71 (0.5H, d, J=8.8 Hz), 5.08–5.01 (1H, m), 4.83–4.79 (1H, m), 4.39–4.29 (2H, m), 3.76 and 3.64 (3H, two s), 3.44 (2H, s), 2.97–2.93 (1H, m), 2.74–2.69 (1H, m), 2.34–2.23 (1H, m), 1.45 and 1.42 (9H, two s), 1.15–1.01 (6H, m).

Hydrolysis of the above compound gave free carboxylic acid.

(2S)-2-{3-[(1S)-1-(Phenylmethyloxycarbonyl)-amino-2-methyl-propyl]-4,5-dihydro-isoxazole-5-carbonyl-amino}-succinic Acid 4-t-Butyl Ester 1-Methyl Ester ¹H-NMR (500 MHz, CDCl₃) δ 7.59–7.49 (1H, m), 7.38–7.32 (5H, m), 5.25–4.95 (1H, m), 4.86 (1H, m), 4.48 (1H, m), 3.76 and 3.67 (3H, two s), 3.29 (2H, m), 2.92 (1H, m), 2.71–2.62 (1H, m), 2.04 (1H, m), 1.48 (9H, s), 1.01–0.85 (6H, m).

(2S)-2-{3-[(1S)-1-Phenethylcarbonylamino-2-methyl-propyl]-5-phenylmethyl-4,5-dihydro-isoxazole-5-carbonylamino}-succinic Acid 4-t-Butyl Ester-1-methyl Ester (Diastereomeric)

¹H-NMR (500 MHz, CDCl₃) δ 7.56 (d, J=8.3 Hz, 0.5H), 7.47 (d, J=9.3 Hz, 0.5H), 7.28–7.18 (m, 10H), 5.83 & 5.44 (two d, J=8.8 Hz, 1H), 4.70–4.52 (m, 2H), 3.68 & 3.65 (two s, 3H), 3.33–2.28 (m, 10H), 1.89 (m, 1H), 1.43 & 1.42 (two s, 9H), 0.79–0.63 (m, 6H).

(2S)-2-{3-[(1S)-1-(1-Naphthalenecarbonylamino)-2-methyl-propyl]-5-phenylmethyl-4,5-dihydro-isoxazole-5-carbonylamino}-succinic Acid 4-t-Butyl Ester-1-methyl Ester (Diastereomeric)

¹H-NMR (500 MHz, CDCl₃) δ 8.27 (m, 1H), 7.92–7.85 (m, 2H), 7.61–7.15 (m, 10H), 6.45 & 6.05 (two d, NH), 4.99–4.85 (m, 1H), 4.70 (m, 1H), 3.69 & 3.52 (two s, 3H), 3.50–2.32 (m, 6H), 2.12 (m, 1H), 1.40 & 1.39 (two s, 9H), 1.05–0.80 (m, 6H).

(2S)-2-{3-[(1S)-1-(1-naphthalenesulfonylamino-2-methyl-propyl]-5-phenylmethyl-4,5-dihydro-isoxazole-5-carbonylamino}-succinic Acid 4-t-Butyl Ester-1-methyl Ester (Diastereomeric)

¹H-NMR (500 MHz, CDCl₃) δ 8.69–8.62 (m, 1H), 8.33–7.94 (m, 3H), 7.70–7.47 (m, 3H), 7.20–7.05 (m, 5H), 5.32 & 5.15 (two m, 1H), 4.68 & 4.54 (two m, 1H), 3.85 & 3.59 (two m, 1H), 3.82 & 3.62 (two s, 3H), 3.23–1.75 (m, 7H), 1.40 & 1.34 (two s, 9H), 0.85–0.48 (m, 6H).

(2S)-2-{3-[(1S)-1-phenylmethyloxycarbonylamino-2-methyl-propyl]-5-phenylmethyl-4,5-dihydro-isoxazole-5-carbonylamino}-succinic Acid 4-t-Butyl Ester-1-methyl Ester (Diastereomeric)

¹H-NMR (500 MHz, CDCl₃) δ 7.53–7.49 (two d, 1H), 7.35–7.25 (m, 10H), 5.09–5.07 (m, 2.5H), 4.88 (d, 0.5H), 4.69 (m, 1H), 4.34 & 4.23 (two m, 1H), 3.68 & 3.63 (two s, 3H), 3.36–2.23 (m, 6H), 1.89 & 1.70 (two m, 1H), 1.42 & 1.40 (two s, 9H), 0.88–0.73 (m, 6H).

(2S)-2-{3-[(1S)-1-(Indole-3-ethylcarbonylamino)-2-methyl-propyl]-5-phenylmethyl-4,5-dihydro-isoxazole-5-carbonylamino}-succinic Acid 4-t-Butyl Ester-1-methyl Ester (Diastereomeric)

¹H-NMR (500 MHz, CDCl₃) δ 8.54 & 8.38 (two br s, 1H), 7.62–6.97 (m, 1H), 5.83 (d, J=8.8 Hz, 0.5H), 5.20 (d, J=9.3 Hz, 0.5H), 4.73–4.69 (m, 1H), 4.61 & 4.48 (two m, 1H), 3.71 & 3.59 (two s, 3H), 3.28–2.26 (m, 10H), 1.87–1.75 (m, 1H), 1.43 & 1.42 (two s, 9H), 0.78–0.50 (m, 6H).

(2S)-2-{3-[(1S)-1-(Indole-3-yl-methylcarbonylamino)-2-methyl-propyl]-5-phenylmethyl-4,5-dihydro-isoxazole-5-carbonylamino}-succinic Acid 4-t-Butyl Ester-1-methyl Ester (Diastereomeric)

¹H-NMR (500 MHz, CDCl₃) δ 8.37 & 8.26 (two br s, 1H), 7.54–7.12 (m, 11H), 5.95 (d, J=8.8 Hz, 0.5H), 5.76 (d, J=1.5 Hz, 0.5H), 4.68–4.51 (m, 2H), 3.78–3.68 (m, 2H), 3.66 & 3.62 (two s, 3H), 3.28–2.21 (m, 6H), 1.80 (m, 1H), 1.41 & 1.37 (two s, 9H), 0.75–0.46 (m, 6H).

(2S)-2-{3-[(1S)-1-(Cinnamoylamino)-2-methyl-propyl]-5-phenylmethyl-4,5-dihydro-isoxazole-5-carbonylamino}-succinic Acid 4-t-Butyl Ester-1-methyl Ester (Diastereomeric)

¹H-NMR (500 MHz, CDCl₃) δ 7.63–7.25 (m, 12H), 6.43–6.32 (two d, J=15.6 Hz, 1H), 6.09 & 5.68 (two d, J=9.3 Hz, 1H), 4.78–4.70 (m, 1H), 3.69 & 3.68 (two s, 3H), 3.35–2.31 (m, 6H), 2.03 (m, 1H), 1.43 & 1.40 (two s, 9H), 0.92–0.76 (m, 6H).

(2S)-2-{3-[(1S)-1-(Phenylmethylsulfonylamino)-2-methyl-propyl]-5-phenylmethyl-4,5-dihydro-isoxazole-5-carbonylamino}-succinic Acid 4-t-Butyl Ester-1-methyl Ester (Diastereomeric)

¹H-NMR (500 MHz, CDCl₃) δ 7.67 & 7.60 (two d, J=8.8 Hz, 1H), 7.40–7.17 (m, 10H), 3.71 & 3.55 (two s, 3H), 3.37–2.23 (m, 6H), 1.70 (m, 1H), 1.42 & 1.47 (two s, 9H), 0.91–0.65 (m, 6H).

Example 22

Synthesis of (3S)-3-{3-[2-Methyl-(1S)-1-(naphthalene-2-carbonyl-amino)-propyl]-5-phenylmethyl-4,5-dihydro-isoxazole-5-carbonyl-amino}-4-keto-5-(2,6-dichlorobenzoyloxy)-pentanoic Acid-t-butyl Ester A solution of (2S)-2-{3-[(1S)-1-(naphthalene-2-carbonylamino)-2-methyl-propyl]-4,5-dihydro-5-phenylmethyl-isoxazole-5-carbonyl-amino}-succinic acid 4-t-butyl ester (2.86 g, 4.75 mmol) and NMM (0.57 mL, 1.1 eq) in dry THF (xmL) under $N_2$ at 0° C. was treated with isobutyl chloroformate (0.65 mL, 1.05 eq), and stirred for 20 min. To the solution at 0° C. was added diazomethane, and stirred for 30 min. (TLC analysis). Additional diazomethane was needed to complete the reaction (1 h). After completion of the diazoketone formation, 30% HBr/AcOH (4.0 mL, 4.0 eq) was added at 0° C. and the reaction was stirred for 1 h. The reaction was extracted with ethyl acetate (×2) and the organic layer was washed with water, sat'd $NaHCO_3$ and brine, dried (anh $Na_2SO_4$), filtered and concentrated to give 3.36 g of a yellow solid. Half of the solid (~2.375 mmol) was reacted with anhydrous KF (345 mg, 2.5 eq) and 2,6-dichlorobenzoic acid (545 mg, 1.2 eq) in DMF (10 mL) under $N_2$ at room temperature. Usual workup followed by flash chromatography gave the title compound as Diastereomeric mixture (1.53 g). Preparative HPLC (38%EtOAc/Hexane) gave less polar diastereomer (585 mg) and more polar diastereomer (358 mg).

Less polar diastereomer: $^1$H-NMR (500 MHz, CDCl$_3$) δ 8.28 (1H, s), 7.84–7.80 (4H, m), 7.55–7.46 93H, m), 7.29–7.24 98H, m), 6.87 (1H, d, J=88 Hz), 5.05–4.93 (3H, m), 4.73 (1H, m), 3.54 (1H, d, J=18.1 Hz), 3.34 (1H, d, J=13.7 Hz), 3.19 (1H, d, J=14.2 Hz), 3.11 (1H, d, J=17.6 Hz), 2.74–2.70 (1H, m), 2.29–2.24 (2H, m), 1.39 (9H, s), 1.02 (3H, d, J=6.4 Hz), 0.92 (3H, d, J=6.8 Hz). More polar diastereomer: $^1$H-NMR (500 MHz, CDCl$_3$) δ 8.28 (1H, s), 7.97–7.75 (5H, m), 7.62–7.57 (2H, m), 7.37–7.22 (8H, m), 6.56 (1H, d, J=8.3 Hz), 4.94 (1H, m), 4.78 (1H, m), 4.51–4.42 (2H, m), 3.51–3.43 (2H, m), 3.24–3.15 (2H, m), 2.99–2.95 (1H, m), 2.56–2.52 (1H, m), 2.18 (1H, m), 1.45 (9H, s), 1.02 (3H, d, J=6.8 Hz), 0.97 (3H, d, J=6.4 Hz).

The following compoumds were prepared similarly.

(3S)-3-{3-[2-Methyl-(1S)-1-(naphthalene-2-carbonylamino)-propyl]-5-phenoxymethyl-4,5-dihydro-isoxazole-5-carbonyl-amino}-4-keto-5-(2,6-dichlorobenzoyloxy)-pentanoic Acid-t-butyl Ester Less polar diastereomer: $^1$H-NMR (500 MHz, CDCl$_3$) δ 8.29 (1H, s), 7,85–7.81 (5H, m), 7.54–7.46 (2H, m), 7.31–7.23 (5H, m), 6.98–6.87 (4H, m), 5.13–5.03 (3H, m), 4.90 (1H, m), 4.39–427 (2H, ABq, J=9.3 Hz), 3.51 (1H, d, J=17.6 Hz), 3.41 (1H, d, J=17.6 Hz), 2.94–2.78 (2H, m), 2.38 (1H, m), 1.41 99H, s), 1.12–1.08 (6H, two d, J=6.4 Hz). More polar diastereomer: $^1$H-NMR (500 MHz, CDCl$_3$) δ 8.30 (1H, s), 8.11 (1H, d, J=8.8 Hz), 7.93–7.83 (4H, m), 7.59–7.53 (2H, m), 7.33–7.22 (5H, m), 6.97–6.91 (3H, m), 6.77 (1H, d, J=8.8 Hz), 5.37 (1H, d, J=17.1 Hz), 5.16 (1H, d, J=17.1 Hz), 5.01–4.95 (2H, m), 4.53 (1H, d, J=9.8 Hz), 4.25 (1H, d, J=9.8 Hz), 3.50 (1H, d, J=7.6 Hz), 3.32 (1H, d, J=7.6 Hz), 3.04–3.00 (1H, dd, J=17.1, 4.9 Hz), 2.73–7.68 (1H, dd, 17.1, 5.4 Hz), 2.24 (1H, m), 1.47 (9H, s), 1.10–1.03 (6H, two d, J=6.4 Hz).

(3S)-3-{3-[2-Methyl-(1S)-1-(phenylmethyloxycarbonylamino)-propyl]-4,5-dihydro-isoxazole-5-carbonyl-amino}-4-keto-5-(2,6-dichlorobenzoyloxy)-pentanoic Acid-t-butyl Ester (Diastereomeric Mixture)

$^1$H-NMR (500 MHz, CDCl$_3$) δ 7.72–7.60 (1H, m), 7.37–7.30 (8H, m), 5.40 (0.5H, d), 5.23–4.85 (6.5H, m), 4.40 (1H, m), 3.30 (2H, m), 2.92–2.65 (2H, m), 2.10–1.98 (1H, m), 1.44 (9H, s), 1.00–0.87 (6H, m).

Following compounds were similarly prepared:
(3S)-3-{3-[2-Methyl-(1S)-1-(quinoline-2-yl-carbonylamino)-propyl]-5-phenoxymethyl-4,5-dihydro-isoxazole-5-carbonylamino}-4-keto-5-(2,6-dichlorobenzoyloxy)-pentanoic Acid t-Butyl Ester More polar isomer: $^1$H-NMR (500 MHz, CDCl$_3$) δ 8.59 (d, J=8.7 Hz, 1H), 8.31 (d, J=8.3 Hz, 1H), 8.26 (d, J=8.7 Hz, 1H), 8.13 (d, J=8.7 Hz, 1H), 7.98 (d, J=8.7 Hz, 1H), 7.88 9d, J=7.8 Hz, 1H), 7.78 (m, 1H), 7.63 (m, 1H), 722–7.15 (m, 4H), 6.96–6.81 (m, 6H), 4.99–4.81 (m, 4H), 4.40 (d, J=10.1 Hz, 1H), 4.21 (d, J=10.0 Hz, 1H), 3.44 (d, J=17.9 Hz, 1H), 3.24 (d, J=17.9 Hz, 1H), 3.03 (dd, J=17.0, 4.6 Hz, 1H), 2.76 (dd, J=17.0, 5.5 Hz, 1H), 2.30 (m, 1H), 1.45 (s, 9H), 1.10 (m, 6H); Less polar isomer: $^1$H-NMR (500 MHz, CDCl$_3$) δ 8.68 (d, J=8.7 Hz, 1H), 8.32–8.26 (m, 2H), 8.17 (d, J=8.7 Hz, 1H), 7.91 (m, 2H), 7.80 (m, 1H), 7.66 (m, 1H), 7.28 (m, 4H), 7.02–6.87 (m, 6H), 5.01–4.77 (m, 4H), 4.38–4.30 (m, 2H), 3.50–3.38 (ABq, J=17.9 Hz, 2H), 3.06–3.02 (m, 1H), 2.84–2.80 (m, 1H), 2.34 (m, 1H), 1.44 (s, 9H), 1.14 (m, 6H).

(3S)-3-{3-[2-Methyl-(1S)-1-(quinoline-2-yl-carbonylamino)-propyl]-5-phenoxymethy-4,5-dihydro-isoxazole-5-carbonylamino}-4-keto-5-(2,6-dichlorobenzoyloxy)-pentanoic Acid.

From more polar isomer: $^1$H-NMR (500 MHz, DMSO-d$_6$) δ 9.01 (d, J=9.2 Hz, 1H), 8.87 (d, J=8.3 Hz, 1H), 8.55 (d, J=8.3 Hz, 1H), 8.18–8.07 (m, 3H), 7.87 (m, 1H), 7.73 (m, 1H), 7.28–7.14 (m, 4H), 6.96–6.75 (m, 6H), 5.00–4.75 (m, 4H), 4.42 (d, J=10.6 Hz, 1H), 4.22 (d, J=10.6 Hz, 1H), 3.47–3.35 (ABq, J=17.9 Hz, 2H), 2.82 (dd, J=17.0, 6.4 Hz, 2.56 (m, 1H), 2.33 (m, 1H), 0.98 (m, 6H). From less polar isomer: $^1$H-NMR (500 MHz, DMSO-d$_6$) δ 9.06 (d, J=9.2 Hz, 1H), 8.88 (d, J=7.8 Hz, 1H), 8.57 (d, J=8.7 Hz, 1H), 8.22–8.07 (m, 3H), 7.87 (m, 1H), 7.73 (m, 1H), 7.17 (m, 4H), 6.91–6.78 (m, 6H), 4.98–4.90 (ABq, J=17.9 Hz, 2H), 4.77 (m, 2H), 4.35 (d, J=10.6 Hz, 1H), 4.20 (d, J=10.6 Hz, 1H), 3.47–3.35 (ABq, J=18.3 Hz, 2H), 2.89 (dd, J=17.0, 6.4 Hz, 2.61 (dd, J=17.0, 6.4, 1H), 2.31 (m, 1H), 0.98 (d, J=6.9 Hz, 3H), 0.90 (d, J=6.9 Hz, 3H).

(3S)-3-{3-[2-Methyl-(1S)-1-(1-naphthalenecarbonylamino)-propyl]-5-phenylmethyl-4,5-dihydro-isoxazole-5-carbonylamino}-4-keto-5-(2,6-dichlorobenzoyloxy)-pentanoic Acid t-Butyl Ester More polar isomer: $^1$H-NMR (500 MHz, CDCl$_3$) δ 8.29 (d, J=8.3 Hz), 7.94 (d, J=8.3 Hz), 7.88 (d, J=7.4 Hz, 1H), 7.74 (d, J=9.7 Hz, 1H), 7.61–7.44 (m, 4H), 7.35–7.18 (m, 8H), 6.23 (d, J=8.7 Hz, 1H), 4.95 (m, 1H), 4.76 (m, 1H), 4.49–4.41 (ABq, J=17.5 Hz, 2H), 3.49–3.41 (m, 2H), 3.22–3.12 (m, 2H), 2.92 (dd, J=17.0, 4.2 Hz, 1H), 2.52 (dd, J=17.0, 5.1 Hz, 1H), 2.13 (m, 1H), 1.37 (s, 9H), 1.04 (d, J=6.9 Hz, 3H), 0.91 (d, J=6.9 Hz, 3H). Less polar isomer: $^1$H-NMR (500 MHz, CDCl$_3$) δ 8.24 (d, J=8.3 Hz, 1H), 7.83 (m, 2H), 7.57–7.47 (m, 4H), 7.38–7.22 (m, 9H), 6.64 (d, J=9.2 Hz, 1H), 5.00–4.87 (m, 3H), 4.72 (m, 1H), 3.60 (d, J=17.9 Hz, 1H), 3.36 (d, J=14.2 Hz, 1H), 3.20 (d, J=14.2 Hz, 1H), 3.12 (d, J=17.9 Hz, 1H), 2.69 (dd, J=17.0, 4.6 Hz, 1H), 228–2.18 (m, 2H), 1.38 (s, 9H), 1.06 (d, J=6.4 Hz, 3H), 0.88 (d, J=6.9 Hz, 3H).

(3S)-3-{3-[2-Methyl-(1S)-1-(Cinnamoylamino)-propyl]-5-phenylmethyl-4,5-hydro-isoxazole-5-carbonylamino}-4-keto-5-(2,6-dichlorobenzoyloxy)-pentanoic Acid t-Butyl Ester (More Polar Isomer)

$^1$H-NMR (500 MHz, CDCl$_3$) δ 7.72 (d, 1H), 7.62 (d, J=15.6 Hz, 1H), 7.50 (m, 1H), 7.38–7.21 (m, 12H), 6.39 (d,

J=15.6 Hz, 1H), 5.90 (d, J=9.2 Hz, 1H), 4.76 (m, 2H), 4.49–4.41 (ABq, J=17.4 Hz, 2H), 3.42–3.38 (m, 2H), 3.17 (d, J=14.2 Hz, 1H), 3.09 (d, J=17.9 Hz, 1H), 2.91 (dd, J=17.4, 4.6 Hz, 1H), 2.52 (dd, J=17.4, 5.0 Hz, 1H), 2.04 (m, 1H), 1.41 (s, 9H), 0.90 (m, 6H). Less polar isomer: $^1$H-NMR (500 MHz, CDCl$_3$) δ 7.61 (d, 1H), 7.52 (d, 1H), 7.41 (d, 1H), 7.28 (m, 2H), 6.64–6.41 (m, 2H), 5.09–4.99 (ABq, J=17.4 Hz, 2H), 4.81 (m, 1H), 4.69 (m, 1H), 3.50 (d, J=17.9 Hz, 1H), 3.34 (d, J=14.2 Hz, 1H), 3.17 (d, J=14.2 Hz, 1H), 3.04 (d, J=17.9 Hz, 1H), 2.74 (dd, J=17.0, 4.2 Hz, 1H), 2.22 (m, 2H), 1.39 (s, 9H), 0.97–0.88 (m, 6H).

(3S)-3-{3-[2-Methyl-(1S)-1-(phenylmethylsulfonylamino)-propyl]-5-phenylmethyl-4,5-dihydro-isoxazole-5-carbonylamino}-4-keto-5-(2,6-dichlorobenzoyloxy)-pentanoic Acid t-Butyl Ester More polar isomer: $^1$H-NMR (500 MHz, CDCl$_3$) δ 7.77 (d, J=9.3 Hz, 1H), 7.38–7.23 (m, 13H), 4.80–4.63 (m, 2H), 4.56–4.46 (ABq, J=17.1 Hz, 2H), 4.21–4.10 (m, 2H), 3.83 (m, 2H), 3.41–3.37 (m, 1H), 3.19 (d, J=14.2 Hz, 1H), 2.90–2.83 (m, 2H), 2.53 (m, 1H), 1.76 (m, 1H), 1.41 (s, 9H), 0.83 (d, J=6.8 Hz, 3H), 0.77 (d, J=6.8 Hz, 3H). Less polar isomer: $^1$H-NMR (500 MHz, CDCl$_3$) δ 7.64 (d, J=9.2 Hz, 1H), 7.36–7.26 (m, 13H), 5.05–4.95 (m, 3H), 4.74 (m, 1H), 4.17 (m, 2H), 3.96 (m, 1H), 3.41–2.99 (m, 4H), 2.70 (m, 1H), 2.19 (m, 1H), 1.79 (m, 1H), 1.39 (s, 9H), 0.86 (d, J=6.4 Hz, 3H), 0.77 (d, J=6.8 Hz, 3H).

(3S)-3-{3-[2-Methyl-(1S)-1-(quinoline-2-yl-carbonylamino)-propyl]-4,5-dihydro-isoxazole-5-carbonylamino}-4-keto-5-(2,6-dichlorobenzoyloxy)-pentanoic Acid t-Butyl Ester More polar isomer: $^1$H-NMR (500 MHz, CDCl$_3$) δ 8.59 (d, J=8.7 hz, 1H), 8.31 (d, J=8.7 Hz, 1H), 8.26 (d, J=8.7 Hz, 1H), 8.12 (d, J=8.3 Hz, 1H), 7.88 (d, J=8.3 Hz, 1H), 7.78–7.72 (m, 2H), 7.62 (m, 1H), 7.33–7.27 (m, 3H), 5.20–5.05 (m, 3H), 4.92–4.89 (m, 2H), 3.47–3.34 (m, 2H), 2.95 (dd, J=17.0, 4.6 Hz, 1H), 2.73 (dd, J=17.0, 5.1 Hz, 1H), 2.28 (m, 1H), 1.45 (s, 9H), 1.07 (m, 6H). Less polar isomer: $^1$H-NMR (500 MHz, CDCl$_3$) δ 8.58 (d, J=9.2 Hz, 1H), 8.28–8.24 (m, 2H), 8.12 (d, J=8.7 Hz, 1H), 7.85 (d, J=7.8 Hz, 1H), 7.75–7.59 (m, 3H), 7.31–7.25 (m, 3H), 5.12–4.89 (m, 5H), 3.46–3.41 (m, 2H), 2.92 (dd, J=17.0, 5.1 Hz, 1H), 2.78 (dd, J=17.0, 5.5 Hz, 1H), 2.30 (m, 1H), 1.44 (s, 9H), 1.10 (m, 6H).

(3S)-3-{3-[2-Methyl-(1S)-1-(quinoline-2-yl-carbonylamino)-propyl]-5-phenylmethyl-4,5-dihydro-isoxazole-5-carbonylamino}-4-keto-5-(2,6-dichlorobenzoyloxy)-pentanoic Acid t-Butyl Ester More polar isomer: $^1$H-NMR (500 MHz, CDCl$_3$) δ 8.52 (d, J=9.2 Hz, 1H), 8.32 9d, J=8.3 Hz, 1H), 8.26 (d, J=8.3 Hz, 1H), 8.12 (d, J=8.7 Hz, 1H), 7.88 (d, J=8.3 Hz, 1H), 7.80–7.63 (m, 3H), 7.36–7.18 (m, 8H), 4.82 (m, 1H), 4.72 (m, 1H), 4.47–4.37 (ABq, J=17.0 Hz, 2H), 3.47 (d, J=17.9 Hz, 1H), 3.41 (d, J=13.8 Hz, 1H), 3.19 (d, J=14.2 Hz, 1H), 3.14 (d, J=17.9 Hz, 1H), 2.94 (dd, J=17.4, 4.1 Hz, 1H), 2.53 (dd, J=17.0, 5.0 Hz, 1H), 2.18 (m, 1H), 1.45 (s, 9H), 0.98 (m, 6H). Less polar isomer: $^1$H-NMR (500 MHz, CDCl$_3$) δ 8.52 (d, J=9.2 Hz, 1H), 8.28–8.23 (m, 2H), 8.12 (d, J=8.7 Hz, 1H), 7.85 (d, J=8.3 Hz, 1H), 7.73 (m, 1H), 7.62–7.55 (m, 2H), 7.31–7.17 (m, 8H), 5.06–4.98 (ABq, J=17.0 Hz, 2H), 4.84 (m, 1H), 4.69 (m, 1H), 5.54 (d, J=17.9 Hz, 1H), 3.29 (d, J=14.2 Hz, 1H), 3.16 (d, J=14.2 Hz, 1H), 3.10 (d, J=17.9 Hz, 1H), 2.70 (dd, J=17.4, 4.1 Hz, 1H), 2.21 (m, 1H), 2.11 (dd, J=17.0, 5.1 Hz, 1H), 1.38 (s, 9H), 0.98 (m, 6H).

(3S)-3-{3-[2-Methyl-(1S)-1-(quinoline-2-yl-carbonylamino)-propyl]-5-phenylmethyl-4,5-dihydro-isoxazole-5-carbonylamino}-4-keto-5-phenoxy-pentanoic Acid t-Butyl Ester More polar isomer: $^1$H-NMR (500 MHz, CDCl$_3$) δ 8.47 (d, J=9.2 Hz, 1H), 8.32 (d, J=8.7 Hz, 1H), 8.25 (d, J=8.3 Hz, 1H), 8.13 (d, J=8.7 Hz, 1H), 7.89 (d, J=7.8 Hz, 1H), 7.78 (m, 1H), 7.69 (d, J=8.8 Hz, 1H), 7.64 (t, J=7.3 Hz, 1H), 7.29–7.17 (m, 4H), 7.06 (t, J=7.4 Hz, 1H), 6.96 (t, J=7.4 Hz, 1H), 6.78 (d, J=8.3 Hz, 2H), 4.81–4.72 (m, 2H), 4.47–4.28 (ABq, J=17.9 Hz, 2H), 3.42 (d, J=17.9 Hz, 1H), 3.34 (d, J=14.2 Hz, 1H), 3.15 (d, J=13.7 Hz, 1H), 3.10 (d, J=17.9 Hz, 1H), 2.94 (dd, J=17.4, 4.1 Hz, 1H), 2.64 (dd, J=17.4, 5.5 Hz, 1H), 2.15 (m, 1H), 1.43 (s, 9H), 0.95 (m, 6H). Less polar isomer: $^1$H-NMR (500 MHz, CDCl$_3$) δ 8.50 (d, J=9.2 Hz, 1H), 8.24 (d, J=8.3 Hz, 1H), 8.18 (d, J=8.3 Hz, 1H), 8.10 (d, J=8.2 Hz, 1H), 7.85 (d, J=7.7 Hz, 1H), 7.74 (m, 1H), 7.62–7.56 (m, 2H), 7.29–7.16 (m, 5H), 6.88 (t J=7.4 Hz, 1H), 6.78 (d, J=7.8 Hz, 2H), 4.81–4.66 (m, 4H), 3.46 (d, J=17.9 Hz, 1H), 3.29 (d, J=13.8 Hz, 1H), 3.15 (d, J=13.8 Hz, 1H), 3.07 (d, J=17.9 Hz, 1H), 2.76 (dd, J=17.0, 4.1 Hz, 1H), 2.21–2.09 (m, 2H), 1.37 (s, 9H), 0.93 (m, 6H).

(3S)-3-{3-[2-Methyl-(1S)-1-(2-naphthalenecarbonylamino)-propyl]-4,5-dihydro-isoxazole-5-carbonylamino}-4-keto-pentanoic Acid t-Butyl Ester Diastereomeric mixture: $^1$H-NMR (500 MHz, CDCl$_3$) δ 8.29 (m, 1H), 7.96–7.50 (m, 7H), 6.85–6.73 (m, 1H), 5.10–4.97 (m, 2H), 4.66 (m, 1H), 3.40 (m, 2H), 2.94–2.60 (m, 2H), 2.32–2.14 (m, 1H), 2.22 & 2.10 (two s, 3H), 1.43 & 1.42 (two s, 9H), 1.10–0.95 (m, 6H).

Example 23

Synthesis of (3S)-3-{3-[2-Methyl-(1S)-1-(naphthalene-2-carbonyl-amino)-propyl]-phenoxymethyl-4,5-dihydro-isoxazole-5-carbonyl-amino}-4-keto-5-phenoxy-pentanoic Acid t-Butyl Ester The title compound was prepared with conventional EDC coupling of 3-[2-methyl-(1S)-1-(naphthalene-2-carbonyl-amino)-propyl]-5-phenoxymethyl-4,5-dihydro-isoxazole-5-carboxylic acid (1.00 g, 2.24 mmol) and (3S)-3-amino-4-hydroxy-5-phenoxy-pentanoic acid t-butyl ester (630 mg, 1.0 eq), EDC (558 mg, 1.3 eq), HOBt (394 mg, 1.3 eq) and triethylamine (0.94 mL, 3.0 eq) in DMF (5 mL). Usual workup followed by flash chromatography gave 1.44 g of coupled product. The coupled product and Dess-Martin reagent (2.15 g, 2.5 mol eq) in dry CH$_2$Cl$_2$ (25 mL) under N$_2$ at room temperature was stirred for 1 h, then quenched with isopropyl alcohol (3 mL). Usual extractive workup followed by flash chromatography (36% ethyl acetate-hexane) gave 1.27 g of the tide compound as diastereomeric mixture. Preparative HPLC (36% ethyl acetate-hexanes, 10 mL/min, 278 nm UV detection) afforded less polar (352 mg) and more polar (536 mg) diastereomers.

Less polar diastereomer: $^1$H-NMR (500 MHz, CDCl$_3$) δ 8.29 (1H, s), 7.93–7.81 (5H, m), 7.58–7.51 (2H, m), 7.28–7.21 94H, m), 6.99–6.76 (7H, m), 5.00–4.98 (2H, m), 4.79–4.66 (2H, ABq, J=16.6 Hz), 4.35–4.29 (2H, ABq, J=10.3 Hz), 3.40 (2H, s), 3.02–2.98 (1H, dd, J=16.6, 4.9 Hz), 2.84–2.79 (1H, dd, J=16.6, 4.7 Hz), 2.30 (1H, m), 1.41 (9H, s), 1.12–1.07 (6H, two d, J=6.8 Hz). More polar diastereomer: $^1$H-NMR (500 MHz, CDCl$_3$) δ 8.29 (1H, s), 7.99–7.82 (5H, m), 7.59–7.53 (2H, m), 7.26–7.18 (4H, m), 6.97–6.83 (6H, m), 6.68 (1H, d, J=8.3 Hz), 5.01–4.95 (3H, m), 4.83 (1H, d, J=17.1 Hz), 4.42 (1H, d, J=9.8 Hz), 4.23 (1H, d, J=9.8 Hz), 3.49–3.32 (2H, ABq, J=18.1 Hz), 3.06–3.02 (1H, dd, J=17.1, 4.4 Hz), 2.76–2.72 (1H, dd, J=17.1, 5.4 Hz), 2.24 (1H, m), 1.45 (9H, s), 1.10–1.02 (6H, two d, J=6.8 Hz).

The following compoumds were prepared similarly:

(3S)-3-{3-[2-Methyl-(1S)-1-(naphthalene-2-carbonylamino)-propyl]-5-phenoxymethyl-4,5-dihydro-isoxazole-5-carbonyl-amino}-4-keto-5-(2-naphthyloxy)-pentanoic Acid-t-butyl Ester Less polar diastereomer: $^1$H-NMR (500 MHz, CDCl$_3$) δ 8.27 (1H, s), 7.89 (8H, m), 7.56–7.26 (6H, m), 7.23–6.87 (5H, m), 6.74 (1H, d, J=9.3 Hz), 5.04–4.95 (2H, m), 4.92–4.80 (2H, ABq, J=16.6 Hz), 4.37–4.30 (2H, ABq, J=23.4, 10.3 Hz), 3.43–3.38 (2H, ABq, J=22.5, 17.8 Hz), 3.05–3.00 (1H, dd, J=16.6, 4.9 Hz), 2.86–2.82 (1H, dd, J=16.6, 4.9 Hz), 2.25 (1H, m), 1.42 (9H, s), 1.09–1.05 (6H, two d, J=6.8, 6.7 Hz). More polar diastereomer: $^1$H-NMR (500 MHz, CDCl$_3$) δ 8.30 (1H, s), 8.02–7.55 (10H, m), 7.41–7.05 (6H, m), 6.89–6.66 (4H, m), 5.10–4.94 (4H, m), 4.41 (1H, d, J=9.8 Hz), 4.23 91H, d, J=10.3 Hz), 3.50–3.34 (2H, ABq, J=17.6 Hz), 3.09–3.05 (1H, dd, J=17.1, 4.4 Hz), 2.79–2.74 (1H, dd, J=17.1, 5.4 Hz), 2.25 (1H, m), 1.45 (9H, s), 1.10–1.02 (6H, two d, J=6.8 Hz).

(3S)-3-{3-[2-Methyl-(1S)-1-quinoline-2-yl-carbonylamino)-propyl]-4,5-dihydro-isoxazole-5-carbonylamino}-4-keto-5-phenoxy-pentanoic Acid t-Butyl Ester More polar isomer: $^1$H-NM (500 MHz, CDCl$_3$), δ 8.60 (d, J=9.2 Hz, 1H), 8.32–8.25 (m, 2H), 8.13 (d, J=8.8 Hz, 1H), 7.88 (d, J=7.8 Hz, 1H), 7.79–7.62 (m, 3H), 7.27 (m, 2H), 6.97 (m, 1H), 6.88 (m, 2H), 5.04–4.72 (m, 5H), 3.48–3.34 (m, 2H), 3.00 (dd, J=17.0, 4.6 Hz, 1H), 2.77 (dd, J=17.0, 5.5 Hz, 1H), 2.27 (m, 1H), 1.45 (s, 9H), 1.06 (m, 6H). Less polar isomer: $^1$H-NMR (500 MHz, CDCl$_3$) δ 8.58 (d, J=9.2 Hz, 1H), 8.27 (d, J=8.2 Hz, 1H), 8.21 (d, J=8.3 Hz, 1H), 8.13 (d, J=8.3 Hz, 1H), 7.86 (d, J=8.3 Hz, 1H), 7.78–7.59 (m, 3H), 7.22 (m, 2H), 6.92 (m, 1H), 6.82 (m, 2H), 5.04–4.88 (m, 3H), 4.82–4.69 (ABq, J=17.0 Hz, 2H), 3.45–3.33 (m, 2H), 2.99 (dd, J=16.5, 4.6 Hz, 1H), 2.78 (dd, J=16.5, 5.1 Hz, 1H), 2.26 (m, 1H), 1.42 (s, 9H), 1.06 (m, 6H).

t-Butyl (3S)-3-{3-[2-Methyl-(1S)-1-(3-t-butyloxycarbonylpropanoylamino)-propyl]-5-n-pentyl-4,5-dihydro-isoxazole-5-carbonylamino}-4-keto-5-(2,6-dichlorobenzoyloxy)-pentanoate; Less Polar Isomer (Compound 89LP Precursor)

$^1$H-NMR (500 MHz, CDCl$_3$) δ 7.67 ((d, J=8.7 Hz, 1H), 7.32 (m, 3H), 6.42 (m, 1H), 5.20–5.05 (ABq, J=17.0 Hz, 2H), 4.90 (m, 1H), 4.67 (m, 1H), 3.38 (d, J=17.9 Hz, 1H), 2.92 (m, 2H), 2.78 (m, 3H), 2.53 (m, 2H), 2.40 (m, 2H), 2.18 (m, 2H), 2.03 (m, 1H), 1.79 (m, 1H), 1.44 (s, 9H), 1.41 (s, 9H), 1.26 (m, 6H), 0.94 (m, 6H), 0.86 (t, J=6.9 Hz, 3H).

t-Butyl (3S)-3-{3-[2-Methyl-(1S)-1-(3-t-butyloxycarbonylpropanoylamino)-propyl]-5-n-pentyl-4,5-dihydro-isoxazole-5-carbonylamino}-4-keto-5-(2,6-dichlorobenzoyloxy)-pentanoate; More Polar Isomer (Compound 90MP Precursor)

$^1$H-NMR (500 MHz, CDCl$_3$) δ 7.76 (d, J=8.7 Hz, 1H), 7.31 (m, 3H), 6.17 (d, J=8.7 Hz, 1H), 5.17–5.07 (ABq, J=17.0 Hz, 2H), 4.87 (m, 1H) 4.65 (m, 1H), 3.30 (d, J=17.9 Hz, 1H), 2.96–2.90 (m, 2H), 2.69 (m, 1H), 2.56 (m, 2H), 2.45 (m, 2H), 2.03 (m, 2H), 1.81 (m, 1H), 1.43 (s, 9H), 1.41 (s, 9H), 1.26 (m, 6H), 0.94–0.86 (m, 9H).

t-Butyl (3S)-3-{3-[2-Methyl-(1S)-1-(3-t-butyloxycarbonylpropanoylamino)-propyl]-5-phenylmethyl-4,5-dihydro-isoxazole-5-carbonylamino}-4-keto-5-(2,6-dichlorobenzoyloxy)-pentanoate; Less Polar Isomer (Compound 85LP Precursor)

$^1$H-NMR (500 MHz, CDCl$_3$) δ 7.51 (d, J=9.2 Hz, 1H), 7.34–7.22 (m, 8H), 6.37 (d, J=9.2 Hz, 1H), 5.10–4.98 (ABq, J=17.4 Hz, 2H), 4.70 (m, 1H) 4.61 (m, 1H), 3.46 (d, J=17.9 Hz, 1H), 3.31 (d, J=14.2 Hz, 1H), 3.14 (d, J=14.2 Hz, 1H), 2.99 (d, J=17.9 Hz, 1H), 2.73 (m, 1H), 2.53 (m, 2H), 2.40 (m, 2H), 2.18 (m, 1H), 2.09 (m, 1H), 1.42 (s, 9H), 1.39 (s, 9H), 0.90 (d, J=6.9 Hz, 3H), 0.84 (d, J=6.4 Hz, 3H).

t-Butyl (3S)-3-{3-[2-Methyl-(1S)-1-(3-t-butyloxycarbonylpropanoylamino)-propyl]-5-ethyl-4,5-dihydro-isoxazole-5-carbonylamino}-4-keto-5-(2,6-dichlorobenzoyloxy)-pentanoate; Less Polar Isomer (Compound 91LP Precursor)

$^1$H-NMR (500 MHz, CDCl$_3$) δ 7.68 (d, J=8.7 Hz, 1H), 7.32 (m, 3H), 6.42 (d, J=9.2, 1H), 5.21–5.05 (ABq, J=17.0 Hz, 2H), 4.91 (m, 1H) 4.67 (m, 1H), 3.37 (d, J=17.9 Hz, 1H), 2.94 (m, 2H), 2.79 (m, 1H), 2.53 (m, 2H), 2.40 (m, 2H), 2.18 (m, 1H), 2.07 (m, 1H), 1.86 (m, 1H), 1.43 (s, 9H), 1.41 (s, 9H), 0.94 (m, 9H).

t-Butyl (3S)-3-{3-[2-Methyl-(1S)-1-(3-t-butyloxycarbonylpropanoylamino)-propyl]-5-methyl-4,5-dihydro-isoxazole-5-carbonylamino}-4-keto-5-(2,6-dichlorobenzoyloxy)-pentanoate; Less Polar Isomer (Compound 73LP Precursor)

$^1$H-NMR (500 MHz, CDCl$_3$) δ 7.66 (d, J=8.7 Hz, 1H), 7.32 (m, 3H), 6.44 (d, J=9.2, 1H), 5.20–5.04 (ABq, J=17.0 Hz, 2H), 4.88 (m, 1H) 4.67 (m, 1H), 3.46 (d, J=17.9 Hz, 1H), 2.94–2.76 (m, 3H), 2.53 (m, 2H), 2.40 (m, 2H), 2.19 (m, 1H), 1,62 (s, 3H), 1.43 (s, 9H), 1.41 (s, 9H), 0.95 (m, 6H).

t-Butyl (3S)-3-{3-[2-Methyl-(1S)-1-(3-t-butyloxycarbonylpropanoylamino)-propyl]-5-methyl-4,5-dihydro-isoxazole-5-carbonylamino}-4-keto-5-(2,6-dichlorobenzoyloxy)-pentanoate; More Polar Isomer (Compound 74MP Precursor)

$^1$H-NMR (500 MHz, CDCl$_3$) δ 7.74 (d, J=8.7 Hz, 1H), 7.33 (m, 3H), 6.18 (d, J=8.7 Hz, 1H), 5.18–5.05 (ABq, J=16.5 Hz, 2H), 4.87 (m, 1H) 4.65 (m, 1H), 3.38 (d, J=17.9 Hz, 1H), 2.93–2.89 (m, 2H), 2.71 (m, 1H), 2.57 (m, 2H), 2.46 (m, 2H), 2.02 (m, 1H), 1.66 (s, 3H), 1.58 (s, 9H), 1.46 (s, 9H), 0.95–0.86 (m, 6H).

t-Butyl (3S)-3-{3-[2-Methyl-(1S)-1-(3-t-butyloxycarbonylpropanoylamino)-propyl]-5-phenylmethyl-4,5-dihydro-isoxazole-5-carbonylamino}-4-keto-5-(2,6-dichlorobenzoyloxy)-pentanoate; More Polar Isomer (Compound 86MP Precursor)

$^1$H-NMR (500 MHz, CDCl$_3$) δ 7.68 (d, J=9.2 Hz, 1H), 7.30 (m, 8H), 6.07 (d, J=8.7 Hz, 1H), 4.72 (m, 1H), 4.60 (m, 1H), 4.45–4.36 (ABq, J=17.0 Hz, 2H), 3.40–3.32 (m, 2H), 3.17 (d, J=14.2 Hz, 1H), 3.06 (d, J=17.9 Hz, 1H), 2.93 (m, 1H), 2.60–2.38 (m, 5H), 1.98 (m, 1H), 1.44 (s, 9H), 1.41 (s, 9H), 0.88–0.82 (m, 6H).

Example 24

Synthesis of (3S)-3-{3-[(1S)-1-benzyloxycarbonylamino-2-methyl-propyl]-5-phenoxymethyl-4,5-dihydro-isoxazole-5-carbonyl-amino}-4-keto-pentanoic Acid A solution of (3S)-3-{3-[(1S)-1-phenylmethyloxycarbonylamino-2-methyl-propyl]-5-phenoxymethyl-4,5-dihydro-isoxazole-5-carbonyl}-4-keto-pentanoic acid t-butyl ester (less polar diastereomer) (44 mg) in CH$_2$Cl$_2$ (2 mL) at 0° C. was treated with TFA (1 mL). The reaction mixture was stirred for 2 h while slowly warming to room temperature. Concentration gave the title compound (compound 10, quantitative).

$^1$H NMR (500 MHz, CD$_3$OD) δ 7.35–6.90 (10H, m), 5.11 (2H, s), 4.53 (1H, m), 4.47 (1H, m), 4.23 (2H, dd), 2.86 (1H, dd), 2.54 (1H, dd), 2.24 (3H, s), 2.00 (1H, m), 1.00 and 0.97 (6H, two d); MS [M+Na]$^+$ 562.

The following compound was prepared similarly from the less polar isomer.

(3S)-3-{3-[(1S)-1-phenylmethyloxycarbonylamino-2-methyl-propyl]-5-phenoxymethyl-4,5-dihydro-isoxazole-5-carbonyl-amino}-4-keto-pentanoic Acid (Compound 11).

$^1$H NMR (500 MHz) δ 8.76 (1H, d, J=7.8 Hz), 7.76 (1H, d, J=8.8 Hz), 7.36–6.87 (10H, m), 5.06 (2H, m), 4.50 (1H, m), 4.32 (1H, m), 4.16 (2H, m), 3.21 (2H, app s), 2.79 (1H, m), 2.06 (3H, s), 1.89 (1H, m), 0.91 (3H, d, J=6.3 Hz), 0.80 (3H, d, J=6.3 Hz).

The following final compounds were obtained by a similar TFA deprotection of the corresponding t-butyl ester.

(3S)-3-{3-[(1S)-1-Phenylmethyloxycarbonylamino-2-methyl-propyl]-4,5-dihydro-isoxazole-5-carbonylamino}-4-keto-pentanoic Acid (Compound 3, Diastereomeric Mixture)

$^1$H NMR (500 MHz, DMSO-d$_6$) δ 8.49 (1H, m), 7.72 (1H, m), 7.35 (5H, m), 5.03 (3H, m), 4.40 (1H, m), 4.15 (1H, m), 3.24 (2H, m), 2.54 (2H, m), 2.04 and 1.95 (3H, wo s), 1.88 (1H, m), 0.90–0.91 (6H, m): MS [M+Na]$^+$ 456.

(3S)-3-{3-[(1S)-1-Phenylmethyloxycarbonylamino-2-methyl-propyl]-4,5-dihydro-isoxazole-5-carbonylamino}-4-keto-5-(2,6-dichlorobenzoyloxy)-pentanoic Acid (Compound 14, Diastereomeric Mixture)

$^1$H NMR (500 MHz, DMSO-d$_6$) δ 8.58 (1H, br s), 7.75 (1H, m), 7.61–7.30 (8H, m), 5.30–5.00 (5H, m), 4.70 (1H, m), 4.16 (1H, m), 2.66 (2H, m), 1.90 (1H, m), 0.95–0.79 (6H, m): MS [M+Na]$^+$ 644.

(3S)-3-{3-[(1S)-1-(Naphthalene-1-carbonylamino)-2-methyl-propyl]5-phenoxymethyl-4,5-dihydro-isoxazole-5-carbonylamino}-4-keto-5-phenoxy-pentanoic Acid (Compound 17, Diastereomeric Mixture)

$^1$H NMR (500 MHz, DMSO-d$_6$) δ 8.92–8.55 (2H, m), 8.15–7.98 (3H, m), 7.63–7.55 (4H, m), 7.25–7.15 (4H, m), 6.95–6.74 (6H, m), 5.20–4.15 (6H, m), 2.80–2.55 (2H, m), 2.05 (1H, m), 1.05–0.89 (6H, m): MS [M+Na]$^+$ 674.

(3S)-3-{3-[(1S)-1-(Naphthalene-2-carbonylamino)-2-methyl-propyl]-5-phenoxymethy-4,5-dihydro-isoxazole-5-carbonylamino}-4-keto-5-phenoxy-pentanoic Acid (Compound 18)

From less polar t-butyl ester: $^1$H NMR (500 MHz, DMSO-d$_6$) δ 8.93 (1H, d, J=7.8 Hz), 8.79 (1H, d, J=8.3 Hz), 8.48 (1H, s), 8.05–7.94 (4H, m), 7.64–7.58 (2H, m), 7.30–7.17 (4H, m), 6.94–6.83 (6H, m), 4.96 (2H, app s), 4.78 (1H, m), 4.73 (1H, m), 4.36 (1H, d, J=10.2 Hz), 4.22 (1H, d, J=10.2 Hz), 3.37 (2H, app s), 2.91 (1H, dd, J=16.6, 6.4 Hz), 2.62 (1H, dd, J=16.6, 5.9 Hz), 2.12 (1H, m), 1.00 (3H, d, J=6.3 Hz), 0.87 93H, d, J=6.3 Hz): MS [M+Na]$^+$ 674; From more polar t-butyl ester: $^1$H NMR (500 MHz, DMSO-d$_6$) δ 8.88 (1H, d, J=8.3 Hz), 8.79 (1H, d, J=8.8 Hz), 8.43 (1H, s), 8.00–7.80 (4H, m), 7.61 (2H, m), 7.23–7.17 94H, m), 6.93–6.77 (6H, m), 4.99 (1H, d, J=17.6 Hz), 4.86 (1H, d, J=18.1 Hz), 4.79 (1H, m), 4.72 (1H, m0, 4.43 (1H, d, J=10.7 Hz), 4.20 (1H, d, J=10.2 Hz), 2.81 (1H, dd), 2.56 (1H, dd), 2.17 (1H, m), 1.01 (3H, d, J=6.3 Hz), 0.99 (3H, d, J=6.3 Hz): MS [M+Na]$^+$ 674.

(3S)-3-{3-[(1S)-1-(Naphthalene-1-carbonylamino)-2-methyl-propyl]-5-phenoxymethyl-4,5-dihydro-isoxazole-5-carbonylamino}-4-keto-5-(2,6-dichlorobenzoyloxy)-pentanoic Acid (Compound 27)

From less polar t-butyl ester: $^1$H NMR (500 MHz, DMSO-d$_6$) δ 9.08 (1H, d, J=7.8 Hz), 8.87 (1H, d, J=8.8 Hz), 8.55 (1H, s), 8.10–8.01 (4H, m), 7.68–7.58 (5H, m), 7.26 (2H, t, J=7.8 Hz), 6.98–6.92 (3H, m), 5.27 (2H, ABq, J=16.6 Hz0, 4.82–4.78 (2H, m), 4.43 (1H, d, J=10.7 Hz), 4.29 (1H, d, J=10.3 Hz), 3.44 (2H, ABq, J=18.1 Hz), 3.01 (1H, dd, J=17.1, 6.4 Hz), 2.67 (1H, dd, J=17.1, 6.3 Hz), 2.21 (1H, m), 1.07 (3H, d, J=6.2 Hz), 0.97 (3H, d, J=6.2 Hz): MS [M+Na]$^+$ 770; From more polar t-butyl ester: $^1$H NMR (500 MHz, DMSO-d$_6$) δ 8.97 (1H, d, J=7.8 Hz), 8.85 (1H, d, J=8.3 hz), 8.50 (1H, s), 8.09–7.96 (4H, m), 7.67–7.60 (5H, m), 7.32 (2H, t, J=6.3 Hz), 7.00 (3H, m), 5.38 (1H, d, J=17.1 Hz), 5.13 (1H, d, J=17.1 Hz), 4.92 (1H, d, J=6.3 Hz), 4.79 (1H, t, J=7.8 Hz), 4.55 (1H, d, J=9.7 Hz), 4.28 (1H, d, J=8.7 Hz), 3.48 (1H, d, J=18.1 Hz), 3.38 (1H, d, J=18.1 Hz), 2.87 (1H, dd, J=17.1, 4.9 Hz), 2.60 (1H, dd, J=17.1, 4.9 Hz), 2.25 (1H, m), 1.07 (6H, m): MS [M+Na]$^+$ 770.

(3S)-3-{3-[(1S)-1-(Naphthalene-2-carbonylamino)-2-methyl-propyl]-5-phenylmethyl-4,5-dihydro-isoxazole-5-carbonylamino}-4-keto-pentanoic Acid (Compound 23, Diastereomeric)

$^1$H NMR (500 MHz, DMSO-d$_6$) δ 8.72–8.55 (2H, m), 8.38 (1H, s), 8.04–7.85 (4H, m), 7.62 (2H, m), 7.25–7.12 (7H, m), 6.91–6.70 (3H, m), 4.79–4.51 (4H, m), 3.40–3.05 (4H, m), 2.73–2.23 (2H, m), 2.01 (1H, m), 0.94–0.70 (6H, m): MS [M+Na]$^+$ 658.

(3S)-3-{3-[(1S)-1-(Naphthalene-2-carbonylamino)-2-methyl-propyl]-5-phenylmethyl-4,5-dihydro-isoxazole-5-carbonylamino}-4-keto-5-(2,6-dichlorobenzoyloxy)-pentanoic Acid (Compound 28)

From less polar t-butyl ester: $^1$H NMR (500 MHz, DMSO-d$_6$) δ 8.68 (1H, d, J=8.8 Hz), 8.59 (1H, d, J=8.3 Hz), 8.40 (1H, s), 8.05–7.87 (4H, m), 7.63–7.54 (5H, m), 7.21–7.13 (5H, m), 5.98 (2H, ABq, J=17.1 Hz), 4.74 (1H, m), 4.64 (1H, m), 325–3.10 (4H, m), 2.62 (1H, dd, J=17.1, 6.3 Hz), 2.37 (1H, dd, J=16.6, 5.4 Hz), 2.06 (1H, m), 0.93 (3H, d, J=6.8 Hz), 0.83 (3H, d, J=6.2 Hz): MS [M+Na]$^+$ 754; From more polar t-butyl ester: $^1$H NMR (500 MHz, DMSO-d$_6$) δ 8.72 (1H, d, J=8.3 Hz), 8.59 91H, d, J=8.8 Hz), 8.41 (1H, s), 8.01–7.87 (4H, m), 7.62–7.53 (5H, m), 7.29–7.21 (5H, m), 4.70–4.55 (4H, m), 3.44–3.10 (4H, m), 2.72–2.67 (1H, dd, J=16.6, 7.3 Hz), 2.38–2.34 (1H, dd, J=16.6, 7.3 Hz), 2.05 (1H, m), 0.97 (3H d, J=6.3 Hz), 0.79 (3H, d, J=6.3 Hz); MS [M+Na]$^+$ 754.

(3S)-3-{3-[(1S)-1-(Quinoline-2-yl-carbonylamino)-2-methyl-propyl]-5-phenoxymethyl-4,5-dihydro-isoxazole-5-carbonylamino}-4-keto-pentanoic Acid (Compound 22, Diastereomeric Mixture)

$^1$H NMR (500 MHz, DMSO-d$_6$) δ 9.06 (1H, m), 8.82 91H, br), 8.57 (1H, m), 8.16–7.74 95H, m), 7.26–7.12 (4H, m), 6.89–6.69 (6H, m), 5.10–4.70 (4H, m), 4.48–4.20 (2H, m), 2.87–2.53 (2H, m), 2.32 (1H, m), 0.98–0.85 (6H, m): MS [M+Na]$^+$ 675, [M+H]$^+$ 653.

(3S)-3-{3-[(1S)-1-(Naphthalene-2-carbonylamino)-2-methyl-propyl]-5-phenoxymethyl-4,5-dihydro-isoxazole-5-carbonylamino}-4-keto-5-(2-naphthyloxy)-pentanoic Acid (Compound 25)

From less polar t-butyl ester: $^1$H NMR (500 MHz, DMSO-d$_6$) δ 8.96 (1H, d, J=7.8 Hz), 8.77 (1H, d, J=8.3 Hz), 8.47 (1H, s), 8.03–7.57 (9H, m), 7.44 (1H, t, J=6.8 Hz), 7.34 (1H, t, J=7.8 Hz), 7.17–7.13 (4H, m), 6.88–6.82 (3H, m), 5.09 (2H, ABq), 4.84 (1H, m), 4.72 (1H, m), 4.38 (1H, d, J=10.2 Hz), 4.23 (1H, d, J=10.7 Hz), 2.94 (1H, dd, J=17.1, 6.8 Hz), 2.65 (1H, dd, J=16.6, 5.9 Hz), 2.12 (1H, m), 0.97 (3H, d, J=6.3 Hz), 0.85 (3H, d, J=6.3 Hz): MS [M+Na]$^+$ 724; From more polar t-butyl ester: $^1$H NMR (50° C., 300 MHz, DMSO-d$_6$) δ 8.72 (1H, d), 8.63 (1H, d), 8.41 (1H, s), 7.94–6.72 (19H, m), 5.03 (2H, ABq), 4.88 (1H, m), 4.74 (1H, m), 4.42 91H, d), 4.19 (1H, m), 3.38 (2H, ABq), 2.88 (1H, dd), 2.65 (1H, dd), 2.19 (1H, m), 1.02 (6H, two d): MS [M+Na]$^+$ 724; $^{13}$C NMR (50° C., 300 MHz, DMSO-d$_6$) δ 202.1, 171.6, 170.7, 166.6, 159.3, 158.0, 155.6, 134.1, 133.9, 132.0, 131.6, 129.3, 129.1, 128.7, 127.7, 127.5, 127.3, 126.5, 126.2, 124.2, 123.6, 121.1, 118.1, 114.5, 107.4, 87.5, 70.2, 52.9, 34.4, 29.6, 19.4, 18.9. More polar diastereomer's methyl ester: $^1$H NMR (500 MHz, CDCl$_3$) δ

8.29 (1H, s), 8.02–6.68 (20H, m), 5.09–4.95 (2H, ABq, J=16.6 Hz), 5.10 (1H, m), 5.01 (1H, m), 4.34 (2H, ABq, J=10.3 Hz), 3.70 (3H, s), 3.50–3.33 (2H, ABq, J=17.6 Hz), 3.13 (1H, dd, J=17.1, 4.9 Hz), 2.90 (1H, dd, J=17.1, 5.9 Hz), 2.23 (1H, m), 1.08 and 1.02 (6H, two d, J=6.8 Hz).

(3S)-3-{3-[(1S)-1-(Naphthalene-2-carbonylamino)-2-methyl-propyl]-5-phenoxymethyl-4,5-dihydro-isoxazole-5-carbonylamino}-4-keto-5-(1-naphthyloxy)-pentanoic Acid (Compound 24, Diasteromeric Mixture)

¹H NMR (500 MHz, DMSO-d₆) δ 9.02–8.18 (3H, m), 8.05–6.80 (18H, m), 5.15–4.15 (6H, m), 2.90–2.55 (2H, m), 2.14 (1H, m), 1.05–0.82 (6H, m).

(3S)-3-{3-[(1S)-1-(Naphthalene-2-carbonylamino)-2-methyl-propyl]-4,5-dihydro-isoxazole-5-carbonylamino}-4-keto-5-(2-naphthyloxy)-pentanoic Acid (Compound 29, Diasteromeric Mixture)

¹H NMR (500 MHz, DMSO-d₆) δ 8.95–8.46 (3H, m), 8.09–7.07 (13H, m), 5.21–4.75 (5H, m), 2.95–2.64 (2H, m), 2.19 (1H, m): MS [M+H]⁺ 596.

(3S)-3-{3-[2-Methyl-(1S)-1-(2-naphthalenecarbonylamino)-propyl]-4,5-dihydro-isoxazole-5-carbonylamino}-4-keto-5-phenoxy-pentanoic Acid (Compound 30, Diasteromeric Mixture)

¹H-NMR (500 MHz, DMSO-d₆) δ 8.76–8.69 (m, 2H), 8.45 (m, 1H), 8.04–7.90 (m, 5H), 7.61 (d, 2H), 7.31–7.19 (m, 2H), 6.97–6.81 (m, 3H), 5.09–4.68 (m, 5H), ~3.3 (m, 2H), 2.82 (m, 1H), 2.64 (m, 1H), 2.15 ((m, 1H), 1.00–0.84 (m, 6H): MS [M+Na]=568.

(3S)-3-{3-[2-Methyl-(1S)-1-(phenylethylcarbonylamino)-propyl]-5-phenylmethyl-4,5-dihydro-isoxazole-5-carbonylamino}-4-keto-5-dichlorobenzoyloxy)-pentanoic Acid (Compound 32, Diasteromeric Mixture)

¹H-NMR (500 MHz, DMSO-d₆) δ 8.48 (br s 1), 8.00 (m, 1H), 7.61–7.54 (m, 3H), 7.30–7.15 (m, 11H), 4.93–4.32 (m, 4H), 3.34–2.90 (m, 4H), 2.78 (m, 1H), 1.78 (m, 1H), 0.90–0.60 (m, 6H): MS [H+Na]=732.

(3S)-3-{3-[2-Methyl-(1S)-1-(1-naphthalenecarbonylamino)-propyl]-5-phenylmethyl-4,5-dihydro-isoxazole-5-carbonylamino}-4-keto-5-(2,6-dichlorobenzoyloxy)-pentanoic Acid (Compound 33)

From more polar t-butyl ester: ¹H-NMR (500 MHz, DMSO-d₆) δ 8.80 (d, J=8.3 Hz, 1H), 8.63 (d, J=7.8 Hz, 1H), 8.02 (m, 3H), 7.64–7.20 (m, 12H), 4.81–4.55 (m, 4H), 3.39 (m, 2H), 3.12 (m, 2H), 2.73 (m, 1H), 2.43 (m, 1H), 1.98 (m, 1H), 0.99 (d, J=4.6 Hz, 3H), 0.79 (d, J=4.5 Hz, 3H): MS [M+Na]=754; From less polar t-butyl ester: ¹H-NMR (500 MHz, DMSO-d₆) δ 8.77 (d, J=8.7 Hz, 1H), 8.62 (d, J=8.3 Hz, 1H), 8.08–7.97 (m, 4H), 7.61–7.21 (m, 12H), 5.00 (m, 2H), 4.77–4.67 (m, 2H), 3.39–3.27 (m, 2H), 3.15–3.11 (m, 2H), 2.64 (m, 1H), 2.40 (m, 1H), 1.99 (m, 1H), 0.96 (d, J=6.4 Hz 3H), 0.85 (d, J=6.9 Hz, 3H).

(3S)-3-{3-[2-Methyl-(1S)-1-(cinnamoylamino)-propyl]-5-phenylmethyl-4,5-dihydro-isoxazole-5-carbonylamino}-4-keto-5-(2,6-dichlorobenzoyloxy)-pentanoic Acid (Compound 38)

From more polar t-butyl ester: ¹H-NMR (500 MHz, DMSO-d₆) δ 8.55 (d, J=8.7 Hz, 1H), 8.28 (d, J=8.7 Hz, 1H), 7.60–7.19 (m, 14H), 6.70 (d, J=15.6 Hz, 1H), 4.71–4.49 (m, 4H), ~3.3 (m, 2H), 3.08 (m, 2H), 2.71 (m, 1H), 2.40 (m, 1H), 1.90 (m, 1H), 0.86 (d, J=6.4 Hz, 3H), 0.74 (d, J=6.4 Hz, 3H): MS [M+H]=708; From less polar t-butyl ester: ¹H-NMR (500 MHz, DMSO-d₆) δ 8.53 (d, J=8.3 Hz, 1H), 8.28 (d, J=8.7 Hz, 1H), 7.61–7.16 (m, 14H), 6.69 (d, J=16.9 Hz, 1H), 4.99–4.92 (ABq, J=17.4 Hz, 2H), 4.72 (m, 1H), 4.53 (m, 1H), 3.36 (d, J=17.9 Hz, 1H), 3.23 (d, J=13.8 Hz, 1H), 3.10–3.04 (m, 2H), 2.61 (dd, J=17.0, 6.4 Hz, 1H), 2.37 (dd, J=17.0, 6.0 Hz, 1H), 1.90 (m, 1H), 0.79 (m, 6H).

(3S)-3-{3-[2-Methyl-(1S)-1-(phenylmethylsulfonylamino)-propyl]-5-phenylmethyl-4,5-dihydro-isoxazole-5-carbonylamino}-4-keto-5-(2,6-dichlorobenzoyloxy)-pentanoic Acid (Compound 39, Diastereomeric)

¹H-NMR (500 MHz, DMSO-d₆) δ 7.75 and 7.69 (m, 1H), 7.61–7.13 (m, 13H), 5.00 and 4.70 (m, 1H), 4.64 (m, 2H), 4.22–3.78 (m, 4H), 1.79 (m, 1H), 0.90 (m, 6H): MS [M+H]=732.

(3S)-3-{3-[2-Methyl-(1S)-1-(quinoline-2-yl-carbonylamino)-propyl]-4,5-dihydro-isoxazole-5-carbonylamino}-4-keto-5-(2,6-dichlorobenzoyloxy)-pentanoic Acid (Compound 40)

From more polar isomer: ¹H-NMR (500 MHz, DMSO-d₆) δ 8.94 (d, J=9.7 Hz, 1H), 8.75 (d, J=7.8 Hz, 1H), 8.55 (d, J=8.8 Hz, 1H), 8.18–8.05 (d, 3H), 7.85 (d, 1H), 7.55 (m, 3H), 5.22–5.06 (m, 3H), 4.83–4.70 (m, 2H), 3.35 (m, 2H), 2.80 (m, 1H), 2.61 (m, 1H), 2.31 (m, 1H), 0.95 (m, 6H): MS [M+H]=643; From less polar isomer: ¹H-NMR (500 MHz, DMSO-d₆) δ 9.07 (d, J=9.2 Hz, 1H), 8.76 (d, J=8.3 Hz, 1H), 8.56 (d, J=8.7 Hz, 1H), 8.20–8.07 (m, 3H), 7.87 (m, 1H), 7.62–7.54 (m, 3H), 5.21–5.06 (m, 3H), 4.84–4.70 (m, 2H), 3.44–3.27 (m, 2H), 2.85 (dd, J=17.0, 6.0, 1H), 2.66 (dd, J=17.0, 6.9 Hz, 1H), 2.29 (m, 1H), 0.98 (d, J=6.9 Hz, 3H), 0.90 (d, J=6.4 Hz, 6H).

(3S)-3-{3-[2-Methyl-(1S)-1-(quinoline-2-yl-carbonylamino)-propyl]-4,5-dihydro-isoxazole-5-carbonylamino}-4-keto-5-phenoxy-pentanoic Acid (Compound 41)

From more polar isomer: ¹H-NMR (500 MHz, DMSO-d₆) δ 8.95 (d, 1H), 8.72 (d, 1H), 8.55 (d, 1H), 8.20–8.05 (m, 3H), 7.86 (m, 1H), 7.72 (m, 1H), 7.24–6.74 (m, 5H), 5.11–4.70 (m, 5H), 3.34 (m, 2H), 2.80 (m, 1H), 2.62 (m, 1H), 2.30 (m, 1H), 0.95 (m, 6H): MS [+H]=547; From less polar isomer: ¹H-NMR (500 MHz, DMSO-d₆) δ 9.03 (d, 1H), 8.74 (d, 1H), 8.56 (d, 1H), 8.20–8.07 (m, 3H), 7.87 (m, 1H), 7.73 (m, 1H), 7.23 (m, 2H), 6.88 (m, 3H), 5.09–4.71 (m, 5H), 3.34 (m, 2H), 2.85 (m, 1H), 2.65 (m, 1H), 2.27 (m, 1H), 0.96–0.87 (m, 6H).

(3S)-3-{3-[2-Methyl-(1S)-1-(quinoline-2-yl-carbonylamino)-propyl]-4,5-dihydro-isoxazole-5-carbonylamino}-4-keto-5-(2,6-dichlorobenzoyloxy)-pentanoic Acid (Compound 42)

From more polar isomer: ¹H-NMR (500 MHz, DMSO-d₆) δ 8.91 (d, J=9.2 Hz, 1H), 8.59–8.52 (m, 2H), 8.17–8.06 (m, 3H), 7.87 (m, 1H), 7.72 (m, 1H), 7.58–7.53 (m, 5H), 4.69–4.51 (m, 4H), 3.40 (m, 2H), 3.16 (m, 1H), 2.69 (m, 1H), 2.37 (m, 1H), 2.19 (m, 1H), 0.91–0.80 (m, 6H): MS [M+H]=733. From less polar isomer: ¹H-NMR (500 MHz, DMSO-d₆) δ 8.92 (d, J=9.2 Hz, 1H), 8.56 (m, 2H), 8.19–8.07 (m, 3H), 7.87 (m, 1H), 7.73 (m, 1H), 7.60–7.54 (m, 3H), 7.22–7.07 (m, 5H), 5.01–4.93 (ABq, J=16.5 Hz, 2H), 4.75–4.62 (m, 2H), 3.46 (d, J=18.4 Hz, 1H), 3.23–3.07 (m, 3H), 2.62 (dd, J=17.0, 6.9 Hz, 1H), 2.37 (dd, J=17.0, 6.0 Hz, 1H), 2.21 (m, 1H), 0.86–0.83 (m, 6H).

(3S)-3-{3-[2-Methyl-(1S)-1-(quinoline-2-yl-carbonylamino)-propyl]-5-phenylmethyl-4,5-dihydro-isoxazole-5-carbonylamino}-4-keto-5-phenoxy-pentanoic Acid (Compound 43)

From more polar isomer: ¹H-NMR (500 MHz, DMSO-d₆) δ 8.91 (d, J=9.2 Hz, 1H), 8.62 (d, J=8.3 Hz, 1H), 8.52 (d, J=8.7 Hz, 1H), 8.15 (d, J=8.3 Hz, 1H), 8.07 (m, 2H), 7.86 (m, 1H), 7.72 (m, 1H), 7.26–7.09 (m, 7H), 6.86 (m, 1H), 6.69 (d, J=8.3 Hz, 2H), 4.71–4.63 (m, 2H), 4.54–4.46 (ABq, J=17.9 Hz, 2H), 3.42 (d, J=17.9 Hz, 1H), 3.29 (d, J=13.8 Hz, 1H), 3.15 (d, J=18.4 Hz, 1H), 3.09 (d, J=14.3 Hz, 1H), 2.72 (dd, J=17.0, 6.9 Hz, 1H), 2.36 (dd, J=17.0, 6.0 Hz, 1H), 2.15 (m, 1H), 0.88 (d, J=6.9 Hz, 3H), 0.75 (d, J=6.9 Hz, 3H): MS

[M+H]=637; From less polar isomer: ¹H-NMR (500 MHz, DMSO-d₆) δ 8.88 (d, J=9.6 Hz, 1H), 8.54 (m, 2H), 8.18–8.06 (m, 3H), 7.87 (m, 1H), 7.72 (m, 1H), 7.28–6.78 (m, 10H), 4.78–4.63 (m, 4H), 3.45 (d, J=18.3 Hz, 1H), 3.26–3.06 (m, 3H), 2.66–2.62 (dd, J=17.0, 6.9 Hz, 1H), 2.44–2.39 (dd, J=17.0, 5.5 Hz, 1H), 2.17 (m, 1H), 0.80 (m, 6H).

(3S)-3-{3-[2-Methyl-(1S)-1-(quinoline-2-yl-carbonylamino)-propyl]-5-(1-imidazolylmethyl)-4,5-dihydro-isoxazole-5-carbonylamino}-4-keto-5-phenoxy-pentanoic Acid (Compound 44, Diastereomeric Mixture)

¹H-NMR (500 MHz, DMSO-d₆) δ 9.09–6.60 (m, 16H), 4.92–4.62 (m, 6H), 3.50 (m, 2H), 2.85–2.20 (m, 3H), 0.93 (m, 6H): MS [M+H]=627.

(3S)-3-{3-[2-Methyl-(1S)-1-(2-naphthalenecarbonylamino)-propyl]-4,5-dihydro-isoxazole-5-carbonylamino}-4-keto-pentanoic Acid (Compound 45, Diastereomeric Mixture)

¹H-NMR (500 MHz, DMSO-d₆) δ 8.77 (m, 1H), 8.45 (m, 2H), 8.07–7.89 (m, 4H), 7.61 (m, 2H), 5.06 (m, 1H), 4.72 (m, 1H), 4.46 & 4.38 (two m, 1H), ~3.3 (m, isoxaline CH₂), 2.62 (m, 1H), ~2.49 (m, 1H), 2.13 (m, 1H), 2.09 & 2.05 (two s, 3H), 1.01–0.84 (m, 6H).

(3S)-3-{3-[(1S)-1-(Succinoylamino)-3-carboxy-propyl]-5-methyl-4,5-dihydro-isoxazole-5-carbonylamino}-4-keto-5-phenoxy-pentanoic Acid (Compound 46, Diastereomeric Mixture)

¹H-NMR (500 MHz, DMSO-d₆) δ 8.56–8.52 (m, 1H), 8.15 (m, 1H), 7.27 (m, 2H), 6.97–6.82 (m, 3H), 4.96–4.83 (m, 2H), 4.77 (m, 1H), 4.58 (m, 1H), 3.58–2.22 (m, 10H), 2.0–1.74 (m, 2H), 1.47 & 1.45 (two s, 3H): MS [M+Na]=558.

(3S)-3-{3-[2-Methyl-(1S)-1-(succinoylamino)-propyl]-5-methyl-4,5-dihydro-isoxazole-5-carbonylamino}-4-keto-5-phenoxy-pentanoic Acid (Compound 47, Diastereomeric Mixture)

¹H-NMR (500 MHz, DMSO-d₆) δ 8.62–8.52 (m, 1H), 8.06 (m, 1H), 7.27 (m, 2H), 6.96–6.81 (m, 3H), 4.94–4.72 (m, 3H), 4.43–4.32 (m, 1H), 3.38–3.22 (m, 1H), 2.94–2.78 (m, 2H), 2.70–2.22 (m, 5H), 1.95–1.77 (m, 1H), 1.48 & 1.46 (two s, 3H), 0.86–0.70 (m, 6H): MS [M+Na]=528.

(3S)-3-{3-[2-Methyl-(1S)-1-(1-naphtalenycarbonylamino)-propyl]-5-phenylmethyl-4,5-dihydro-isoxazole-5-carbonylamino}-4-keto-5-(1-piperidinyl)-pentanoic Acid (Compound 48, Diastereomeric)

¹H-NMR (500 MHz, DMSO-d₆) δ 8.75 (m, 1H), 8.47 and 8.29 (m, 1H), 8.03–7.23 (m, 12H), 4.65 (m, 2H), 3.11–2.99 (m, 2H), 2.26–2.18 (m, 4H), 1.97 (m, 1H), 1.64–0.79 (m, 12H): MS [M+H]=627.

(3S)-3-{3-[2-Methyl-(1S)-1-(isoquinoline-1-carbonylamino)-propyl]-5-phenylmethyl-4,5-dihydro-isoxazole-5-carbonylamino}-4-keto-5-(2,6-dichlorobenzoyloxy)-pentanoic Acid (Compound 49LP)

¹H-NMR (500 MHz, DMSO-d₆) δ 9.03 (d, J=9.2 Hz, 1H), 8.74 (d, J=8.3 Hz, 1H), 8.60–8.56 (m, 2H), 8.07–8.03 (m, 2H), 7.83 (m, 1H), 7.73 (m, 1H), 7.61–7.53 (m, 3H), 7.22–7.17 (m, 5H), 5.01–4.93 (ABq, J=17.0 Hz, 2H), 4.74–4.63 (m, 2H), 3.41 (d, J=17.9 Hz, 1H), 3.23 (d, J=14.2 Hz, 1H), 3.13 (d, J=17,9 Hz, 1H), 3.09 (d, J=14.2 Hz, 1H), 2.60 (m, 1H), 2.36 (m, 1H), 2.10 (m, 1H), 0.91 (d, J=6.9 Hz, 3H), 0.84 (d, J=6.4 Hz, 3H).

(3S)-3-{3-[2-Methyl-(1S)-1-(isoquinoline-1-carbonylamino)-propyl]-5-phenylmethyl-4,5-dihydro-isoxazole-5-carbonylamino}-4-keto-5-(2,6-dichlorobenzoyloxy)-pentanoic Acid (Compound 50LP: Stereoisomer of 49LP)

¹H-NMR (500 MHz, DMSO-d₆) δ 9.04 (d, J=9.2 Hz, 1H), 8.65–8.60 (m, 2H), 8.53 (d, J=6.0 Hz, 1H), 8.05–8.60 (m, 2H), 7.82 (m, 1H), 7.72 (m, 1H), 7.60–7.53 (m, 3H), 7.30–7.17 (m, 5H), 4.75–4.53 (m, 4H), 3.5–3.3 (m, 2H, buried under solvent peaks), 3.13 (m, 2H), 2.68 (m, 1H), 2.41 (m, 1H), 2.04 (m, 1H), 0.95 (d, J=6.4 Hz, 3H), 0.78 (d, J=6.4 Hz, 3H).

(3S)-3-{3-[2-Methyl-(1S)-1-(isoquinoline-3-carbonylamino)-propyl]-5-phenylmethyl-4,5-dihydro-isoxazole-5-carbonylamino}-4-keto-5-(2,6-dichlorobenzoyloxy)-pentanoic Acid (Compound 51LP)

¹H-NMR (500 MHz, DMSO-d₆) δ 9.40 (s, 1H), 8.99 (d, J=9.2 Hz, 1H), 8.56 (m, 2H), 8.26 (d, J=7.8 Hz, 1H), 8.17 (d, J=7.8 Hz, 1H), 7.90–7.81 (m, 2H), 7.60–7.53 (m, 3H), 7.20–7.07 (m, 5H), 5.01–4.92 (ABq, J=17.0 Hz, 2H), 4.73–4.66 (m, 2H), ~3.4 (m, 1H, buried under solvent peaks), 3.23–3.05 (m, 3H), 2.60 (m, 1H), 2.34 (m, 1H), 2.19 (m, 1H), 0.82 (m, 6H).

(3S)-3-{3-[2-Methyl-(1S)-1-(isoquinoline-3-carbonylamino)-propyl]-5-phenylmethyl-4,5-dihydro-isoxazole-5-carbonylamino}-4-keto-5-(2,6-dichlorobenzoyloxy)-pentanoic Acid (Compound 52MP: Stereoisomer of Compound 51)

¹H-NMR (500 MHz, DMSO-d₆) δ 9.39 (s, 1H), 8.97 (d, J=9.6 Hz, 1H), 8.58 (d, J=8.7 Hz, 1H), 8.53 (s, 1H), 8.24 (d, J=8.3 Hz, 1H), 8.13 (d, J=7.8 Hz, 1H), 7.88–7.81 (m, 2H), 7.58–7.53 (m, 3H), 7.27–7.18 (m, 5H), 4.72–4.49 (m, 4H), 3.6–3.3 (m, 2H, buried under solvent peaks), 3.19–3.08 (m, 2H), 2.67 (m, 1H), 2.34 (m, 1H), 2.18 (m, 1H), 0.87 (d, J=6.9 Hz, 3H), 0.78 (d, J=6.9 Hz, 3H).

(3S)-3-{3-[2-Methyl-(1S)-1-(isoquinoline-4-carbonylamino)-propyl]-5-phenylmethyl-4,5-dihydro-isoxazole-5-carbonylamino}-4-keto-5-(2,6-dichlorobenzoyloxy)-pentanoic Acid (Compound 53 LP)

¹H-NMR (500 MHz, DMSO-d₆) δ 9.02 (m, 2H), 8.63 (d, J=8.7 Hz, 1H), 8.10 (d, J=8.3 Hz, 1H), 8.01 (d, J=7.8 Hz, 1H), 7.83 (m, 1H), 7.69 (m, 1H), 7.61–7.53 (m, 3H), 7.44 (d, J=4.2 Hz, 1H), 7.31–7.20 (m, 6H), 4.98 (m, 2H), 4.76–4.65 (m, 2H), 3.37 (d, J=17.9 Hz, 1H), 3.29 (d, J=14.2 Hz, 1H), 3.15–3.11 (m, 2H), 2.63 (m, 1H), 2.39 (m, 1H), 1.99 (m, 1H), 0.93 (d, J=6.9 Hz, 3H), 0.85 (d, J=6.9 Hz, 3H).

(3S)-3-{3-[2-Methyl-(1S)-1-(isoquinoline-4-carbonylamino)-propyl]-5-phenylmethyl-4,5-dihydro-isoxazole-5-carbonylamino}-4-keto-5-(2,6-dichlorobenzoyloxy)-pentanoic Acid (Compound 54 MP: Stereoisomer of Compound 53 LP)

¹H-NMR (500 MHz, DMSO-d₆) δ 9.05 (d, J=8.7 Hz, 1H), 8.96 (d, J=4.1 Hz, 1H), 8.64 (d, J=8.7 Hz, 1H), 8.08 (d, J=8.3 Hz, 1H), 7.99 (d, J=7.8 Hz, 1H), 7.82 (m, 1H), 7.69–7.48 (m, 5H), 7.31–7.20 (m, 5H), 4.80–4.55 (m, 4H), 3.6–3.3 (m, 2H, buried under solvent peaks), 3.14–3.09 (m, 2H), 2.72 (m, 1H), 2.41 (m, 1H), 1.95 (m, 1H), 0.96 (d, J=6.9 Hz, 3H), 0.78 (d, J=6.9 Hz, 3H).

(3S)-3-{3-[2-Methyl-(1S)-1-(benzofuran-2-carbonylamino)-propyl]-5-phenylmethyl-4,5-dihydro-isoxazole-5-carbonylamino}-4-keto-5-(2,6-dichlorobenzoyloxy)-pentanoic Acid (Compound 55LP)

¹H-NMR (500 MHz, DMSO-d₆) δ 8.83 (d, J=9.2 Hz, 1H), 8.56 (d, J=8.3 Hz, 1H), 7.79 (d, J=7.8 Hz, 1H), 7.68 (d, J=8.3 Hz, 1H), 7.61–7.33 (m, 6H), 7.20–7.04 (m, 5H), 5.00–4.92 (m, 2H), 4.73 (m, 1H), 4.56 (m, 1H), ~3.37 (m, 1H), 3.23–3.05 (m, 3H), 2.61 (m, 1H), 2.36 (m, 1H), 2.08 (m, 1H), 0.88–0.78 (m, 6H).

(3S)-3-{3-[2-Methyl-(1S)-1-(benzofuran-2-carbonylamino)-propyl]-5-phenylmethyl-4,5-dihydro-isoxazole-5-carbonylamino}-4-keto-5-(2,6-dichlorobenzoyloxy)-pentanoic Acid (Compound 56: Stereoisomer of Compound 55LP)

¹H-NMR (500 MHz, DMSO-d₆) δ 8.83 (d, J=9.2 Hz, 1H), 8.55 (d, J=8.7 Hz, 1H), 7.73 (d, J=7.8 Hz, 1H), 7.64 (d, J=8.2

Hz, 1H), 7.58–7.43 (m, 5H), 7.33–7.18 (m, 6H), 4.69–4.55 (m, 4H), 3.43–3.30 (m, 2H), 3.12–3.07 (m, 2H), 2.69 (m, 1H), 2.37 (m, 1H), 2.06 (m, 1H), 0.90 (d, J=6.4 Hz, 3H), 0.74 (d, J=6.4 Hz, 3H).

(3S)-3-{3-[2-Methyl-(1S)-1-(naphthalene-1-carbonylamino)-propyl]-5-phenylmethyl-4,5-dihydro-isoxazole-5-carbonylamino}-4-keto-5-(2,6-difluorobenzoyloxy)-pentanoic Acid (Compound 57LP)

$^1$H-NMR (500 MHz, DMSO-d$_6$) δ 8.77 (d, J=9.7 Hz, 1H), 8.64 (d, J=8.3 Hz, 1H), 8.06–7.95 (m, 3H), 7.69–7.44 (m, 5H), 7.26 (m, 7H), 5.02–4.90 (ABq, J=17.0 Hz, 2H), 4.71 (m, 2H), 3.30–3.10 (m, 4H), 2.65 (m, 1H), 2.39 (m, 1H), 1.99 (m, 1H), 0.94 (d, J=6.0 Hz, 3H), 0.84 (d, J=6.0 Hz, 3H).

(3S)-3-{3-[2-Methyl-(1S)-1-(naphthalene-1-carbonylamino)-propyl]-5-phenylmethyl-4,5-dihydro-isoxazole-5-carbonylamino}-4-keto-5-(2,6-dimethylbenzoyloxy)-pentanoic Acid (Compound 61: Diastereomeric Mixture)

$^1$H-NMR (500 MHz, DMSO-d$_6$) δ 8.82–8.76 (m, 1H), 8.65 (m, 1H), 8.08–7.95 (m, 3H), 7.59–7.46 (m, 4H), 7.33–7.06 (m, 8H), 4.98–4.49 (m, 4H), 3.42–3.09 (m, 4H), 2.76–2.39 (m, 2H), 2.28 & 2.25 (two s, 6H), 1.98 (m, 1H), 0.99–4.76 (m, 6H).

(3S)-3-{3-[2-Methyl-(1S)-1-(quinoline-8-carbonylamino)-propyl]-5-phenylmethyl-4,5-dihydro-isoxazole-5-carbonylamino}-4-keto-5-(2,6-dichlorobenzoyloxy)-pentanoic Acid (Compound 62: Diastereomeric Mixture)

$^1$H-NMR (500 MHz, DMSO-d$_6$) δ 11.19–11.08 (m, 1H), 9.04 (m, 1H), 8.65–8.50 (m, 3H), 8.22 (m, 1H), 7.80–7.51 (m, 5H), 7.30–7.06 (m, 5H), 5.00–4.47 (m, 4H), 3.46–3.02 (m, 4H), 2.73–2.34 (m, 2H), 2.11 (m, 1H), 1.00–0.80 (m, 6H).

(3S)-3-{3-[2-Methyl-(1S)-1-(indole-2-carbonylamino)-propyl]-5-phenylmethyl-4,5-dihydro-isoxazole-5-carbonylamino}-4-keto-5-(2,6-dichlorobenzoyloxy)-pentanoic Acid (Compound 63LP)

$^1$H-NMR (500 MHz, DMSO-d$_6$) δ 11.58 (s, 1H), 8.56 (d, J=8.7 Hz, 1H), 8.49 (d, J=8.7 Hz, 1H), 7.64–7.53 (m, 4H), 7.43 (d, J=8.3 Hz, 1H), 7.24–7.03 (m, 8H), 5.00–4.92 (ABq, J=17.0 Hz, 2H), 4.74–4.56 (m, 2H), ~3.5 (m, 1H, buried under solvent peaks), 3.23 (d, J=13.8 Hz, 1H), 3.15–3.06 (m, 2H), 2.60 (m, 1H), 2.35 (m, 1H), 2.02 (m, 1H), 0.90 (d, J=6.4 Hz, 3H), 0.81 (t, J=6.9 Hz, 3H).

(3S)-3-{3-[2-Methyl-(1S)-1-(indole-2-carbonylamino)-propyl]-5-phenylmethyl-4,5-dihydro-isoxazole-5-carbonylamino}-4-keto-5-(2,6-dichlorobenzoyloxy)-pentanoic Acid (Compound 64MP: Stereoisomer of Compound 63LP)

$^1$H-NMR (500 MHz, DMSO-d$_6$) δ 11.56 (s, 1H), 8.54 (m, 2H), 7.60–7.02 (m, 13H) 4.71–4.51 (m, 4H), 3.41–3.31 (m, 2H), 3.15–3.07 (m, 2H), 2.67 (m, 1H), 2.38 (m, 1H), 2.05 (m, 1H), 0.92 (d, J=6.9 Hz, 3H), 0.77 (d, J=6.9 Hz, 3H).

(3S)-3-{3-[2-Methyl-(1S)-1-(indole-3-carbonylamino)-propyl]-5-phenylmethyl-4,5-dihydro-isoxazole-5-carbonylamino}-4-keto-5-(2,6-dichlorobenzoyloxy)-pentanoic Acid (Compound 65LP)

$^1$H-NMR (500 MHz, DMSO-d$_6$) δ 11.61 (s, 1H), 8.56 (d, J=8.3 Hz, 1H), 8.08 (m, 2H), 7.91 (d, J=9.2 Hz, 1H), 7.62–7.54 (m, 3H), 7.43 (d, J=8.3 Hz, 1H), 7.22–7.00 (m, 7H), 4.95 (m, 2H), 4.72–4.61 (m, 2H), ~3.4 (m, 1H, buried under solvent peaks), 3.23 (d, J=13.8 Hz, 1H), 3.13–3.06 (m, 2H), 2.61 (m, 1H), 2.34 (m, 1H), 1.99 (m, 1H), 0.91 (d, J=6.4 Hz, 3H), 0.81 (d, J=6.4 Hz, 3H).

(3S)-3-{3-[2-Methyl-(1S)-1-(indole-3-carbonylamino)-propyl]-5-phenylmethyl-4,5-dihydro-isoxazole-5-carbonylamino}-4-keto-5-(2,6-dichlorobenzoyloxy)-pentanoic Acid (Compound 66MP: Stereoisomer of Compound 65LP)

$^1$H-NMR (500 MHz, DMSO-d$_6$) δ 11.60 (s, 1H), 8.54 (d, J=8.7 Hz, 1H), 8.11–8.06 (m, 2H), 7.91 (d, J=9.2 Hz, 1H), 7.60–7.05 (m, 11H), 4.71–4.47 (m, 4H), 3.33 (m, 2H), 3.09 (m, 2H), 2.68 (m, 2H), 2.39 (m, 1H), 2.00 (m, 1H), 0.93 (d, J=6.4 Hz, 3H), 0.78 (d, J=6.9 Hz, 3H).

(3S)-3-{3-[2-Methyl-(1S)-1-(naphthalene-1-carbonylamino)-propyl]-5-methyl-4,5-dihydro-isoxazole-5-carbonylamino}-4-keto-5-(2,6-dichlorobenzoyloxy)-pentanoic Acid (Compound 67LP)

$^1$H-NMR (500 MHz, DMSO-d$_6$) δ 8.86 (d, J=9.2 Hz, 1H), 8.73 (d, J=8.3 Hz, 1H), 8.11–7.98 (m, 3H), 7.64–7.54 (m, 7H), 5.17–5.08 (ABq, J=17.0 Hz, 2H), 4.81–4.70 (m, 2H), ~3.4 (m, 1H, buried under solvent peaks), 3.05 (d, J=17.9 Hz, 1H), 2.87 (m, 1H), 2.65 (m, 1H), 2.02 (m, 1H), 1.55 (s, 3H), 1.00 (d, J=6.4 Hz, 3H), 0.87 (d, J=6.4 Hz, 3H).

(3S)-3-{3-[2-Methyl-(1S)-1-(naphthalene-1-carbonylamino)-propyl]-5-methyl-4,5-dihydro-isoxazole-5-carbonylamino}-4-keto-5-(2,6-dichlorobenzoyloxy)-pentanoic Acid (Compound 68MP: Stereoisomer of Compound 67LP)

$^1$H-NMR (500 MHz, DMSO-d$_6$) δ 8.84 (d, J=8.7 Hz, 1H), 8.69 (d, J=8.3 Hz, 1H), 8.06–7.96 (m, 3H), 7.62–7.52 (m, 7H), 5.23–5.11 (ABq, J=17.0 Hz, 2H), 4.82–4.67 (m, 2H), 3.6–3.4 (m, 1H, buried under solvent peaks), 3.00 (d, J=17.9 Hz, 1H), 2.82 (m, 1H), 2.58 (m, 1H), 2.05 (m, 1H), 1.56 (s, 3H), 1.01–0.93 (m, 6H).

(3S)-3-{3-[2-Methyl-(1S)-1-(benzofuran-2-carbonylamino)-propyl]-5-methyl-4,5-dihydro-isoxazole-5-carbonylamino}-4-keto-5-(2,6-dichlorobenzoyloxy)-pentanoic Acid (Compound 69LP)

$^1$H-NMR (500 MHz, DMSO-d$_6$) δ 8.91 (d, J=8.7 Hz, 1H), 8.70 (d, J=8.2 Hz, 1H), 7.78 (d, J=7.8 Hz, 1H), 7.68 (d, J=8.3 Hz, 1H), 7.62–7.54 (m, 4H), 7.48 (m, 1H), 7.34 (m, 1H), 5.16–5.07 (ABq, J=17.0 Hz, 2H), 4.79 (m, 1H), 4.61 (m, 1H), 3.44 (d, J=17.9 Hz, 1H), 3.02 (d, J=17.9 Hz, 1H), 2.87 (dd, J=17.0, 6.0 Hz, 1H), 2.65 (dd, J=17.0, 7.4 Hz, 1H), 2.11 (m, 1H), 1.50 (s, 3H), 0.94 (d, J=6.9 Hz, 3H), 0.83 (d, J=6.4 Hz, 3H).

(3S)-3-{3-[2-Methyl-(1S)-1-(benzofuran-2-carbonylamino)-propyl]-5-methyl-4,5-dihydro-isoxazole-5-carbonylamino}-4-keto-5-(2,6-dichlorobenzoyloxy)-pentanoic Acid (Compound 70MP: Stereoisomer of Compound 69LP)

$^1$H-NMR (500 MHz, DMSO-d$_6$) δ 8.86 (d, J=8.7 Hz, 1H), 8.62 (d, J=7.8 Hz, 1H), 7.73 (d, J=7.8 Hz, 1H), 7.65 (d, J=8.3 Hz, 1H), 7.60–7.52 (m, 4H), 7.45 (m, 1H), 7.31 (m, 1H), 5.14–5.07 (ABq, J=17.0 Hz, 2H), 4.71 (m, 1H), 4.62 (m, 1H), 3.44 (d, J=17.9 Hz, 1H), 3.00 (d, J=17.9 Hz, 1H), 2.79 (dd, J=17.0, 6.4 Hz, 1H), 2.56 (dd, J=17.0, 6.0 Hz, 1H), 2.16 (m, 1H), 1.53 (s, 3H), 0.95–0.91 (m, 6H).

(3S)-3-{3-[3-Carboxy-(1S)-1-(succinoylamino)-propyl]-5-methyl-4,5-dihydro-isoxazole-5-carbonylamino}-4-keto-5-(2,6-dichlorobenzoyloxy)-pentanoic Acid (Compound 71LP)

$^1$H-NMR (500 MHz, DMSO-d$_6$) δ 8.60 (d, J=8.3 Hz, 1H), 8.15 (d, J=8.3 Hz, 1H), 7.61–7.54 (m, 3H), 5.16–5.08 (ABq, J=17.0 Hz, 2H), 4.78 (m, 1H), 4.62 (m, 1H), 3.31 (d, J=17.9 Hz, 1H), 2.90 (d, J=17.9 Hz, 1H), 2.85 (dd, J=17.0, 6.0 Hz, 1H), 2.64 (dd, J=17.0, 6.9 Hz, 1H), 2.44 (m, 2H), 2.33 (m, 2H), 2.24 (m, 2H), 1.90–1.76 (m, 2H), 1.46 (s, 3H).

(3S)-3-{3-[3-Carboxy-(1S)-1-(succinoylamino)-propyl]-5-methyl-4,5-dihydro-isoxazole-5-carbonylamino}-4-keto-5-(2,6-dichlorobenzoyloxy)-pentanoic Acid (Compound 72MP: Stereoisomer of Compound 71LP)

$^1$H-NMR (500 MHz, DMSO-d$_6$) δ 8.55 (d, J=8.3 Hz, 1H), 8.16 (d, J=8.3 Hz, 1H), 7.62–7.55 (m, 3H), 5.21–5.09 (ABq, J=17.0 Hz, 2H), 4.76 (m, 1H), 4.58 (m, 1H), 3.23 (d, J=17.9

Hz, 1H), 2.95 (d, J=17.9 Hz, 1H), 2.83 (dd, J=17.0, 6.5 Hz, 1H), 2.62 (dd, J=17.0, 6.4 Hz, 1H), 2.44 (m, 2H), 2.33 (m, 2H), 2.25 (m, 2H), 1.96 (m, 1H), 1.80 (m, 1H), 1.50 (s, 3H).

(3S)-3-{3-[2-Methyl-(1S)-1-(succinoylamino)-propyl]-5-methyl-4,5-dihydro-isoxazole-5-carbonylamino}-4-keto-5-(2,6-dichlorobenzoyloxy)-pentanoic Acid (Compound 73LP)

$^1$H-NMR (500 MHz, DMSO-$d_6$) δ 8.66 (d, J=8.3 Hz, 1H), 8.10 (d, J=8.7 Hz, 1H), 7.62–7.57 (m, 3H), 5.14–5.05 (ABq, J=17.0 Hz, 2H), 4.77 (m, 1H), 4.36 (m, 1H), 3.31 (d, J=18.4 Hz, 1H), 2.92 (d, J=18.4 Hz, 1H), 2.87–2.83 (m, 1H), 2.66–2.61 (m, 1H), 2.44 (m, 1H), 2.37 (m, 1H), 1.84 (m, 1H), 1.48 (s, 3H), 0.87 (d, J=6.4 Hz, 3H), 0.77 (d, J=6.4 Hz, 3H).

(3S)-3-{3-[2-Methyl-(1S)-1-(succinoylamino)-propyl]-5-methyl-4,5-dihydro-isoxazole-5-carbonylamino}-4-keto-5-(2,6-dichlorobenzoyloxy)-pentanoic Acid (Compound 74MP: Stereoisomer of Compound 73LP)

$^1$H-NMR (500 MHz, DMSO-$d_6$) δ 8.56 (d, J=8.3 Hz, 1H), 8.08 (d, J=8.7 Hz, 1H), 7.62–7.57 (m, 3H), 5.19–5.08 (ABq, J=17.0 Hz, 2H), 4.75 (m, 1H), 4.40 (m, 1H), 3.30 (d, J=17.9 Hz, 1H), 2.93 (d, J=17.9 Hz, 1H), 2.82 (m, 1H), 2.60 (m, 1H), 2.44–2.31 (m, 4H), 1.92 (m, 1H), 1.51 (s, 3H), 0.86–0.84 (m, 6H).

(3S)-3-{3-[2-Methyl-(1S)-1-(succinoylamino)-propyl]-5-propyl-4,5-dihydro-isoxazole-5-carbonylamino}-4-keto-5-(2,6-dichlorobenzoyloxy)-pentanoic Acid (Compound 75LP)

$^1$H-NMR (500 MHz, DMSO-$d_6$) δ 8.64 (d, J=8.3 Hz, 1H), 8.09 (d, J=8.7 Hz, 1H), 7.60 (m, 3H), 5.17–5.04 (ABq, J=17.0 Hz, 2H), 4.83 (m, 1H), 4.37 (m, 1H), 3.25 (t, J=17.9 Hz, 1H), 2.95 (d, J=17.9 Hz, 1H), 2.85 (m, J=17.0, 5.5 Hz, 1H), 2.65 (dd, J=16.5, 7.4 Hz, 1H), 2.46–2.35 (m, 4H), 1.84 (m, 2H), 1.70 (m, 1H), 1.36–1.15 (m, 2H), 0.88–0.76 (m, 9H).

(3S)-3-{3-[2-Methyl-(1S)-1-(succinoylamino)-propyl]-5-propyl-4,5-dihydro-isoxazole-5-carbonylamino}-4-keto-5-(2,6-dichlorobenzoyloxy)-pentanoic Acid (Compound 76MP: Stereoisomer of Compound 75LP)

$^1$H-NMR (500 MHz, DMSO-$d_6$) δ 8.59 (d, J=6.4 Hz, 1H), 8.07 (d, J=9.2 Hz, 1H), 7.62–7.54 (m, 3H), 5.12 (m, 2H), 4.74 (m, 1H), 4.40 (m, 1H), 3.24 (d, J=17.9 Hz, 1H), 2.95 (d, J=17.9 Hz, 1H), 2.82 (dd, J=17.0, 6.9 Hz, 1H), 2.59 (m, 1H), 2.44–2.30 (m, 4H), 1.92 (m, 2H), 1.71 (m, 1H), 1.38–1.20 (m, 2H), 0.85 (m, 9H).

(3S)-3-{3-[2-Methyl-(1S)-1-(succinoylamino)-propyl]-5-butyl-4,5-dihydro-isoxazole-5-carbonylamino}-4-keto-5-(2,6-dichlorobenzoyloxy)-pentanoic Acid (Compound 79LP)

$^1$H-NMR (500 MHz, DMSO-$d_6$) δ 8.63 (d, J=8.2 Hz, 1H), 8.09 (d, J=9.2 Hz, 1H), 7.62–7.57 (m, 3H), 5.17–5.05 (ABq, J=17.0 Hz, 2H), 4.83 (m, 1H), 4.37 (m, 1H), 3.25 (d, J=17.9 Hz, 1H), 2.95 (d, J=17.9 Hz, 1H), 2.85 (dd, J=17.0, 5.5 Hz, 1H), 2.65 (dd, J=17.0, 7.3 Hz, 1H), 2.45–2.35 (m, 4H), 1.84 (m, 2H), 1.71 (m, 1H), 1.28–1.14 (m, 4H), 0.88–0.76 (m, 9H).

(3S)-3-{3-[2-Methyl-(1S)-1-(succinoylamino)-propyl]-5-butyl-4,5-dihydro-isoxazole-5-carbonylamino}-4-keto-5-(2,6-dichlorobenzoyloxy)-pentanoic Acid (Compound 80MP: Stereomeric Isomer of Compound 79LP)

$^1$H-NMR (500 MHz, DMSO-$d_6$) δ 8.58 (d, J=8.3 Hz, 1H), 8.07 (d, J=8.7 Hz, 1H), 7.61–7.54 (m, 3H), 5.18–5.08 (ABq, J=17.0 Hz, 2H), 4.76 (m, 1H), 4.40 (m, 1H), 3.24 (d, J=17.9 Hz, 1H), 2.95 ((d, J=18.3 Hz, 1H), 2.83 (dd, J=16.5, 6.4 Hz, 1H), 2.59 (dd, J=17.0, 6.4 Hz, 1H), 2.45–2.30 (m, 4H), 1.92 (m, 2H), 1.73 (m, 1H), 1.36–1.16 (m, 4H), 0.87–0.83 (m, 9H).

(3S)-3-{3-[2-Methyl-carboxy-(1S)-1-(succinoylamino)-propyl]-5-methyl-4,5-dihydro-isoxazole-5-carbonylamino}-4-keto-5-(2,6-naphthyloxy)-pentanoic Acid (Compound 81LP)

$^1$H-NMR (500 MHz, DMSO-$d_6$) δ 8.67 (d, J=8.3 Hz, 1H), 8.08 (d, J=9.2 Hz, 1H), 7.83 (m, 2H), 7.73 (d, J=7.8 Hz, 1H), 7.46 (m, 1H), 7.36 (m, 1H), 7.18 (m, 2H), 5.01 (m, 2H), 4.83 (m, 1H), 4.34 (m, 1H), 3.30 (d, J=17.4 Hz, 1H), 2.93–2.87 (m, 2H), 2.67 (dd, J=17.0, 6.4 Hz, 1H), 2.45–2.34 (m, 4H), 1.79 (m, 1H), 1.49 (s, 3H), 0.80 (d, J=6.5 Hz, 3H), 0.68 (d, J=6.9 Hz, 3H).

(3S)-3-{3-[2-Methyl-carboxy-(1S)-1-(succinoylamino)-propyl]-5-methyl-4,5-dihydro-isoxazole-5-carbonylamino}-4-keto-5-(2-naphthyloxy)-pentanoic Acid (Compound 82MP Stereomeric Isomer of Compound 81LP)

$^1$H-NMR (500 MHz, DMSO-$d_6$) δ 8.58 (m, 1H) 7.8 Hz, 1H), 8.08 (d, J=9.2 Hz, 1H), 7.83 (m, 2H), 7.73 (d, J=7.8 Hz, 1H), 7.46 (m, 1H), 7.35 (m, 1H), 7.18 (m, 2H), 5.04 (m, 2H), 4.82 (m, 1H), 4.40 (m, 1H), 3.33 (d, J=17.4 Hz, 1H), 2.95–2.82 (m, 2H), 2.65 (m, 1H), 2.44–2.27 (m, 4H), 1.91 (m, 1H), 1.51 (s, 3H), 0.86–0.83 (m, 6H).

(3S)-3-{3-[2-Methyl-(1S)-1-(succinoylamino)-propyl]-5-propyl-4,5-dihydro-isoxazole-5-carbonylamino}-4-keto-5-phenoxy-pentanoic Acid (Compound 83: Diastereomeric Mixture)

$^1$H-NMR (500 MHz, DMSO-$d_6$) δ 8.57 (m, 1H), 8.06 (m, 1H), 7.26 (m, 2H), 6.94 (m, 1H), 6.83 (m, 2H), 4.92–4.71 (m, 3H), 4.41–4.34 (m, 1H), 3.26–3.21 (m, 1H), 2.96–2.78 (m, 2H), 2.67–2.56 (m, 1H), 2.44–2.25 (m, 4H), 1.92–1.66 (m, 3H), 1.40–1.16 (m, 2H), 0.88–0.70 (m, 9H).

(3S)-3-{3-[2-Methyl-(1S)-1-(succinoylamino)-propyl]-5-hydroxymethyl-4,5-dihydro-isoxazole-5-carbonylamino}-4-keto-5-(2,6-dichlorobenzoyloxy)-pentanoic Acid (Compound 84: Diastereomeric Mixture)

$^1$H-NMR (500 MHz, DMSO-$d_6$) δ 8.57 (d, J=8.3 Hz, 1H), 8.08 (d, J=8.7 Hz, 1H), 7.59 (m, 3H), 5.24–5.09 (m, 2H), 4.80 (m, 1H), 4.40 (m, 1H), 3.78 (m, 1H), 3.56 (m, 1H), 3.16–3.03 (m, 2H), 2.79 (m, 1H), 2.60 (m, 1H), 2.44–2.33 (m, 4H), 1.90 (m, 1H), 0.86–0.76 (m, 6H).

(3S)-3-{3-[2-Methyl-(S)-1-(succinoylamino)-propyl]-5-phenylmethyl-4,5-dihydro-isoxazole-5-carbonylamino}-4-keto-5-(2,6-dichlorobenzoyloxy)-pentanoic Acid (Compound 85LP)

$^1$H-NMR (500 MHz, DMSO-$d_6$) δ 8.51 (d, J=8.8 Hz, 1H), 8.05 (d, J=8.7 Hz, 1H), 7.59 (m, 3H), 7.25 (m, 5H), 4.92 (ABq, J=17.0 Hz, 2H), 4.70 (m, 1H), 4.34 (m, 1H), 3.34–3.20 (m, 2H), 3.07–3.02 (m, 2H), 2.58 (m, 1H), 2.44–2.30 (m, 5H), 1.82 (m, 1H), 0.81–0.73 (m, 6H).

(3S)-3-{3-[2-Methyl-(1S)-1-(succinoylamino)-propyl]-5-phenylmethyl-4,5-dihydro-isoxazole-5-carbonylamino}-4-keto-5-(2,6-dichlorobenzoyloxy)-pentanoic Acid (Compound 86MP: Diastereomer of Compound 85LP)

$^1$H-NMR (500 MHz, DMSO-$d_6$) δ 8.49 (d, J=8.7 Hz, 1H), 8.06 (d, J=8.7 Hz, 1H), 7.60 (m, 3H), 7.28–7.19 (m, 5H), 4.70 (m, 1H), 4.60–4.51 (ABq, J=17.4 Hz, 2H), 4.36 (m, 1H), 3.32–3.26 (m, 2H), 3.07–3.02 (m, 2H), 2.73–2.68 (m, 1H), 2.42–2.28 (m, 5H), 1.82 (m, 1H), 0.83 (d, J=6.9 Hz, 3H), 0.69 (d, J=6.9 Hz, 3H).

(3S)-3-{3-[2-Methyl-(1S)-1-(succinoylamino)-propyl]-5-methoxymethyl-4,5-dihydro-isoxazole-5-carbonylamino}-4-keto-5-(2,6-dichlorobenzoyloxy)-pentanoic Acid (Compound 87: Diastereomeric Mixture)

$^1$H-NMR (500 MHz, DMSO-$d_6$) δ 8.80 & 8.65 (two m, 1H), 8.10 & 7.97 (two m, 1H), 7.60 (m, 3H), 5.24–5.03 (m, 2H), 4.84 & 4.68 (two m, 1H), 4.39 (m, 1H), 3.78–3.51 (m, 2H), ~3.35 (two s, 3H), 3.20–2.99 (m, 2H), 2.91–2.50 (m, 2H), 2.44–2.34 (m, 4H), 1.85 (m, 1H), 0.87 (m, 6H).

(3S)-3-{3-[2-Methyl-(S)-1-(succinoylamino)-propyl]-5-n-pentyl-4,5-dihydro-isoxazole-5-carbonylamino}-keto-5-(2,6-dichlorobenzoyloxy)-pentanoic Acid (Compound 89LP)

$^1$H-NMR (500 MHz, DMSO-$d_6$) δ 8.64 (d, J=8.3 Hz, 1H), 8.10 (d, J=8.7 Hz, 1H), 7.60 (m, 3H), 5.16–5.05 (ABq,

J=16.5 Hz, 2H), 4.80 (m, 1H), 4.36 (m, 1H), 3.24 (d, J=17.5 Hz, 1H), 2.94 (d, J=17.9 Hz, 1H), 2.85 (m, 1H ), 2.64 (m, 1H), 2.45–2.36 (m, 4H), 1.84 (m, 2H), 1.70 (m, 1H), 1.23 (m, 6H), 0.86–0.76 (m, 6H).

(3S)-3-{3-[2-Methyl-(1S)-1-(succinoylamino)-propyl]-5-n-pentyl-4,5-dihydro-isoxazole-5-carbonylamino}-4-keto-5-(2,6-dichlorobenzoyloxy)-pentanoic Acid (Compound 90MP: Diastereomer of Compound 89LP $^1$H-NMR (500 MHz, DMSO-d$_6$) δ 8.59 (d, J=8.3 Hz, 1H), 8.07 (d, J=8.7 Hz, 1H), 7.60 (m, 3H), 5.18–5.08 (ABq, J=16.5 Hz, 2H), 4.76 (m, 1H), 4.40 (m, 1H), 3.24 (d, J=18.3 Hz, 1H), 2.95 (d, J=18.3 Hz, 1H), 2.82 (m, 1H), 2.58 (m, 1H), 2.44–2.30 (m, 4H), 1.92 (m, 2H), 1.72 (m, 1H), 1.23 (m, 6H), 0.85 (m, 6H).

(3S)-3-{3-[2-Methyl-(1S)-1-(succinoylamino)-propyl]-5-ethyl-4,5-dihydro-isoxazole-5-carbonylamino}-4-keto-5-(2,6-dichlorobenzoyloxy)-pentanoic Acid (Compound 91LP)

$^1$H-NMR (500 MHz, DMSO-d$_6$) δ 8.66 (d, J=8.3 Hz, 1H), 8.10 (d, J=8.7 Hz, 1H), 7.62–7.56 (m, 3H), 5.17–5.05 (ABq, J=16.5 Hz, 2H), 4.84 (m, 1H), 4.36 (m, 1H), 3.25 (d, J=17.9 Hz, 1H), 2.95 (d, J=17.9 Hz, 1H), 2.85 (m, 1H), 2.65 (m, 1H), 2.45–2.35 (m, 4H), 1.91–1.71 (m, 3H), 0.88–0.74 (m, 9H).

(3S)-3-{3-[2-Methyl-(1S)-1-(succinoylamino)-propyl]-5-ethyl-4,5-dihydro-isoxazole-5-carbonylamino}-4-keto-5-(2,6-dichlorobenzoyloxy)-pentanoic Acid (Compound 92MP: Diastereomer of Compound 91LP)

$^1$H-NMR (500 MHz, DMSO-d$_6$) δ 8.59 (d, J=7.8 Hz, 1H), 8.08 (d, J=9.2 Hz, 1H), 7.62–7.54 (m, 3H), 5.17–5.09 (ABq, J=17.0 Hz, 2H), 4.75 (m, 1H), 4.40 (m, 1H), 3.23 (d, J=18.3 Hz, 1H), 2.95 (d, J=17.8 Hz, 1H), 2.83 (m, 1H), 2.61 (m, 1H), 2.46–2.28 (m, 4H), 1.93 (m, 2H), 1.77 (m, 1H), 0.88–0.80 (m, 9H).

(3S)-3-{3-[2-Methyl-(1S)-1-(glutaroylamino)-propyl]-5-methyl-4,5-dihydro-isoxazole-5-carbonylamino}-4-keto-5-(2,6-dichlorobenzoyloxy)-pentanoic Acid (Compound 93LP)

$^1$H-NMR (500 MHz, DMSO-d$_6$) δ 8.66 (d, J=8.7 Hz, 1H), 8.07 (d, J=8.7 Hz, 1H), 7.61–7.54 (m, 3H), 5.14–5.05 (ABq, J=16.5 Hz, 2H), 4.79 (m, 1H), 4.40 (m, 1H), 3.32 (d, J=17.5 Hz, 1H), 2.90–2.83 (m, 2H), 2.63 (m, 1H), 2.18 (m, 4H), 1.85 (m, 1H), 1.72 (m, 2H), 1.48 (s, 3H), 0.86 (d, J=6.9 Hz, 3H), 0.77 (d, J=6.9 Hz, 3H).

(3S)-3-{3-[2-Methyl-(1S)-1-(glutaroylamino)-propyl]-5-methyl-4,5-dihydro-isoxazole-5-carbonylamino}-4-keto-5-(2,6-dichlorobenzoyloxy)-pentanoic Acid (Compound 94MP: Diastereomer of Compound 93LP)

$^1$H-NMR (500 MHz, DMSO-d$_6$) δ 8.58 (d, J=7.8 Hz, 1H), 8.05 (d, J=9.2 Hz, 1H), 7.62–7.54 (m, 3H), 5.18–5.08 (ABq, J=17.0 Hz, 2H), 4.76 (m, 1H), 4.41 (m, 1H), 3.31 (d, J=17.4 Hz, 1H), 2.92 (d, J=17.9 Hz, 1H), 2.80 (m, 1H), 2.60 (m, 1H), 2.16 (m, 4H), 1.91 (m, 1H), 1.70 (m, 2H), 1.51 (s, 3H), 0.85 (m, 6H).

Pharmacological Experiments

The pharmacological efficacy of the compound according to the present invention was evaluated by the following experiments. Con A was purchased from Boehringer Mannheim GmbH (Mannheim, Germany). Peptide-based substrates of caspases (Ac-YVAD-pNA for caspase-1, Ac-VDVAD for caspase-2, Ac-DEVD-pNA for caspase-3, 7, 8, and 9, Ac-LEVD-pNA for caspase-4, and Ac-VEID-pNA for caspase-6) and peptide-based caspase inhibitors (Ac-DEVD-fmk, z-VAD-CHO) were purchased from Alexis Co. (San Diego, Calif.). Ac-DEVD-CHO and z-DEVD-cmk were purchased from Bachem; Anti Fas antibody was purchased from Oncor (Cat#A8050); WI38 cell was available from ATCC; IFN-gamma was purchased from LG Pharmaceuticals (Korea). All cell culture-media and supplements were purchased from Gibco BRL (Tsuen Wan, Hong Kong) unless mentioned otherwise. Recombinant human caspases (1–4, 6–10) were prepared according to the method described in Garcia-Calvo M et al., "Purification and catalytic properties of human caspase family members", *Cell Death Differ.*, 1999, Apr.; 6(4): 362–9). Especially Caspase-3, -6, -7 and -8 are commercially available (Pharmingen, SanDiego, Calif., USA, Caspase-3: 66281T, Caspase-6: 66291T, Caspase-7: 66301T, Caspase-8: 66311T).

Experiment 1

Screening on Caspases Inhibiting Activity

In the present experiment recombinant caspases were purified from a transformed bacterium after human caspase genes were cloned into the expression vector pET, and then used in the experiment (Thornberry, N. A. et al. *Nature*, 1992, 356, 768. Thornberry, N. A. *Methods in Enzymology*, 1994, 615.).

Enzymatic activity was measured by a known procedure (Walker N. P. C. et al., *Cell* 1994, 78, 343). Briefly, 10 ng of recombinant protein was mixed with 50 mM Tris(pH 7.0), 1 mM DTT, 0.5 mM EDTA, 10% Glycerol buffer containing 1~100 μM of enzyme substrate, Ac-YVAD-AMC or Ac-DEVD-AMC and then the changes by isolated AMC at 37° C. were recorded. The inhibitory activity for caspases was calculated from the early enzyme reaction rate by measuring the changes with fluorescence excited at 380 nM and emitted at 460 nm (Range; Ki<100 nM).

Experiment 2

Screening for Intracelluar Inhibitory Efficacy for Caspases

Inhibitory activity for Caspase-1 was determined by screening the effects of the compounds on the IL-1β production in the periphery lymphocytes stimulated with LPS. Briefly, 500,000 cells/ml of human peripheral lymphocytes were treated with the test compounds at various concentrations for 2 hours and then with 10 ng/ml of LPS. After incubating the cells for 12 hours, the supernatant samples from the media were analysed by immunoantibody analysis (Amersham) in which 100 ng/well of human IL-1β antibody is coated (Range: CIC$_{50}$: 0.1~10 μM).

Meanwhile, the efficacy of the compounds on apoptosis was quantified by MTT assay in which cell death and survival ratio depending on the concentration of compounds were analyzed in Jurkat T cell treated with Anti-FAS antibody CHl1 which induces cell death (Effective range; 1.0~10 μM).

TABLE 1

| compound no. | Kobs/[I] for caspase-1 (M$^{-1}$sec$^{-1}$) | Kobs/[I] for caspase-3 (M$^{-1}$sec$^{-1}$) | CIC$_{50}$ (IL-1β production) | ED$_{50}$ FAS Induced cell death |
|---|---|---|---|---|
| Irreversible Inhibitors | | | | |
| 32 | 130000 | 114 | 0.1–10 μM | 1–10 μM |
| 33 mn | 807000 | 500 | " | " |
| 36 mn | 294000 | 132 | " | " |
| 42 mn | 408000 | 160 | " | " |
| 58 | 577000 | 371 | " | " |
| 64 | 707000 | 1230 | " | " |

TABLE 1-continued

| 66 | 357000 | 1560 | " | " |
| 68 | 616000 | 2390 | " | " |
| 72 | 30800 | 176000 | " | " |
| 74 | 14500 | 40900 | " | " |
| 76 | 14000 | 197000 | " | " |
| 80 | 14900 | 1140000 | " | " |
| 86 | 7560 | 28000 | | |
| 87 | 3400 | 27400 | | |
| 90 | | 80100 | | |

| compound no. | Ki for caspase-1 (nM) | Kobs/[I] for caspase-3 (uM) | CIC$_{50}$ (IL-1β production) | ED$_{50}$ FAS Induced cell death |
|---|---|---|---|---|
| Reversible Inhibitor | | | | |
| 22 mn | 0.125 | 19.2 | 0.1–10 μM | 1–10 μM |
| 25 mn | 0.0721 | 24.9 | " | " |
| 29 | 0.324 | 65.9 | " | " |
| 30 | 19.1 | 44.8 | " | " |
| 43 mn | 4.0 | 70.7 | " | " |
| 46 | 29.1 | 0.0806 | " | " |
| 47 | 177 | 0.85 | " | " |
| 48 | 1.51 | 199 | " | " |
| 77 | 28900 | 19.3 | " | " |
| 78 | 63900 | 45.5 | " | " |
| 81 | 26900 | 11.7 | " | " |
| 82 | 530 | 0.184 | " | " |
| 83 | 969 | 0.0277 | | |

Experiment 3

Hepatocyte Isolation and Cultivation

Male Sprague-Dawley rats (Hanlan Sprague-Dawley) were treated and bred as described by MacMicking et al., 1995, *Cell* 81: 641–650), and used as a source of liver cells. Rat hepatocytes were isolated, purified, and cultured as describe by Stadler et al., *Arch. Biochem. Biophys.* 302: 4–11). Highly purified hepatocytes (>98% purity and >98% viability by trypan blue exclusion) were suspended in Williams medium E containing 10% calf serum supplemented with 15 mM HEPES (pH 7.4), 1 μM insulin, 2 mM L-glutamine, 100 units/ml penicillin, and 100 μg/ml streptomycin. The cells were plated on collagen-coated plates with a density of $2 \times 10^5$ cells/well in a 12-well plate for cell viability test or $5 \times 10^6$ cells/100 ml dish for enzyme assay.

Experiment 4

In vitro Assay for Inhibition of Caspase Activity in Cell Free System

Caspase activity was tested by mewing proteolytic cleavage of peptide-based chromogenic substrate by each enzyme. Recombinant human caspase was preincubated with 5 mM DTT in assay buffer (100 mM HEPES, pH 7.4, containing 20% (v/v) glycerol) for 20 minutes at room temperature. Aliquots of the enzyme (2 μl containing catalytic activity of 0.2 absorbance at 405 nm/h) were mixed with 150 μl of 200 μM chromogenic substrate in the presence or absence of 100 μM compound 33 m, 96-well plates. The mixture was incubated at 37° C. The absorbance of enzymatically released pNA was measured discontinuously at 405 nm in a microplate reader for 1 hr. The caspase activity was calculated from initial velocity (meant±SE)(n=4, in which n represents the number of repeated experiment). As a result, the compound of the invention almost completely inhibited all tested caspase activity, only except for caspase 2 (FIG. 1). This result indicates that the compound of the invention is a broad-spectrum caspase inhibitor.

Experiment 5

In vivo Assay for Inhibition of Caspase Activity in Rat Hepatocytes

Freshly isolated rat hepatocytes were treated with 2,000 units/ml TNFα plus 100 ng/ml actinomycin D to induce cellular apoptosis. The cells were harvested after 10 hrs. Cytosolic solution was obtained by lysing cells with three cycles of freezing and thawing and centrifuging at 12,000×g for 20 min. at 4° C. Cytosol (~2 μg of protein) was mixed with 200 μM specific chromogenic substrate in, 100 mM HEPES buffer (pH 7.4) containing 20% glycerol and 5 mM DTT in presence or absence of 100 μM compound 33 and incubated 37° C. The caspase activity was assayed by measuring the increased absorbance at 405 nm.

Strong enzyme activities were detected with Ac-DEVD-pNA (caspase-3, 7, 8 and 9), Ac-LEVD pNA (caspase-4), and Ac-VEm-pNA (caspase-6), and moderate enzyme activity was detected with Ac-VDVAD (caspase-2) (FIG. 2). The compound of the invention almost completely inhibited these amplified caspase activities, and the activity was comparable with peptide-based caspase inhibitors Ac-DEVD-fmk and z-VAD-CHO (FIG. 2). For Ac-YVAD-pNA (caspase-1), detected enzyme activity was relatively weak. However, the compound of the invention inhibited 74.1% of caspase-1-like activity.

Experiment 6

In vitro Assay for Enhancement of Cell Viability in Isolated Rat Hepatocytes The cells were treated with 2,000 units/ml TNFα plus 100 ng/ml actinomycin D with or without 100 μM caspase inhibitor (compound 33) for 12 hrs. Then cell viability was measured by crystal violet staining method (n=4).

Figure 3:
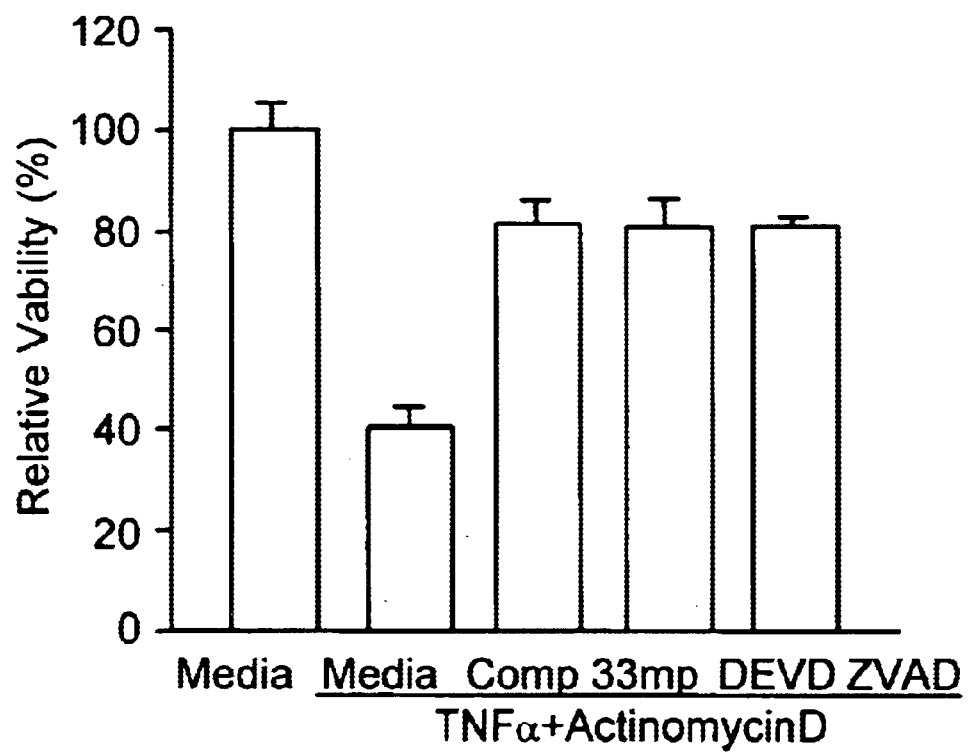
FIG. 3 represents a graph showing the effect of the compound of the invention on the prevention of apoptosis in rat hepatocytes in which apoptosis were derived by TNFα and Actinomycin D treatment.

As a result, the compound-of the invention prevented the death of rat hepatocytes (meant±SE)(FIG. 3). The result of this experiment indicates that the compound of the invention protected hepatocytes from apoptotic death induced by TNFα plus actinomycin D.

Experiment 7

Effect on Con A-Induced Acute Hapatitis Mice
Step 1: Preparation of Blood Sample Female 6-week-old Balb/c mice (Charles River Laboratory, Osaka, Japan) were kept at 22° C. and 55% relative humidity in a 12-h day/night rhythm with free access to food and water. Con A was dissolved in pyrogen-free saline to a concentration of 2.5 mg/ml and was injected via the tail vein in an amount of 20 mg/kg based on Con A. The animals were i.p. injected twice with compound 33 dissolved into a vehicle which consists of olive oil and 10% DMSO, or a vehicle alone, at 1 hr before and 4 h after Con A injection Animals were sacrificed by cervical dislocation at 24 hrs after Con A injection to obtain liver and blood samples.
Step 2: Assay for Plasma Aminotransferase Activity Blood samples obtained at step 1 were collected at 24 h after Con A injection Plasma AST and ALT activity were measured using Autokit (Youngdong Pharmaceutical Co., Seoul, Korea) following manufacturer's instruction.

Figure 4A:
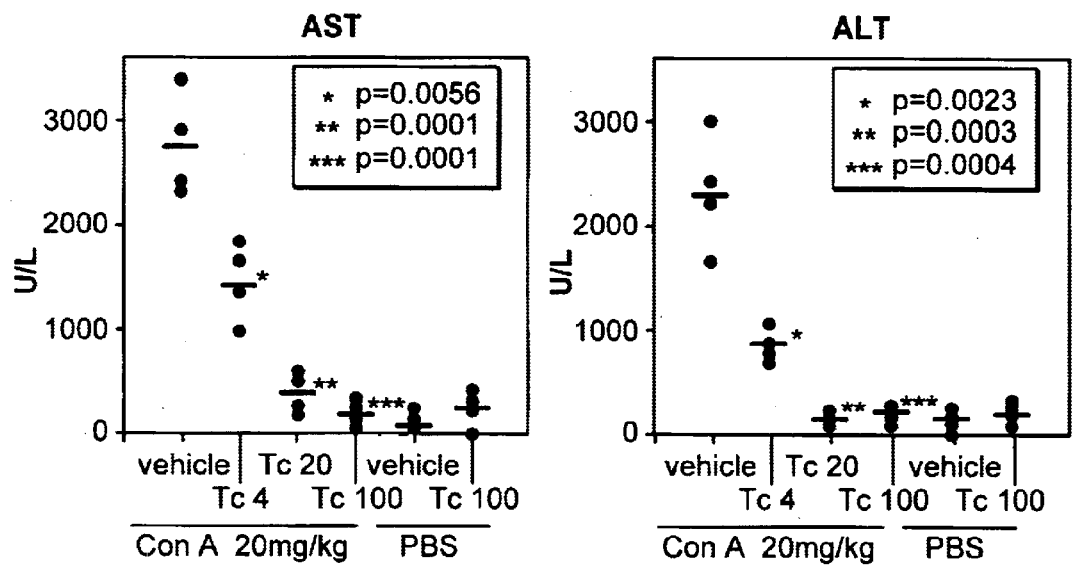
FIG. 4 represents a dose-dependent inhibitory activity of the compound of the invention against AST and ALT activities elevated by ConA in vivo, wherein the crossbars show the average of each group and p value was calculated by student's t-test.
Figure 4B:
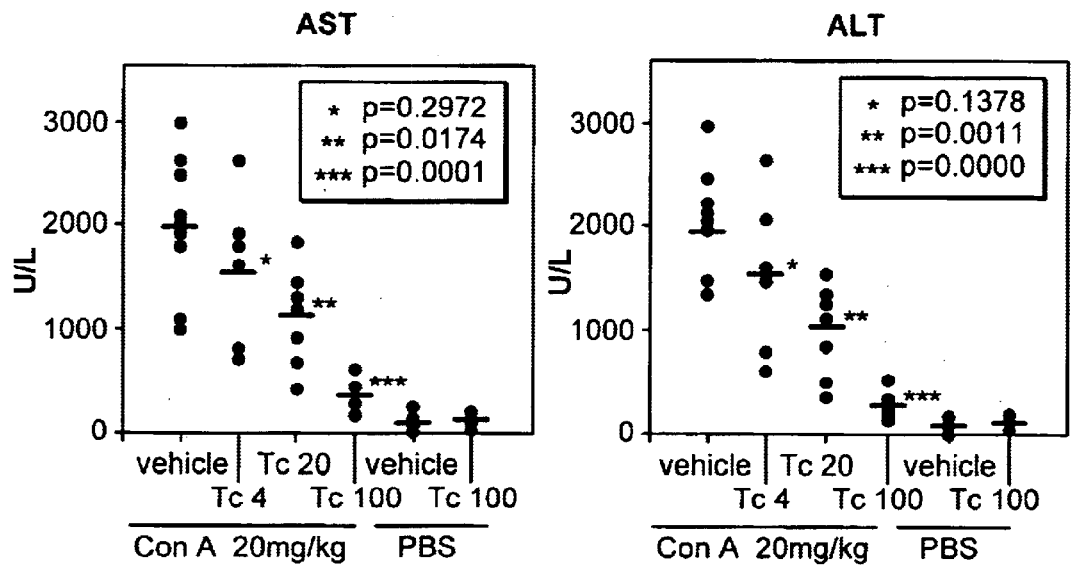

Two independent experiments were performed to confirm the result In the two experiments, ConA induced dramatic elevation of serum AST and ALT activity, and compound 33 suppressed the elevated enzyme activities in a dose-dependent manner (FIG. 4A, B). In the second experiment (FIG. 4B), the differences between Con A/vehicle group and Con A/4 mg/kg compound 33 group did not reached at statistically significant level (AST: p=0.2972, ALT: p=0.1378) since enzyme activities of each mouse showed some variation However, in 20 mg/kg of compound 33 group, AST and ALT activities were definitely reduced compared with ConA/vehicle group (AST: p=0.0174, ALT: p=0.0011). In the first experiment (FIG. 4A), compound 33 slightly increased AST activity by itself but this increase did not reach at statistically significant level (p=0.1033). These results indicate that the compound of formula (I) suppressed the elevated AST and ALT activities induced by Con A in vivo, but did not provoke significant liver toxicity by itself.

Step 3: Cytokine Assay

Although a large part of the pathogenesis of hepatic disease remains vague, several lines of evidence suggest that cytokines may be involved in the hepatic injury directly or by activating the immune system, and cytokine including TNFα, IL-2, IL-4, and INFγ by sandwich ELISA were reported to increase in patients with liver disease (See: Chisari, F. V., 1992, *Mol. Genet. Med.* 2: 67–104; Fukuda, R. et al., *Clin. Exp. Immunolol.* 100: 446–451; Yoshioka, K. et al., *Hepatology* 10: 769–773). Therefore, the present inventors assessed the effect of the present compound to serum cytokine concentrations elevated by Con A.

Blood samples were collected at 6 hrs after Con A injection at step 1. Murine IL-1β (Endogen Inc. Bostone, Mass.), IL-2, IL-4, IFNγ (Pharmingen, San Diego, Calif.) amounts in plasma were measured by ELISA kits. The assays were performed exactly as described by the manufacturer. Each sample was determined twice.

Figure 5:
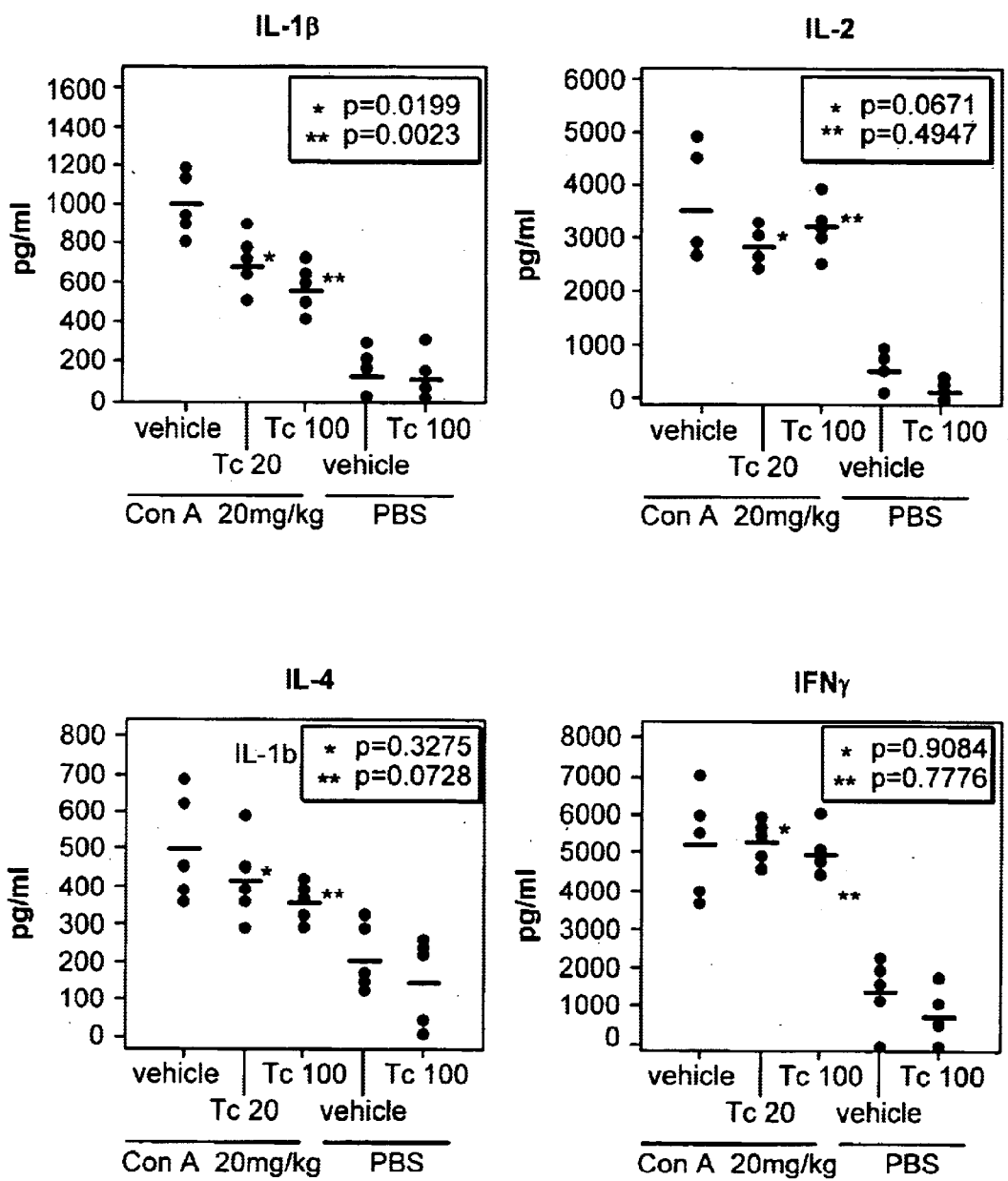
FIG. 5 represents a dose-dependent inhibition activity against cytokines elevated by ConA in vivo, wherein the crossbars show the average of each group and p value was calculated by students t-test.

The results showed that the compound of the invention suppressed the Con A-induced elevation of IL-1β in a dose-dependent manner (see FIG. 5). Meantime, the compound of the invention moderately reduced IL-4 concentration showing a dose-dependent tendency, but the differences between treat groups did not reach at statistically significant level. On the other hand, the compound of the invention did not significantly affect IL-2 and IFNγ concentrations. The compound of the invention itself slightly reduced all four cytokines compared with vehicle alone, but those differences did not reach at statistically significant level ($0.05<p<0.95$ for all 4 cytokines).

Experiment 8

Histologic Examination and Detection of Apoptosis

The present inventors estimated the prevalence of apoptotic cells in the mouse liver to certify the apoptosis-blocking effect of the compound of the present invention specifically in hepatocytes. Mice were treated ConA in the presence or absence of various dosages of compound 33 [A and G: ConA and vehicle treatment, B and H: ConA and compound 33 4 mg/kg treatment, C and I: ConA and compound 33 20 mg/kg treatment, D and J: ConA and compound 33 100 mg/kg treatment] to prepare frozen liver sections. Also, mice were treated with PBS and vehicle (E and K), or PBS and compound 33 100 mg/kg (F and L) to prepare frozen liver sections. Freshly excised mouse liver was immediately immersed in 25% sucrose solution at 4° C. for overnight, then frozen in liquid nitrogen, and cryosectioned into 4 μm.

For histological examination, liver sections were fixed in 1% buffered paraformaldehyde and stained with hematoxilin & eosin (FIGS. 6A to F). To detect apoptotic cells in liver, frozen liver was stained using an ApopTag in situ apoptosis peroxidase detection kit (terminal deoxynucleotidyl transferase-mediated dUTP nick end labeling: TUNEL assay) (Oncor, Gaithersburg, Md.) and DAKO liquid DAB (DAKO, Carpinteria, Calif.)(FIGS. 6G to L). Staining was conducted according to manufacturer's instruction After completion of staining, the samples were observed under an optical microscope. Each photograph represents typical results obtained from 10 mice per group. Histological examinations revealed that Con A induced severe morphological and histological changes to hepatocytes (FIG. 6A) and the apoptotic lesions were clearly detectable through the affected liver (FIG. 6G). However, in the liver of mice treated with the compound of the invention(Compound 33), the apoptotic lesions were reduced dose-dependently (FIGS. 6B–D), and cellular histology were gradually recovered with increasing dose of compound 33 (FIGS. 6H–J). These results indicated that the compound of the invention protected hepatocytes from the fatal apoptogenic effect of ConA.

Experiment 9

Western Blotting

In this experiment, the cleavage of PARP was identified by the appearance on Western blot analysis of an 85 kda-cleavage product in hepatic cell lysate obtained from mice treated with Con A and various doses of the compound of formula (I).

Freshly harvested livers treated with Con A or PBS together with various doses of compound 33 were rinsed in cold PBS and homogenized into three volumes per weight of cold PBS containing 1% Nonidet P-40, 0.1% SDS, 1 mM PMSF, and protease inhibitor cocktail tablet Complete (Boehnger Mannheim, used according to manufacturer's instruction). The homogenates were incubated on ice for 30 min. Samples were then centrifuged at 16,000×g for 30 min at 4° C. Supernatants were transferred to fresh tubes and centrifuged for additional 30 min. Harvested lysates were precleared by incubating with protein G-sepharose (Pharmacia, Uppsala, Sweden) at 4° C. for overnight, gently shaking. Supernatants were harvested by centrifugation at 1000×g for 30 sec. at 4° C. and separated on 7% SDS-polyacrylamide gel and transferred to nitrocellulose membrane. Blots were blocked for 1 hr at room temperature in PBS containing 5% skimmed milk and 0.1% Tween 20 under gentle shaking. Membranes were then incubated overnight with 1:1000 diluted monoclonal anti-PARP antibody (Pharmingen) under gentle shaking. After washing three times with PBS-Tween, the blots were hybridized with goat anti-mouse IgG-horse radish peroxidase (1:1000 dilution). After washing three times PBS-tween, signals were developed with ECL Western blotting kit (Amersham-Pharmacia Biotech, San Francisco, Calif.) and visualized by autoradiography.

In accordance with histological examination, the compound of the invention inhibited PARP cleavage caused by Con A-induced apoptotic death of hepatic cells (FIG. 7). The apoptosis-blocking effect of the compound appeared in a dose-dependent manner.

Experiment 10

Effect of the Caspase Inhibitor on the Protection of Apoptosis

In order to determine the efficacy of the compound according to the present invention on the protection of apoptosis, the following experiments were conducted.

W138 cells (human embryonal lung fibroblast) were grown in a medium containing DMEM-10% FBS within, 10 cm diameter dishes until reaching at confluency. The cells were seeded into a 24-well plate at day 1 and incubated overnight while the volume of medium was maintained to 400 μl. Cells were treated with 200 units/ml of IFNγ at day 2 and incubated over 12 hrs or more. At day 3, each 100 μl of test compound was added to the cells after diluting the 10 mM stock compound in DMSO to final concentrations of 50, 10, 2, and 0.4 μM, respectively. The cells were incubated for 2 hrs in order for allowing the compound to enter into the cells and then treated with 40 ng/well of anti-Fas antibody (apoptosis was induced 2 hrs after antibody was treated and the incubation was continued overnight). The control was not treated with Fas antibody. At day 4, after cells were observed with a microscope, 300 μl of medium per well and then 150 μl of XTT working solution were added to the medium and cultivation was continued for 2 hrs. After coloring, 100–200 μl of the supernatant was transferred to a 96-well plate and the absorbance at 490 nm was read with ELISA plate reader. For the blank, XTT solution was added to the well continued the medium only. Plotting was determined by comparing with the control group (100% when Fas antibody was not treated). The results thereof are shown in Table 2 below.

TABLE 2

| Conc. (μM) | IFN | IFN + Fas Ab | Ac-DEVD-CHO | z-DEVD-cmk | Comp 22 | Comp 28 | Comp 33 |
|---|---|---|---|---|---|---|---|
| 0 | 100 | 15.37 | | | | | |
| 0.4 | | | 12.16 | 15.13 | 14.44 | 14.67 | 15.51 |
| 2 | | | 14.75 | 16.27 | 18.32 | 17.33 | 64.44 |
| 10 | | | 19.16 | 27.38 | 35.37 | 82.40 | 92.68 |
| 50 | | | 35.14 | 47.32 | 78.29 | 90.39 | 100.21 |

As can be seen from the above table 2, only 15% of cells were survived when treated with the both IFNγ and the anti-Fas antibody together while the existing caspase inhibitors, Ac-DEVD-CHO (reversible inhibitor) or z-DEVD-cmk (irreversible inhibitor) treatment (50 μM) resulted in viability ratio of 35.1% and 47.3%, respectively. However, when treated with compound 22, compound 28, and compound 33 according to the invention at the same concentration, viability ratio was increased to 78%, 90%, 100%, respectively. Therefore, it is noted that the caspase inhibitors according to the invention prevented apoptosis much stronger than the existing drugs (See FIG. 8).

Experiment 11

Effect of the Caspase Inhibitor on anti-Fas Antibody-induced Liver Apoptosis

Step A: Animal Treatment

34 Weeks-old C57BL/6 female mice (18–20 g) were injected i.p. with compound 33MP dissolved in vehicle which consists of olive oil and 10% DMSO, or vehicle alone, at 1 hr before i.v. injection with 10 μg of Anti-Fas antibody (Jo2). Following 4 hrs of i.v. injection with Jo2 antibody, animals were placed under inhaled isoflurane anesthesia for blood collection and liver isolation. Mice were also i.p. injected with 0.2 μg/20 g of TNFα and 12 mg/20 g of D-galactosamine (TNFα/GalN) and compound 33MP or its salt form (Compound 33MP-Na). 8 hrs later, blood and liver tissues were isolated from anesthetized animals. The liver tissues were snap-frozen and stored at −80° C. until use. Plasma was isolated from blood by centrifugation at 12,000×g for 10 min at 4° C. and stored at −80° C. In some experiments for animal mortality, mice were i.p. injected with TNFα/GalN and caspase inhibitor was injected 1 hr before, simultaneously, 2 hrs, or 4 hrs after TNFα/GalN injection Step B: DNA Fragmentation Whole tissues (0.5 g) were homogenated in ice-cold lysis buffer (5 mM Tris, 20 mM EDTA, 0.5% Triton-X 100, pH8.0). The lysate was centrifuged at 12,000×g for 20 min at 4° C. The supernatant was obtained and extracted twice with a mixture of phenol and chloroform. One-tenth volume of 3 M sodium acetate was added to the solution, and DNA was precipitated by adding an equal volume of isopropanol. After storing at −20° C. overnight, a DNA pellet was obtained by centrifugation at 12,000×g for 15 min. at 4° C. and washed twice with 75% ethanol. The pellet was dried and resuspended in 100 μl of 20 mM Tris-HCl, pH 8.0. After digesting RNA with DNase-free RNase (0.1 mg/ml, at 37° C. for 1 hr, samples (15 ml) were electrophoresed through a 1.2% agarose gel in 450 mM Tris borate+EDTA (TBE), pH 8.0 buffer. DNA was photographed under visualized with UV light.

Step c: Enzyme Assay

Liver tissues were homogenated in 10 mM HEPES buffer containing protease inhibitors (5 μg/ml aprotinin, 5 μg/ml pepstatin A, 10 μg/ml leupeptin, and 0.5 mM PMSF) and lysed by three feeze/thaw cycles. The cytosolic fraction was obtained by centrifugation at 12,000×g for 20 min. at 4° C. Protein concentration was determined with BCA protein assay reagent (pierce, Rockford, Ill.). Cytosol containing 200 μg protein was combined in 96-well plate with 200 mM of synthetic substrate Ac-DEVD-pNA in 150 μl of 100 mM HEPES, pH 7.4, containing the protease inhibitors, and the reaction was conducted for 1 hr at 37° C. Cytosolic caspase-3-like activity was assayed by measuring the increased absorbance at 405 nm. Plasma level of aspartate aminotransferase (AST) was analyzed by spectrophotometry using each enzyme assay kit (Sigma).

Step D: Hepatocyte Culture and Treatment

Primary rat hepatocytes were isolated and purified from male Sprague-Dawley rats using a collagenase digestion method. The hepatocytes were purified over 30% Percoll gradient by centrifugation at 1,000×g for 10 min. at 4° C. Highly purified hepatocytes (>98% purity and >95% viability by trypan blue exclusion) were suspended in Williams medium E supplemented with 10% calf serum, 1 μM insulin, 2 mM L-glutamine, 15 mM HEPES (pH 7.4), 100 units/ml penicillin, and 100 μl/ml streptomycin. The cells were plated on collagen-coated tissue culture plates at a density of $2 \times 10^5$ cells/well in 12-well plates for cell viability analysis or $5 \times 10^6$ cells/100 mm dish for enzyme assays. After 18 hrs preculture, the cells were treated with 2,000 units/ml TNFα and 0.2 μg/ml Actinomycin (ActD). Caspase activity and cell viability was determined by colorimetry using a caspase substrate Ac-DEVD-pNA and crystal violet staining method at 8 hrs and 12 hrs, respectively.

Figures 9A, 9B:
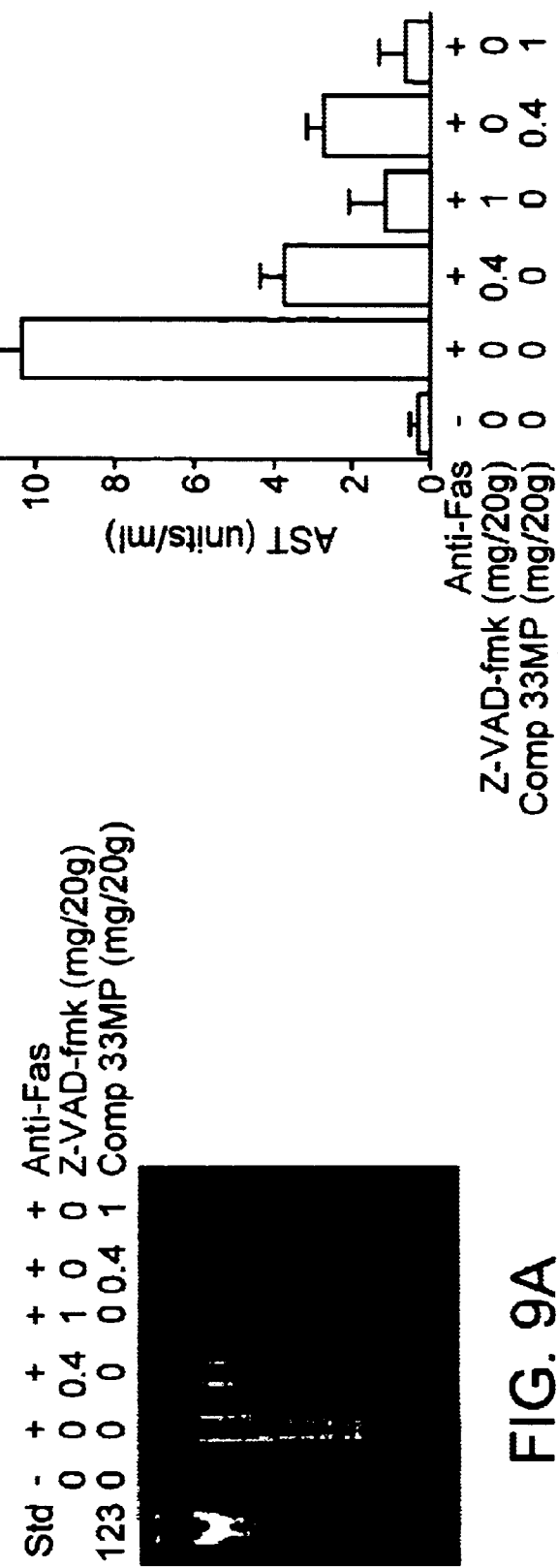
FIG. 9 represents hepatic protection of the compound of the invention from anti-Fas antibody-induced apoptosis.

As can be seen from the result of FIG. 9A, liver apoptosis from the mice injected with 0.4 mg/20 g, 1 mg/20 g of compound 33MP, or vehicle alone (olive oil and 10% DMSO) 1 hr before the antibody injection, as determined by DNA fragmentation, was significantly increased in anti-Fas antibody-injected animals after 4 hrs of the antibody injection. Treatment with compound 33MP was suppressed the liver apoptosis in a dose-dependent manner. The suppression was higher than that of well-known peptide caspase inhibitor Z-VAD-fmk. Similarly, the release of liver enzyme. AST was increased in animal treated with anti-Fas antibody (FIG.

Figure 10:
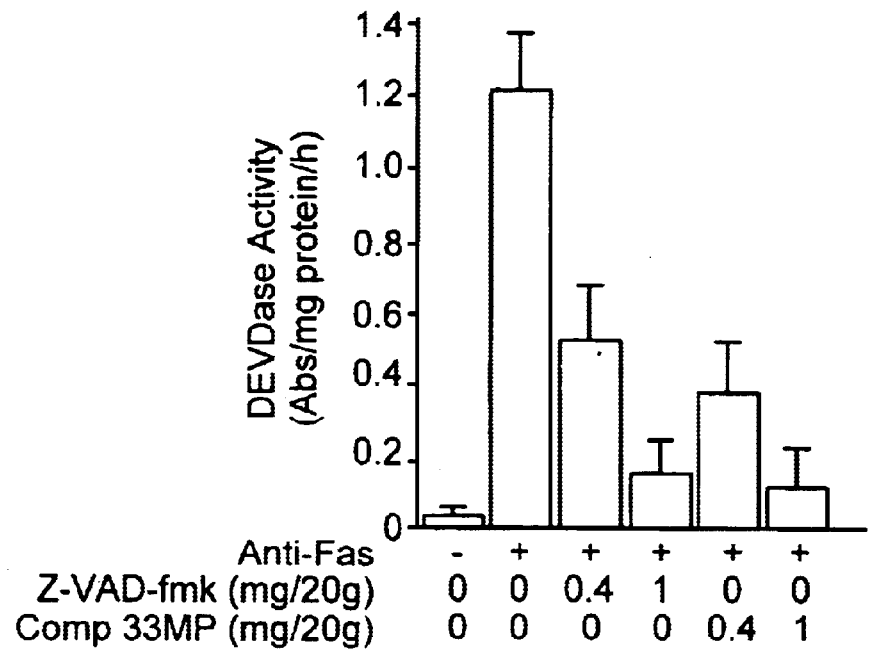
FIG. 10 is a graph showing inhibition activity of the compound of the invention against caspase-3-like activity in anti-Fas antibody-treated liver tissues.
Figure 11:
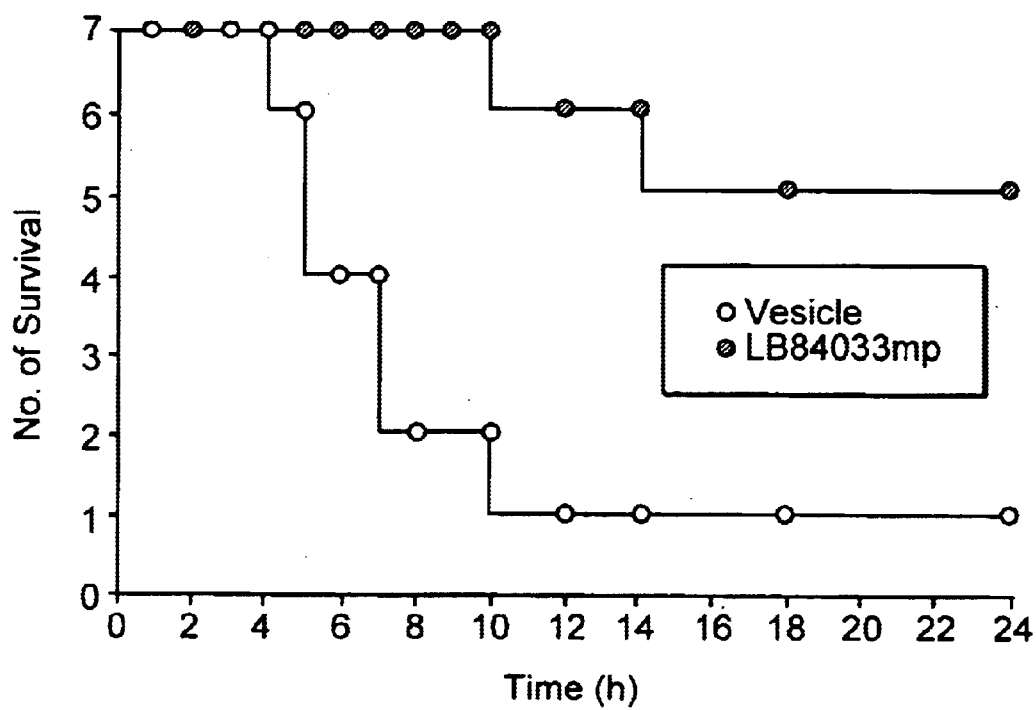
FIG. 11 represents protection of mice by the compound of the invention from anti-Fas antibody-induced lethality.

9B). The enzyme release was also significantly suppressed by the injection with compound 33M. This suppressive effect was higher than that of Z-VAD-fmk. These results indicate that compound 33MP can protect liver from anti-Fas antibody-induced liver damage. As the activation of caspase-3-like proteases is required for execution phase of apoptosis, caspase-3-like activity was assessed after anti-Fas antibody injection by measuring hydrolytic product of the caspase-3-like substrate Ac-DEVD-pNA at 405 nm. Caspase activity was increased by about 25-folds in liver tissues treated with the antibody (FIG. 10). The increased activity was abrogated by compound 33MP treatment. Furthermore, most of anti-Fas antibody-treated animals (85%) died within, 24 hrs, whereas treatment with compound 33MP reduced mortality by about 30% (FIG. 11). This inhibition was more effective than that of Z-VAD-fmk. This result suggests that inhibition of caspase activity and/or activation by compound 33MP is sufficient to protect mice from anti-Fas antibody-induced apoptotic mortality.

Figures 12A, 12B:
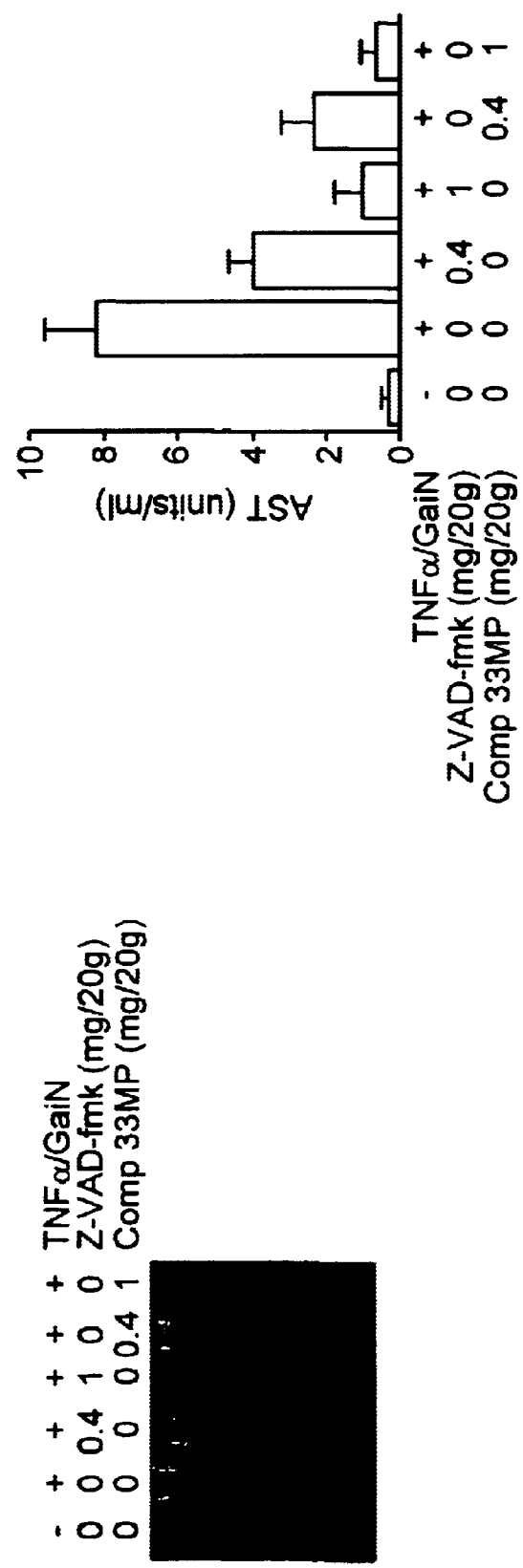
FIG. 12 is a graphical representation showing the protection of mice liver by the compound of the invention from TNFα-induced apoptosis.
Figure 13:
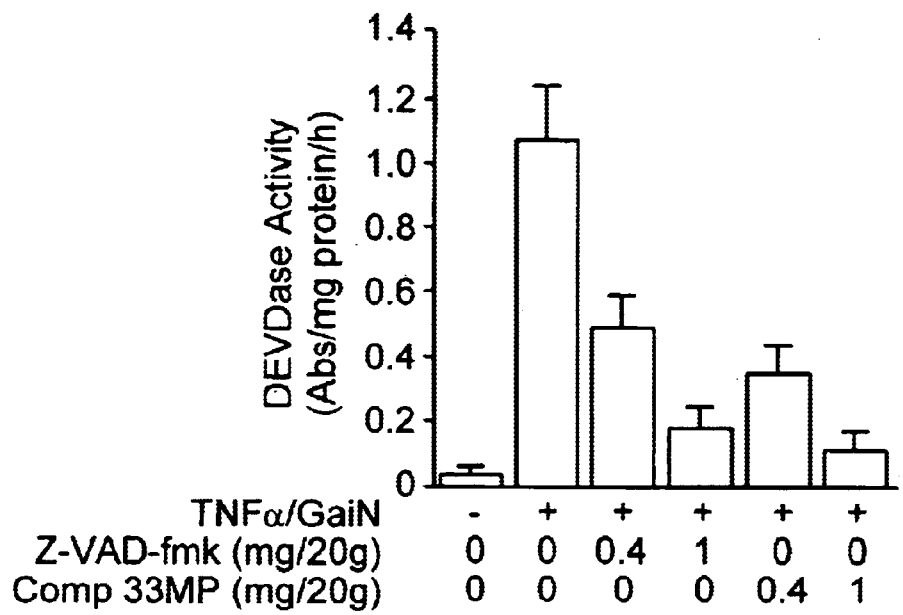
FIG. 13 is a graphical representation showing that the compound of the invention inhibits caspase-3-like activity in TNFα-treated liver.
Figure 14:
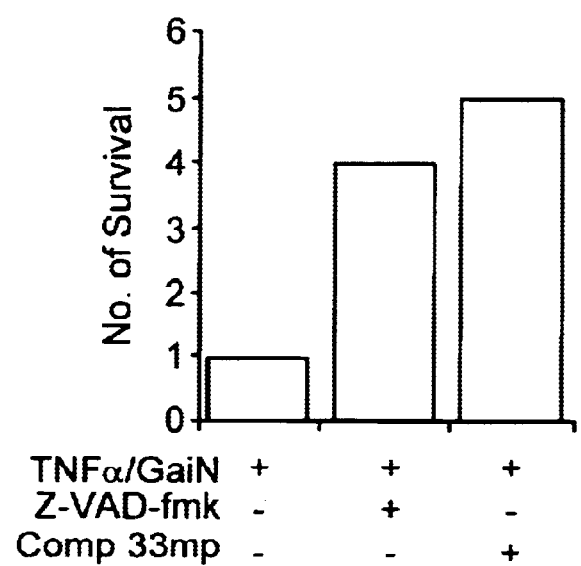
FIG. 14 is a graphical representation showing that the compound of the invention protects mice from TNFα-induced lethality.

Liver dysfunction and failure are common problems during endotoxemia and sepsis. It is generally accepted that proinflammatory cytokines, especially TNFα, are critical for the liver damage and mortality. We examined the effect of compound 33MP on TNFα-mediated liver toxicity. Treatment with TNFα/ActD induced DNA fragmentation in liver tissues and this toxicity was significantly reduced by administration of compound 33P (FIG. 12A). The release of AST following TNFα/ActD treatment was also suppressed by treatment with compound 33MP (FIG. 12B). The protective effect of compound 33MP was higher than that of Z-VAD-fmk. TNFα/ActD-mediated liver toxicity was accompanied by increase in caspase-3-like activity (FIG. 13). The increased caspase activity was suppressed by compound 33MP, which showed higher inhibitory effect than Z-VAD-fmk. These data indicate that the suppression of proapoptotic caspase activity by compound 33MP is correlated with the suppression of liver damage with apoptotic DNA fragmentation. Since fulminant liver damage and destruction are associated with animal mortality, we examined the effect of the compound of the invention on TNFα/ActD-mediated mouse mortality. When injected with TNFα/ActD and vehicle (olive oil and 10% DMSO), most of mice (~80%, 1 of 6) died within, 24 hrs, whereas 80% of compound 33 MP-treated animals survived (FIG. 14). Similar results were obtained by injection with Z-VAD-fmk. Thus, our results suggest that new non-peptide caspase inhibitor according to the invention may have therapeutic applications in the treatment of fulmimant liver damage.

Figure 15:
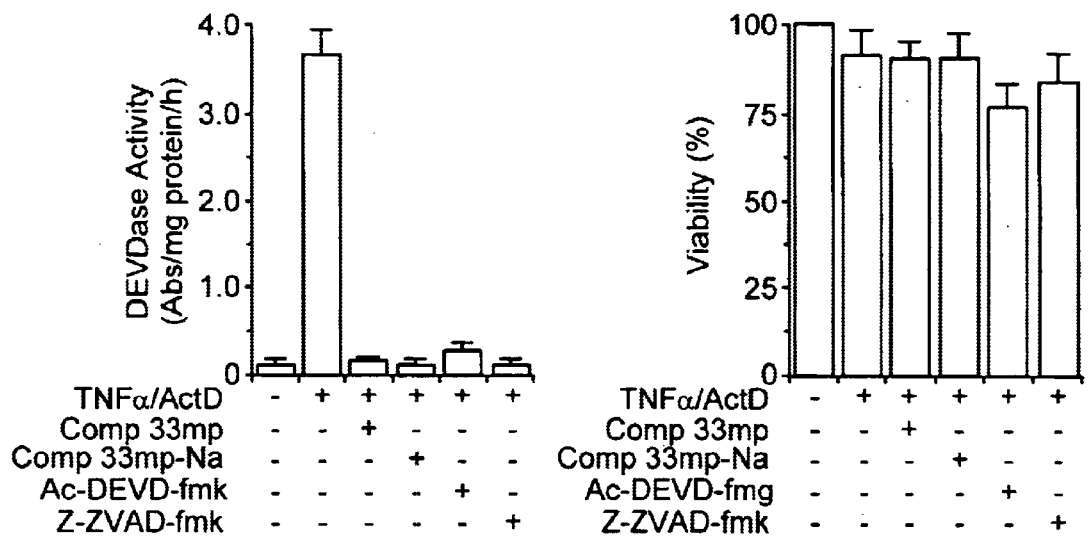
FIG. 15 is a graphical representation showing that the compound of the invention inhibits TNFα/Actinomycin D-induced caspase activation and apoptosis in primary cultured rat hepatocytes.

The inventors prepared the sodium salt form of compound 33 MP to increase its solubility and examined the effect of this compound (Compound 33MP-Na) on caspase activity and cell viability in TNFα/ActD-treated primary rat hepatocytes. Caspase-3-like activity was increased in cultured hepatocytes following treatment with TNFα/ActD for 8 hrs (FIG. 15A). This increase was suppressed by adding 100 μM compound 33MP-Na and this inhibition was not different from those of compound 33MP, Ac-DEVD-cho, or Z-VAD-fmk. Treatment with TNFα/ActD decreased cultured hepatocyte viability to about 30%. whereas all caspase inhibitors showed the similar protective effects on TNFα/ActD-induced hepatocyte apoptosis (FIG. 15B). These results indicate that cytoprotective effect of compound 33 MP-Na is not different from that of its non-salt form.

Figure 16:
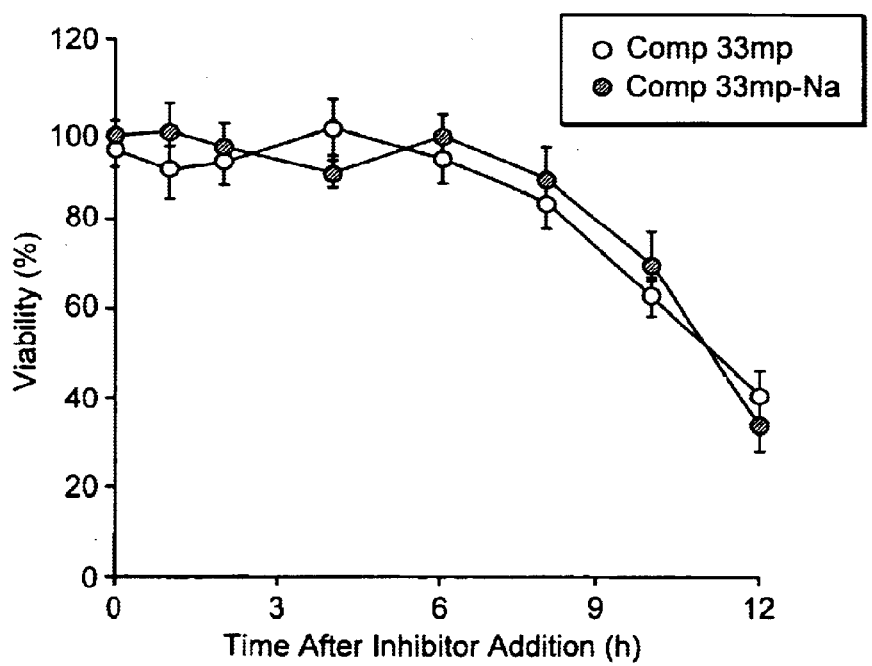
FIG. 16 is a graphical representation showing that the compound of the invention prevents hepatocyte apoptosis preinduced by TNFα/Actinomycin D.
Figure 17:
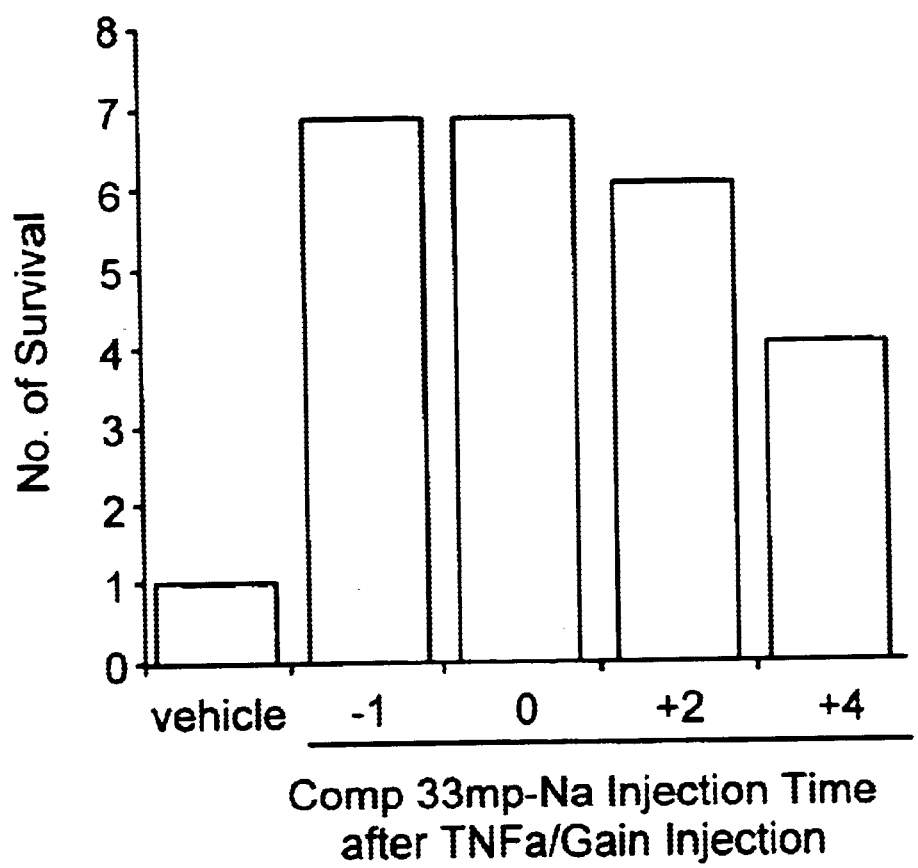
FIG. 17 is a graphical representation showing that the compound of the invention prevents TNFα/DaIN-mediated mortality.

Therapeutic drugs are administrated after diagnosis of disease symptoms. We examined the protective effect of the compound of the invention on preinduced hepatocyte toxicity. Hepatocytes were treated first with TNFα/ActD and then 100 μM of compound 33MP-Na was added at different time points. After 12 hrs of TNFα/ActD treatment, cell viability was determined by crystal violet staining. When added compound 33MP-Na between 0 and 6 hrs after TNFα/ActD treatment, cell viability was not decreased (FIG. 16). Addition of compound 33MP-Na after 6 hrs of TNFα/ActD treatment decreased cell viability in a time-dependent manner. No different results were obtained between compound 33MP-Na and Z-VAD-fmk. Treatment of mice with TNFα/ActD induced high mortality (95%). This mortality was significantly reduced (~80%) when injected with compound 33MP-Na at 1 hr before, 0 h, or 2 hrs after TNFα/ActD injection (FIG. 17). When administered 4 hrs after lethal challenge compound 33MP-Na still conferred a partial protection (50%). Moreover, death that occurs within, 10–14 hrs in TNFα/ActD-injected animals was significantly delayed up to 24 hrs for the non-surviving compound 33MP-Na (data not shown).

The above results with inhibition of both anti-Fas antibody and TNFα-mediated hepatocyte apoptosis provide the strong evidence that a simple galenic formulation of caspase-inhibiting drugs constitutes a new promising therapeutic strategy for acute liver disease involving uncontrolled apoptosis. Both the compound of the invention and its salt form can also be used for promising therapeutic drugs for fulminant liver damage and mortality.

What is claimed is:
1. An isoxazoline derivative of the formula (I)

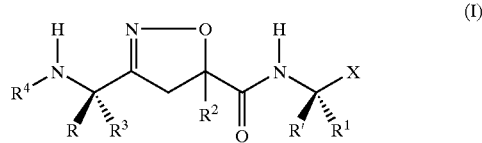

in which,
R and R' each independently represents hydrogen, simple alkyl chain (—SAC), simple cycloalkyl (—SCAC), aromatic (—Ar), or simple alkyl chain substituted with aromatic (—SAC—Ar);

$R^1$ represents —SAC, —SCAC, —Ar, or —SAC—Ar, or represents side chain of amino acids, or —$(CH_2)_n$COOZ (in which n is 1 or 2, and Z is hydrogen, —SAC, —Ar, or —SCAC);

$R^3$ represents —SAC, —SCAC, —Ar, or —SAC—Ar, or represents side chain of amino acids;

$R^2$ represents —SAC, —SCAC, —Ar, or —SAC—Ar, or represents a non-hydrogen side chain of amino acids, or represents —$(CH_2)_p(O)_mR^5$ (in which $R^5$=—SAC, —SCAC, —Ar, —SAC—Ar; p=0, 1 or 2; and m=0 or 1), or —$(CH_2)_qOC(=O)R^6$ (in which $R^6$=—SAC, —SCAC, —Ar, —SAC—Ar; and q=1 or 2);

$R^4$ represents
a) amino acid residue in which ① the carboxyl group attached to the chiral carbon of amino acid is bound to the amine group to form an amide bond, ② the chiral carbon of amino acid has either R or S configuration, ③ the amino group attached to the chiral carbon of amino acid is protected by formyl, acetyl, propyl, cyclopropylcarbonyl, butyl, methanesulfonyl, ethanesulfonyl, propanesulfonyl, butanesulfonyl, methoxycarbonyl, ethoxycarbonyl, propyloxycarbonyl, butyloxycarbonyl, methylcarbamoyl, ethylcarbamoyl, propylcarbamoyl, butylcarbamoyl, dimethylcarbamoyl, diethylcarbamoyl, dipropylcarbamoyl, dibutylcarbamoyl, or cyclopropylaminocarbonyl, or the amino group may be replaced with a hydrogen atom, and ④ the carboxyl group in the side chain may form an ester group with —SAC or —SCAC, b) —C('O)R$^7$ (in which R$^7$=—SAC, —SCAC, —Ar, —SAC—Ar), —CO$_2$R$^8$ (in which R$^8$=hydrogen or R$^7$), —C(=O)NR$^8$R$^8$, —SOR$^7$, or —C(=O)CH=CH—Ar, or c) —(C=O)—L—CO$_2$R$^8$, in which L represents a divalent (=capable of double substitution) linker selected from a group consisting of C$_{1-6}$ alkyl, C$_{3-8}$ cycloalkyl, furan, thiophene, diazole (1,2 or 1,3), triazole (1,2,3 or 1,3,4), tetrazole, oxazole, isoxazole, thiazole, isothiazole, diazine, (1,2 or 1,3 or 1,4), triazine, —Ph(—R$^9$)— (in which R$^9$=H, F, Cl, Br, I, CHO, OH, OCH$_3$, CF$_3$, OCF$_3$, CN, C(=O)Me), tetrahydrofuran, tetrahydrothiophene, 1,4-dioxane, —CH=C(R$^{10}$)— (in which R$^{10}$=H, methyl, ethyl), —CH=CHCH(R$^{10}$)—, —CH$_2$C(=O)CH$_2$—, and —C(=O)CH$_2$CH$_2$— in cases where R$^1$ and the adjacent R', and/or R$^3$ and the adjacent R are connected to each other to form a cyclic compound, R$^1$—R' or R$^3$—R together represents —(CH$_2$)$_n$—, —(CH$_2$)$_n$—O—(CH$_2$)$_m$—, or —(CH$_2$)$_n$—NR$^{13}$—(CH$_2$)$_m$— (in which n+m<9, R$^{13}$=—SAC, —SCAC, —Ar, —SAC—Ar, —C(O)—SAC, —C(=O)—SCAC, 'C(=O)—Ar, or —C(=O)—SAC—Ar;

X represents —CN, —CHO, —C(=O)R$^{14}$ (in which R$^{14}$=—SAC, —SCAC, —Ar, —SAC—Ar, —CHN$_2$), —C(=O)OR$^{15}$ (in which R$^{15}$=—SAC, —SCAC, —Ar, or —SAC—Ar), —CONR$^{16}$R$^{17}$ (in which R$^{16}$ and R$^{17}$ each represents —H, —SAC, —O—SAC, —SCAC, —Ar, or —SAC—Ar), —C(=O)CH$_2$O(C=O)Ar" (in which A"=2,6-disubstituted phenyl with F, Cl, Br, I, or CH$_3$), —C(=O)CH$_2$OR$^{18}$ (in which R$^{18}$ represents —SAC, —SCAC, —Ar, or —SAC—Ar), or —C(=O)CH$_2$OC(=O)R$^{19}$ (in which R$^{19}$=—SAC, —SCAC, —Ar, or —SAC—Ar), or X represents —COCH$_2$—W, wherein W represents —N$_2$, —F, —Cl, —Br, —I, —NR$^{20}$R$^{21}$ or —SR$^{22}$ (in which R$^{20}$, R$^{21}$ and R$^{22}$ each independently represents —SAC, —SCAC, —Ar, or —SAC—Ar or R$^{20}$ and R$^{21}$ are connected to form a cyclic compound) or W represents

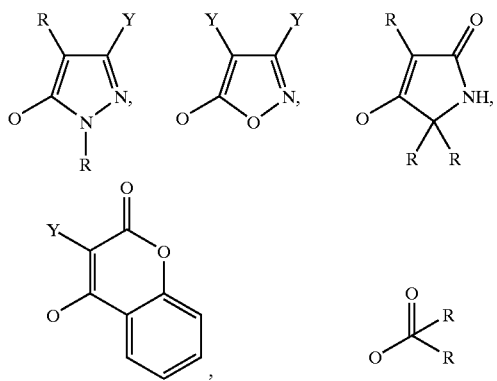

in which Y represents —OH, OR$^{23}$ (in which R$^{23}$=—SAC, or —SCAC), —C(=O)R$^{24}$ (in which R$^{24}$=—H, —SAC, or —SCAC), —F, —Cl, —Br, —I, —CN, —NC, —N$_3$, —CO$_2$H, —CF$_3$, —CO$_2$R$^{25}$ (in which R$^{25}$=—SAC, or —SCAC), —C(=O)NHR$^{26}$ (in which R$^{26}$=—SAC, or —SCAC), and —C(=O)NR$^{27}$R$^{28}$ (in which R$^{27}$, R$^{28}$=—SAC, or —SCAC) and can be mono-or poly-substituted at its maximum regardless of the order and the kinds, the pharmaceutically acceptable salts, the esters and the stereochemically isomeric forms thereof.

2. The compound of formula (I) according to claim 1, in which R$^4$ represents —C(=O)CH$_2$)$_p$COOZ (in which p is 1 to 4, and Z is hydrogen, —SAC, —Ar, or —SCAC).

3. The compound of formula (I) according to claim 1, in which R$^1$ represents —CH$_2$)$_n$COOZ (in which n is 1 or 2, and Z is hydrogen, —SAC, —Ar, or —SCAC).

4. The compound of formula (I) according to claim 1, in which a) R and R$^1$ represent hydrogen,
b) R$^1$ represents —CH$_2$COOH, —CH$_2$COOCH$_2$, or —CH$_2$COO CH$_2$CH$_3$,
c) R$^2$ represents —(CH$_2$)$_n$(O)$_m$R$^5$ (in which R$^5$=—SAC, —SCAC, —Ar, —SAC—Ar, n=0, 1 or 2; and m=0 or 1), —SAC, or —Ar,
d) R$^3$ represents —CH(CH$_3$)$_2$, —CH$_2$COOH, —(CH$_2$)$_2$CO$_2$H, —CH$_2$C(O)NH$_2$, or —(CH$_2$)$_2$C(O)NH$_2$,
e) R$^4$ represents —C(=O)(O)R$^{29}$ (in which n=0, 1; R$^{29}$=—Ar, or —SAC—Ar), —SO$_2$R$^{30}$ (in which R$^{30}$=—Ar or —SAC—Ar), or —C(=O)NHR$^{31}$ (in which R$^{31}$=—Ar, or —SAC—Ar), or
f) X represents —C(=O)CHN$_2$, —C(=O)CH$_2$Br, —C(=O)CH$_2$Cl, —C(=O)CH$_2$OPh, —C(=O)CH$_2$OC(=O)Ar" (in which Ar"=2,6-dichlorophenyl, 2,6-difluorophenyl or 2,6-dimethylphenyl).

5. The compound of formula (I) according to claim 1, which is selected from the group consisting of the following:

(3S)-3-{3-[(1S)-1-phenylmethyloxyocarbonylamino-2-methyl-propyl]-4,5-hydro-isoxazole-5-carbonylamino}-4-keto-pentanoic acid;

(3S)-3-{3-[(1S)-1-phenylmethyloxycarbonylamino-2-methyl-propyl]-5-phenoxymethyl-4,5-dihydro-isoxazole-5-carbonyl-amino}-4-keto-pentanoic acid;

(2S)-2-{3-[(1S)-1-phenylmethyloxycarbonylamino-2-methyl-propyl]-5-phenoxymethyl-4,5-dihydro-isoxazole-5-carbonyl-amino}-succinic acid 1-(N-methyl-N-methoxy)-amide;

(3S)-3-{3-[(1S)-1-phenylmethyloxycarbonylamino-2-methyl-propyl]-4,5-dihydro-isoxazole-5-carbonylamino}-4-keto-5-diazo-pentanoic acid;

(3S)-3-{3-[(1S)-1-phenylmethyloxycarbonylamino-2-methyl-propyl]-4,5-dihydro-isoxazole-5-carbonylamino}-4-keto-5-bromo-pentanoic acid;

(3S)-3-{3-[(1S)-1-phenylmethyloxycarbonylamino-2-methyl-propyl]-4,5-dihydro-isoxazole-5-carbonylamino}-4-keto-5-(2,6-dichlorobenzoyloxy)-pentanoic acid;

(3S)-3-{3-[(1S)-1-(naphthalene-1carbonylamino)-2-methyl-propyl]-5-phenoxymethyl-4,5-dihydro-isoxazole-5-carbonylamino}-4-keto-5-phenoxy-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-phenoxy-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-diazo-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-bromo-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-(2,6-dichlorobenzoyloxy)-pentanoic acid;

(3S)-3-{3-[(1S)-1-(naphthalene-2-carbonylamino)-2-methyl-propyl]-5-phenyl-methyl-4,5-dihydro-isoxazole-5-carbonylamino}-4-keto-5-diazo-pentanoic acid(LP and MP);

(3S)-3-{3-[(1S)-1-(naphthalene-2-carbonylamino)-2-methyl-propyl]-5-phenyl-methyl-4,5-dihydro-isoxazole-5-carbonylamino}-4-keto-5-bromo-pentanoic acid(LP and MP);

(3S)-3-{3-[(1S)-1-(naphthalene-2-carbonylamino)-2-methyl-propyl]-5-phenyl-methyl-4,5-dihydro-isoxazole-5-carbonylamino}-4-keto-5-(2,6-dichlorobenzoyloxy)-pentanoic acid(LP and MP);

(3S)-3-{3-[(1S)-1-(naphthalene-2-carbonylamino)-3-carboxy-propyl]-5-methyl)-4,5-dihydro-isoxazole-5-carbonylamino}-4-keto-5-phenoxy-pentanoic acid;

(3S)-3-{3-[(1S)-1-(quinoline-2-carbonylamino)-2-methyl-propyl]-5-phenoxymethyl-4,5-dihydro-isoxazole-5-carbonylamino}-4-keto-pentanoic acid;

(3S)-3-{3-[(1S)-1-(naphthalene-2-sulfonylamino)-2-methyl-propyl]-5-phenoxymethyl-4,5-dihydro-isoxazole-5-carbonylamino}-4-keto-5-phenoxy-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-(2-naphthyloxy)-pentanoic acid;

(3S)-3-{3-[(1S)-1-(naphthalene-2-carbonylamino)-2-methyl-propyl]-5-phenoxymethyl-4,5-dihydro-isoxazole-5-carbonylamino}-4-keto-5-(1-naphthyloxy)-pentanoic acid;

(3S)-3-{3-[(1S)-1-(2S)-2-acetylamino-succinoylamino)-3-carboxy-propyl]-5-methyl-4,5-dihydro-isoxazole-5-carbonylamino}-4-keto-5-phenoxy-pentanoic acid, (3S)-3-{3-[(1S)-1-(naphthalene-2-carbonylamino)-2-methyl-propyl]-4,5-dihydro-isoxazole-5-carbonylamino}-4-keto-5-(2-naphthyloxy)-pentanoic acid;

(3S)-3-{3-[2-methyl-(1S)-1-(2-naphthalenecarbonylamino)-propyl]-4,5-dihydro-isoxazole-5-carbonylamino}-4-keto-5-phenoxy-pentanoic acid (diasteromeric mixture);

(3S)-3-{3-[2-methyl-(1S)-1-(phenylmethyloxycarbonylamino)-propyl]-5-phenyl-methyl-4,5-dihydro-isoxazole-5-carbonylamino}-4-keto-5-diazo-pentanoic acid;

(3S)-3-{3-[2-methyl-(1S)-1-(phenylmethyloxycarbonylamino)-propyl]-5-phenyl-methyl-4,5-dihydro-isoxazale-5-carbonylamino}-4-keto-5-bromo-pentanoic acid;

(3S)-3-{3-[2-methyl-(1S)-1-(phenylmethyloxycarbonylamino)-propyl]5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(phenylethylcarbonylamino)-propyl]-5-phenyl-methyl-4,5-dihydro-isoxazole-5-carbonylamino}-4-keto-5-diazo-pentanoic acid;

(3S)-3-{3-[2-methyl-(1S)-1-(phenylethylcarbonylamino)-propyl]-5-phenylmethyl-4,5-dihydro-isoxazole-5-carbonylamino}-4-keto-5-bromo-pentanoic acid;

(3S)-3-{3-[2-methyl-(1S)-1-(phenylethylcarbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(1-naphthalenecarbonylamino)-propyl]-5-phenyl-methyl-4,5-dihydro-isoxazole-5-carbonylamino}-keto-4-diazo-pentanoic acid;

(3S)-3-{3-[2-methyl-(1S)-1-(1-naphthalenecarbonylamino)-propyl]-5-phenyl-methyl-4,5-dihydro-isoxazole-5-carbonylamino}-4-keto-5-bromo-pentanoic acid;

(3S)-3-{3-[2-methyl-(1S)-1-(1-naphthalenecarbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(1-naphtalenesulfonylamino)-propyl]-5-phenyl-methyl-4,5-dihydro-isoxazole-5-carbonylamino}-4-keto-5-diazo-pentanoic acid (diastereomeric mixture);

(3S)-3-{3-[2-methyl-(1S)-1-(1-naphtalenesulfonylamino)-propyl]-5-phenyl-methyl-4,5-dihydro-isoxazole-5-carbonylamino}-4-keto-5-bromo-pentanoic acid (diasteromeric mixture);

(3S)-3-{3-[2-methyl-(1S)-1-(1-naphtalenesulfonylamino)-propyl]-5-phenyl-methyl-4,5-dihydro-isoxazole-5-carbonylamino}-4-keto-5-(2,6-dichlorobenzoyloxy)-pentanoic acid (diastereomeric mixture);

(3S)-3-{3-[2-methyl-(1S)-1-((3-indolyl)ethylcarbonylamino)-propyl]-5-phenyl-methyl-4,5-dihydro-isoxazole-5-carbonylamino}-4-keto-5-diazo-pentanoic acid;

(3S)-3-{3-[2-methyl-(1S)-1-((3-indolyl)ethylcarbonylamino)-propyl]-5-phenyl-methyl-4,5-dihydro-isoxazole-5-carbonylamino}-4-keto-5-bromo-pentanoic acid;

(3S)-3-{3-[2-methyl-(1S)-1-((3-indolyl)ethylcarbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-((3-indolyl)methylcarbonylamino)-propyl]-5-phenyl-methyl-4,5-dihydro-isoxazole-5-carbonylamino}-4-keto-5-diazo-pentanoic acid;

(3S)-3-{3-[2-methyl-(1S)-1-((3-indolyl)methylcarbonylamino)-propyl]-5-phenyl-methyl-4,5-dihydro-isoxazole-5-carbonylamino}-4-keto-5-bromo-pentanoic acid;

(3S)-3-{3-[2-methyl-(1S)-1-((3-indolyl)methylcarbonylamino)-propyl]-5-phenyl-methyl-4,5-dihydro-isoxazole-5-carbonylamino}-4-keto-5-(2,6-dichlorobezoyloxy)-pentanoic acid;

(3S)-3-{3-[2-methyl-(1S)-1-(cinnamoylamino)-propyl]-5-phenylmethyl-4,5-dihydro-isoxazole-5-carbonylamino}-4-keto-5-diazo-pentanoic acid;

(3S)-3-{3-[2-methyl-(1S)-1-(cinnamoylamino)-propyl]-5-phenylmethyl-4,5-dihydro-isoxazole-5-carbonylamino}-4-keto-5-bromo-pentanoic acid;

(3S)-3-{3-[2-methyl-(1S)-1-cinnamoylamino)-propyl]-5-phenylmethyl-4,5-dihydro-isoxazole-5- carbonylamino}-4-keto-5-(2,6-dichlorobenzoyloxy)-pentanoic acid;

(3S)-3-{3-[2-methyl-(1S)-1-(phenylmethylsulfonylamino)-propyl]-5-phenyl-methyl-4,5-dihydro-isoxazole-5-carbonylamino}-4-keto-5-diazo-pentanoic acid;

(3S)-3-{3-[2-methyl-(1S)-1-(phenylmethylsulfonylamino)-propyl]-5-phenyl-methyl-4,5-dihydro-isoxazole-5-carbonylamino}-4-keto-5-bromo-pentanoic acid;

(3S)-3-{3-[2-methyl-(1S)-1-(phenylmethylsulfonylamino)-propyl]-5-phenyl-methyl-4,5-dihydro-isoxazole-5-carbonylamino}-4-keto-(2,6-dichlorobenzoyloxy)-pentanoic acid;

(3S)-3-{3-[2-methyl-(1S)-1-(quinoline-2-yl-carbonylamino)-propyl]-4,5-dihydro-isoxazole-5-carbonylamino}-4-keto-5-diazo-pentanoic acid;

(3S)-3-{3-[2-methyl-(1S)-1-(quinoline-2-yl-carbonylamino)-propyl]-4,5-dihydro-isoxazole-5-carbonylamino}-4-keto-5-bromo-pentanoic acid;

(3S)-3-{3-[2-methyl-(1S)-1-(quinoline-2-yl-carbonylamino)-propyl]-4,5-dihydro-isoxazole-5-carboylamino}-4-keto-5-(2,6-dichlorobenzoyloxy)-pentanoic acid;

(3S)-3-{3-[2-methyl-(1S)-1-quinoline-2-yl-carbonylamino)-propyl]-4,5-dihydro-isoxazole-5-carbonylamino}-4-keto-5-phenoxy-pentanoic acid;

(3S)-3-{3-[2-methyl-(1S)-1-(quinoline-2-yl-carbonylamino)-propyl]-5-phenyl-methyl-4,5-dihydro-isoxazole-5-carbonylamino}-4-keto-5-diazo-pentanoic acid;

(3S)-3-{3-[2-methyl-(1S)-1-(quinoline-2-yl-carbonylamino)-propyl]-5-phenyl-methyl-4,5-dihydro-isoxazole-5-carbonylamino}-4-keto-5-bromo-pentanoic acid;

(3S)-3-{3-[2-methyl-(1S)-1-(quinoline-2-yl-carbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-quinoline-2-yl-carbonylamino)-propyl]-5-phenyl-methyl-4,5-dihydro-isoxazole-5-carbonylamino}-4-keto-5-phenoxy-pentanoic acid;

(3S)-3-{3-[2-methyl-(1S)-1-(quinoline-2-yl-carbonylamino)-propyl]-5-(1-imidazolyl-methyl)-4,5-dihydro-isoxazole-5-carbonylamino}-4-keto-5-phenoxy-pentanoic acid;

(3S)-3-{3-[2-methyl-(1S)-1-(2-naphthalenecarbonylamino)-propyl]-4,5-dihydro-isoxazole-5-carbonylamino}-4-keto-pentanoic acid;

(3S)-3-{3-[(1S)-1-(succinoylamino)-3-carboxy-propyl]-5-methyl-4,5-dihydro-isoxazole-5-carbonylamino}-4-keto-5-phenoxy-pentanoic acid;

(3S)-3-{3-[2-methyl-(1S)-1-(succinoylamino)-propyl]-5-methyl-4,5-dihydro-isoxazole-5-carbonylamino}-4-keto-5-phenoxy-pentanoic acid;

(3S)-3-{3-[2-methyl-(1S)-1-(1-naphthalenylcarbonylamino)-propyl]-5-phenyl-methyl-4,5-dihydro-isoxazole-5-carbonylamino}-4-keto-5-(1-piperidinyl)-pentanoic acid;

(3S)-3-{3-[2-methyl-(1S)-1-(isoquinoline-1-carbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-isoquinole-3-carbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(quinoline-4-carbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(benzofuran-2-carbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(naphthalene-1-carbonylamino)-propyl]-5-phenyl-methyl-4,5-dihydro-isoxazole-5-carbonylamino}-4-keto-5-(2,6-difluorobenzoyloxy)-pentanoic acid;

(3S)-3-{3-[2-methyl-(1S)-1-(quinoline-3-carbonylamino)-propyl]-5-phenyl-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(naphthalene-1-carbonylamino)-propyl]-5-phenyl-methyl-4,5-dihydro-isoxazole-5-carbonylamino}-4-keto-5-(2,6-dimethylbenzoyloxy)-pentanoic acid[diastereomeric mixture];

(3S)-3-{3-[2-methyl-(1S)-1-quinoline-8-carbonylamino)-propyl]-5-phenylmethyl-4,5-dihydro-isoxazole-5-carbonylamino}-4-keto-5-(2,6-dichlorobenzoyloxy)-pentanoic acid [diastereomeric mixture];

(3S)-3-{3-[2-methyl-(1S)-1-(indole-2-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(indole-3-carbonylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(naphthalene-1-carbonylamino)-propyl]-5-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(benzofuran-2-carbonylamino)-propyl]-5-methyl-4,5-dihydro-isoxazole-5-carbonylamino}-4-keto-5-(2,6-dichlorobenzoyloxy)-pentanoic acid;

(3S)-3-{3-[3-carboxy-(1S)-1-(succinoylamino)-propyl]-5-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-methyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-propyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-methyl-4,5-dihydro-isoxazole-5-carbonylamino}-4-keto-5-(N-piperidine)-pentanoic acid[diastereomeric mixture];

(3S)-3-{3-[2-methyl-(1S)-1-(succinoylamino)-propyl]-5-methyl-4,5-dihydro-isoxazole-5-carbonylamino}-4-keto-5-(N-pyrrolidine)-pentanoic acid [diastereomeric mixture];

(3S)-3-{3-[2-methyl-(1S)-1-(succinoylamino)-propyl]-5-butyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-methyl-4,5-dihydro-isoxazole-5-carbonylamino}-4-keto-5-(2-naphthyloxy)-pentanoic acid;

(3S)-3-{3-[2-methyl-(1S)-1-(succinoylamino)-propyl]5-propyl-4,5-dihydro-isoxazole-5-carbonylamino}-4-keto-5-phenoxy-pentanoic acid [diastereomeric mixture];

(3S)-3-{3-[2-methyl-(1S)-1-(succinoylamino)-propyl]-5-hydroxymethyl-4,5-dihydro-isoxazole-5-carbonylamino}-4-keto-5-(2,6-dichlorobenzoyloxy)-pentanoic acid [diastereomeric mixture];

(3S)-3-{3-[2-methyl-(1S)-1-(succinoylamino)-propyl]-5-phenylmethyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-methoxymethyl-4,5-dihydro-isoxazole-5-carbonylamino}-4-keto-5-(2,6-dichlorobenzoyloxy)-pentanoic acid [diastereomeric mixture];

(3S)-3-{3-[2-methyl-(1S)-1-(succinoylamino)-propyl]-5-n-pentyl-4,5-dihydro-isoxazole-5-carbonylamino}-4-keto-5-(2,6-dichlorobenzoyloxy)-pentanoic acid;

(3S)-3-{3-[2-methyl-(1S)-1-(succinoylamino)-propyl]-5-ethyl-4,5-dihydro-isoxazole-5-carbonylamino}-4-keto-5-(2,6-dichlorobenzoyloxy)-pentanoic acid;

(3S)-3-{3-[2-methyl-(1S)-1-(glutaroylamino)-propyl]-5-methyl-4,5-dihydro-isoxazole-5-carbonylamino}-4-keto-5-(2,6-dichlorobenzoyloxy)-pentanoic acid; and (3S)-3-{3-[2-methyl-(1S)-1-(phenylmethyloxycarbonylamino)-propyl]-4,5-dihydro-isoxazole-5-carbonylamino}-4-keto-pentanoic acid methyl ester.

6. A caspase inhibitor which comprises an isoxazoline derivative of the formula (I), the pharmaceutically acceptable salts, esters or stereochemically isomeric forms thereof as claimed in any one of claims 1 to 5.

7. A pharmaceutical composition for treating disease caused by inflammation or apoptosis which comprises as an active ingredient a therapeutically effective amount of an isoxazoline derivative of the formula (I), the pharmaceutically acceptable salts, esters or stereochemically isomeric forms thereof as claimed in claim 1 and pharmaceutically acceptable carrier.

8. The composition according to claim 7, wherein the disease is selected from the group consisting of the diseases in which cells are abnormally died, dementia, cerebral stroke, brain impairment due to AIDS, diabetes, gastric ulcer, cerebral injure by hepatitis, fulminant hepatic failure (FHF), sepsis, organ transplantation rejection reaction, rheumatic arthritis, cardiac cell apoptosis due to ischemic cardiac diseases and anti-inflammation.

9. The composition according to claim 7, wherein the disease is fulminant hepatic failure in human.

10. The composition according to claim 7, in the form for administration orally, percutaneously, or by parenteral injection.

11. A method of treating patients suffering from the diseases caused by caspases activation, which comprises a local or systemic administration of a therapeutically effective amount of an isoxazoline derivative of the formula (I), the pharmaceutically acceptable salts, the esters or stereochemically isomeric forms thereof, according to any one of claims 1 to 5 or the pharmaceutically composition according to any one of claims 7 to 10.

12. A process for preparing a pharmaceutical composition for treating disease caused by inflammation or apoptosis which comprises as an active ingredient a therapeutically effective amount of an isoxazoline derivative and pharmaceutically acceptable carrier, the process comprising the step of:

intimately mixing a pharmaceutically acceptable carrier with a therapeutically effective amount of a compound of formula (I) as claimed in any of claims 1 to 5.

13. A process for preparing a derivative of the formula (I), the pharmaceutically acceptable salts, ester or stereochemically isomeric forms thereof, characterized in that hydroxamoyl chloride (VI) is reacted with acrylate derivative (VII) to give isoxazoline derivative (VIII), and isoxazoline derivative (VIII) is then deprotected and $R^4$ is introduced therein to give a compound of formula (IX) which is then reacted with a compound of formula (X) and, if necessary, the isoxazoline derivative (VIII) is directly reacted with the compound (X) to give a compound of formula (I), and if necessary, the compound of formula (I) having the protecting group $P_1$ is converted into other compound having substitutent $R^4$

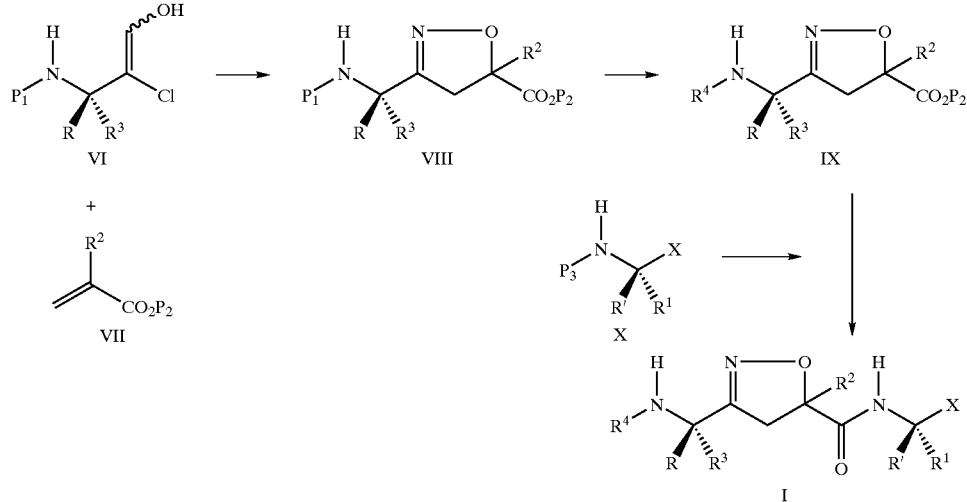

in which substituents are the same as defined in claim 1.

* * * * *